US012024537B2

(12) United States Patent
Seifert

(10) Patent No.: US 12,024,537 B2
(45) Date of Patent: Jul. 2, 2024

(54) COMPOSITIONS AND METHODS FOR CHEMICAL SYNTHESIS

(71) Applicant: SEDERMA, Le Perray-en-Yvelines (FR)

(72) Inventor: Cole Seifert, Le Perray-en-Yvelines (FR)

(73) Assignee: Sederma, Le Perray-en-Yvelines (FR)

( * ) Notice: Subject to any disclaimer, the term of this patent is extended or adjusted under 35 U.S.C. 154(b) by 523 days.

(21) Appl. No.: 17/104,166

(22) Filed: Nov. 25, 2020

(65) Prior Publication Data

US 2021/0079036 A1 Mar. 18, 2021

Related U.S. Application Data

(63) Continuation-in-part of application No. PCT/US2020/015132, filed on Jan. 26, 2020, and a continuation-in-part of application No. PCT/US2019/033296, filed on May 21, 2019.

(60) Provisional application No. 62/800,142, filed on Feb. 1, 2019, provisional application No. 62/678,564, filed on May 31, 2018.

(51) Int. Cl.
| | |
|---|---|
| C07K 1/06 | (2006.01) |
| C07F 9/12 | (2006.01) |
| C07F 9/32 | (2006.01) |
| C07F 9/53 | (2006.01) |

(52) U.S. Cl.
CPC .............. *C07K 1/063* (2013.01); *C07F 9/12* (2013.01); *C07F 9/3282* (2013.01); *C07F 9/5325* (2013.01)

(58) Field of Classification Search
None
See application file for complete search history.

(56) References Cited

U.S. PATENT DOCUMENTS

| | | | |
|---|---|---|---|
| 4,617,584 A | 10/1986 | Ikeya et al. | |
| 5,516,891 A | 5/1996 | Siwruk et al. | |
| 6,753,409 B1 | 6/2004 | Chrzan et al. | |
| 8,093,435 B2 | 1/2012 | Chiba et al. | |
| 8,383,770 B2 | 2/2013 | Dalton et al. | |
| 8,633,298 B2 | 1/2014 | Chiba et al. | |
| 8,716,439 B2 | 5/2014 | Murao et al. | |
| 9,353,148 B2 | 5/2016 | Takahashi | |
| 10,947,267 B2 | 3/2021 | Li et al. | |
| 2001/0018512 A1 | 8/2001 | Blanchard | |
| 2003/0018164 A1 | 1/2003 | Eggen et al. | |
| 2004/0214989 A1 | 10/2004 | Chiba et al. | |
| 2008/0287649 A1 | 11/2008 | Chen et al. | |
| 2009/0069538 A1 | 3/2009 | Murao et al. | |
| 2009/0299103 A1 | 12/2009 | Chiba et al. | |
| 2010/0029904 A1 | 2/2010 | Chiba et al. | |
| 2010/0240867 A1 | 9/2010 | Takahashi | |
| 2010/0249374 A1 | 9/2010 | Takahashi | |
| 2014/0100355 A1 | 4/2014 | Acemoglu et al. | |
| 2014/0178302 A1 | 6/2014 | Lattuada et al. | |
| 2014/0213814 A1 | 7/2014 | Monnaie et al. | |
| 2015/0023987 A1 | 1/2015 | Borch et al. | |
| 2016/0053179 A1 | 2/2016 | Takata et al. | |
| 2016/0165916 A1 | 6/2016 | Howell et al. | |
| 2016/0257725 A1 | 9/2016 | Verdine et al. | |
| 2018/0215782 A1 | 8/2018 | Kono et al. | |
| 2019/0330262 A1 | 10/2019 | Li et al. | |

FOREIGN PATENT DOCUMENTS

| | | |
|---|---|---|
| EP | 2716650 A1 | 4/2014 |
| EP | 3778621 A1 | 2/2021 |
| JP | 2003500415 A | 1/2003 |
| JP | 2003055396 A | 2/2003 |
| JP | 2003183298 A | 7/2003 |
| JP | 2003183298 A | 7/2003 |
| JP | 2004059509 A | 2/2004 |
| WO | 9325571 A1 | 12/1993 |
| WO | 0071569 A1 | 11/2000 |
| WO | 2007034812 A1 | 3/2007 |
| WO | 2007099656 A1 | 9/2007 |
| WO | 2007122847 A1 | 11/2007 |
| WO | 2010104169 A1 | 9/2010 |
| WO | 2010113939 A1 | 10/2010 |
| WO | 2011152603 A1 | 12/2011 |
| WO | 2013117440 A1 | 8/2013 |
| WO | 2014093723 A2 | 6/2014 |
| WO | 2017112809 | 8/2018 |

(Continued)

OTHER PUBLICATIONS

Seki et al. "Cellular Protection of SNAP-25 against Botulinum Neurotoxin/A: Inhibition of Thioredoxin Reductase through a Suicide Substrate Mechanism" Journal of the American Chemical Society, 2016, vol. 138, No. 17, pp. 5568-5575 and Supporting Information pp. S1-S43.*
Daisuke Takahashi et al; Development of an efficient liquid-phase peptide synthesis protocol using a novel luorene-derived anchor support compound with Fmoc chemistry; Ajiphase; Tetrahedron Letters; 53 (2012) 1936-1939.
Daisuke Takahashi et al; Novel diphenylmethyl-Derived Amide Protecting Group for Efficient Liquid-Phase Peptide Synthesis: Ajiphase; Organic Letters; 2012; vol. 14, No. 17; 4514-4517.
Daisuke Takahashi; Ajiphaseu: A Highly Efficient Synthetic Method for One-Pot Peptide Elongation in the Solution Phase by an Fmoc Strategy; Angew. Chem. Int. Ed. 2017; 56; 7803-7807.
Information Disclosure Statement; U.S. Appl. No. 15/555,484; Jul. 7, 2020 ; 3 pgs.

(Continued)

*Primary Examiner* — Joseph R Kosack
(74) *Attorney, Agent, or Firm* — Buchanan Ingersoll & Rooney PC

(57) ABSTRACT

The disclosure relates to chemical compositions that can include anchor molecules for chemical synthesis. GAP anchor molecules can include GAP constituents, linker constituents, and spacer constituents. Anchor molecules can be used to synthetically manufacture peptides. A novel method of solution-phase peptide synthesis is also disclosed that utilizes novel group-assisted purification protecting groups to facilitate efficient, scalable chemistry to synthetically manufacture peptides.

6 Claims, 21 Drawing Sheets

(56) References Cited

FOREIGN PATENT DOCUMENTS

| WO | 2019198834 A1 | 10/2019 |
| WO | 2019217116 A1 | 11/2019 |
| WO | 2019231760 A1 | 12/2019 |
| WO | 2022115825 A1 | 6/2022 |
| WO | 2020159837 A1 | 8/2022 |
| WO | 2022226536 A1 | 10/2022 |

OTHER PUBLICATIONS

Information Disclosure Statement; U.S. Appl. No. 15/555,484; Sep. 1, 2017; 5 pgs.
International Search Report; PCT/JP2016/056319 dated May 31, 2016; 2 pgs; Japan Patent Office.
Ivo F. Eggen et al.; A novel method for repetitive peptide synthesis in solution without isolation of intermediates; J. Peptide Sci. 11; (2005); 633-641 .
James E. Sheppeck; A convenient and scaleable procedure for removing the Fmocgroup in solution; Tetrahedron Letters 41 (2000) 5329-53333.
Louis A. Carpino et al; Rapid, Continuous Solution-Phase Peptide Synthesis: Application to Peptides of Pharmaceutical Interest; Organic Process Research & Development 2003, 7, 28-37.
International Search Report and Written Opinion for International Application No. PCT/US2021/072297, dated Mar. 17, 2022, 11 pages.
Adiseshu Kattuboina, Parminder Kaur, Thao Nguyen, Guigen Li; Chiral N-phosphonyl imine chemistry: asymmetric 1,2-additionsof allylmagnesium bromides; Tetrahedron Letters 49 (2008) 3722-3724; Elsevier Ltd.
Adriano Mollicaa, Francesco Pinnen, Stefanucci Azzurra and Roberto Costante; The Evolution of Peptide Synthesis: From Early Days to Small Molecular Machines; Current Bioactive Compounds 2013, pp. 184-202, vol. 9, No. 3; Bentham Science Publishers.
Bachem. Tips and Trick for Solid Phase Peptide Synthesis from the Experts at Bachem. Solid Phase Peptide Synthesis 2016, pp. 1-55.
Chun-Chi Chen, Basker Rajagopal, Xuan Yu Liu, Kuan Lin Chen, Yu-Chang Tyan, Ful Lin, Po-Chiao Lin; A mild removal of Fmoc group using sodium azide; Amino Acids (2014) 46:367-374; Springer-Verlag Wien.
Clara Brieke and Max J. Cryle; A Facile Fmoc Solid Phase Synthesis Strategy to Access Epimerization-Prone Biosynthetic Intermediates of Glycopeptide Antibiotics; Org. Lett. 2014, 16, 2454-2457; American Chemical Society.
David Dailler, Gregory Danoun and Olivier Baudoin; A General and Scalable Synthesis of Aeruginos Marine Natural Products Based on Two Strategic C(sp3)—H Activation Reactions; Angew. Chem. Int. Ed. 2015, 54, 1-5; Wiley-VCH Verlag Gmbh & Co. KGaA, Weinheim.
De Marco et al. "C > N and N >C Solution Phase Peptide Synthesis Using the N-acyl 4-Nitrobenzenesulfonamide as Protection of the Carboxylic Function"; Organic and Biomolecular Chemistry, Jul. 21, 2013, vol. 11, Iss. 23, pp. 3786-3796.
Elias Kaufmann, Hiromu Hattori, Hideki Miyatake-Ondozabal and Karl Gademann; Total Synthesis of the Glycosylated Macrolide Antibiotic Fidaxomicin; Organic Letters; Jun. 1, 2015; 17; 3514-3517; ACS AuthorChoice.
European Search Report (EP 16880050.6) dated May 27, 2019.
Guanghui An, Cole Seifert and Guigen Li; N-Phosphonyl/phosphinyl imines and groupassistedpurification (GAP) chemistry/technolog; Organic & Biomolecular Chemistry; Dec. 9, 2014;p. 1-18; The Royal Society of Chemistry www.rsc.org/obc.
Guanghui An, Cole Seifert, Hao Sun, Yi Pan, and Guigen Li; Group-Assisted Purification (GAP) for Protection of Amino Acids Using N-Phosphonyl Functional Groups; Heterocycles, vol. 90, No. 1, 2015; pp. 344-356; The Japan Institute of Heterocyclic Chemistry.
Guanghui An, Wei Zhou, Xiaokang Xu, Yi Pan and Guigen Li; Solution-Phase-Peptide Synthesis Without Purification of Column Chromatography and Recrystallization by Protecting Amino Acid Esters With Phosphinyl Chloride; Heterocycles, vol. 90, No. 2, 2015, pp. 1405-1418; The Japan Institute of Heterocyclic Chemistry.
Haruaki Yajima; Synthetic Aspects of Peptides; Journal of Synthetic Organic Chemistry, 1974, 32(10), 826-832.
Hou et al. "Progress in Chemical Synthesis of Peptides and Proteins"; Transactions of Tiajin University; Jun. 23, 2017, vol. 23, Iss.5, pp. 401-419.
International Search Report; PCT/US2016/068112; dated May 8, 2017; pp. 1-3.
International Search Report; PCT/US2019/029569; dated Jul. 12, 2009; pp. 1-2.
International Search Report; PCT/US2019/033296; dated Jul. 15, 2009; p. 1.
International Search Report; PCT/US2020/15132; dated Jun. 4, 2020 pp. 1-3.
Isidro-Llobet, Albert, Mercedes Alvarez and Fernando Albericio; Amino Acid-Protecting Groups; Chem. Rev. 2009, 109, 2455-2504; American Chemical Society.
Janssen, M.C.C.; Vogt, D.; Müller, C.; 'Click' dendritic phosphines: design, synthesis, application in Suzuki coupling, and recycling by nanofiltration; Catalysis and Organometallic Chemistry; Department of Chemical Engineering and Chemistry; Advanced Synthesis & Catalysis, 351(3), 313-318. Wiley-VCH Verlag. ISSN 1615-4150; 2009.
Jensen, Knud J. Chapter 1: Peptide Synthesis. Pharmaceutical Formulation Development of Peptides and Proteins 2013, pp. 1-16.; CRC Press/Taylor & Francis Group, 2013; Boca Raton, FL.
Jianbin Wu, Guanghui An, Siqi Lin, Jianbo Xie, Wei Zhou, Hao Sun, Yi Pana and Guigen Li; Solution-phase-peptide synthesis via the group-assisted purification (GAP) chemistry without using chromatography and recrystallization; Chem. Commun., 2014, 50, 1259-1261; The Royal Society of Chemistry.
Jian-Bo Xie, Jian Luo, Timothy R. Winn, David B. Cordes and Guigen Li; Group-assisted purification (GAP) chemistry for the synthesis of Velcade via asymmetric borylation of N-phosphinylimines; Beilstein Journal Organic Chemistry; Mar. 31, 2014; Beilstein J. Org. Chem. 2014, 10, 746-751; Beilstein-Institut.
Jianlin Han, Teng Ai, Thao Nguyen and Guigen Li;Chiral N-Phosphonyl Imine Chemistry: Asymmetric Additions of Ester Enolates for the Synthesis of b-Amino Acids; Chem Biol Drug Des 2008; 72: 120-126; Blackwell Publishing Limited.
Kattuboina, A. et al. "Chiral N-phosphonyl imine chemistry: new reagents and their applications for asymmetric reactions." Tetrahedron Lett. 2008, 49, 1573-1577.
Mariagiovanna Spinella, Rosaria De Marco, Emilia L. Belsito, Antonella Leggio, Angelo Liguori; The dimethylsulfoxonium methylide as unique reagent for the simultaneous deprotection of amino and carboxyl function of N-Fmoc-rx-amino acid and N-Fmoc-peptide esters; Tetrahedron 69 (2013) 2010-2016; Elsevier Ltd.
Masayoshi Mochizuki, Shugo Tsuda, Kyoko Tanimura, and Yuji Nishiuchi; Regioselective Formation of Multiple Disulfide Bonds with the Aid of Postsynthetic S-Tritylation; Organic Letters; Apr. 10, 2015; 17; pp. 2202-2205; American Chemical Society.
Meiyun Shi, Yan Yang, Xiaotong Zhou, Lanlan Cai, Chunxue Fang, Can Wang, Heping Sun, Yantong Sun, Yin Gao, Jingkai Gu, J. Paul Fawcett; Determination of thymopentin in beagle dog blood by liquid chromatography with tandem mass spectrometry and its application to a preclinical pharmacokinetic study; J. Sep. Sci. 2015, 38, pp. 1351-1357; Wiley-VCH Verlag Gmbh & Co. KGaA, Weinheim.
Ming-Xia Zhu, Wen-Li Wan, Hai-Shen Li, Jing Wang, Gui-An Chen, Xiao-Yan Ke; Thymopentin enhances the generation of T-cell lineage derived from human embryonic stem cells in vitro; Experimental Cell Research 331 ( 2015) 387-398; Elsevier Inc.
Muriel Amblard, Jean-Alain Fehrentz, Jean Martinez and Gilles Subra; Methods and Protocols of Modern Solid Phase Peptide Synthesis; Molecular Biotechnology; pp. 239-254; vol. 33, 2006; Humana Press Inc.
Padmanabha V. Kattamuri, Teng Ai, Suresh Pindi, Yinwei Sun, Peng Gu, Min Shi, and Guigen Li; Asymmetric Synthesis of a.-Amino-1,3-dithianes via Chiral N-Phosphonyl Imine-Based Umpolung

(56) References Cited

OTHER PUBLICATIONS

Reaction Without Using Chromatography and Recrystallization; The Journal of Organic Chemistry; Mar. 15, 2011; pp. 2792-2797; vol. 76; bubs.acs.org/joc.

Parminder Kaur, Walter Wever, Suresh Pindi, Raizada Milles, Peng Gu, Min Shi and Guigen Li; The GAL Chemistry for Chiral N-phosphonyl imine-based Strecker reaction; Green Chem., 2011, 13, 1288; The Royal Society of Chemistry.

Pradeep K Sharma, Leo J. Romanczyk, Jr., Leelakrishna Kondaveti, Bollu Reddy, Jeeva Arumugasamy, Richard Lombardy, Yanni Gou, and Hagen Schroeter; Total Synthesis of Proanthocyanidin A 1, A2, and Their Stereoisomers; Organic Letters; Mar. 4, 2015; 17, 2306-2309; American Chemical Society.

Pubchem. CID 129303937; Aug. 4, 2017; pp. 1-11. Retrieved from the Internet ; p. 2.

Pubmed Compound Summary for CID 71676245, 'AKOS016034578', U.S. National Library of Medicine, Sep. 4, 2013 (Sep. 4, 2013), p. 3.

R. B. Merrifield; Solid Phase Peptide Synthesis I. The Synthesis of a Tetrapeptide;. J. Am. Chem. Soc. 1963; pp. 2149-2154; vol. 85.

Raymond Behrendt, Simon Huber, Roger Marti and Peter White; New t-butyl based aspartate protecting groups preventing aspartimide formation in Fmoc SPPS; Journal of Peptide Science; Jun. 15, 2015; 21: 680-687; European Peptide Society and John Wiley & Sons, Ltd.

Saranya Chandrudu, Pavla Simerska and Istvan Toth; Chemical Methods for Peptide and Protein Production; Molecules Open Access Article; Apr. 12, 2013; pp. 4373-4388; Creative Commons Attribution.

Seifert et al. "GAP Peptide Synthesis via Design of New Gap Protecting Group: An Fmoc/tBu Synthesis of Thymopentin Free from Polymers, Chromatograpy and Recrystallization", European Journal of Organic Chemistry, Mar. 8, 2016; vol. 2016, Iss. 9, pp. 1714-1719.

Shelton, P. T.; Jensen, K; Linkers, Resins, and General Procedures for Solid-Phase Peptide Synthesis. In Peptide Synthesis and Applications, 2nd Edition, Jensen, K. J.; Shelton, P. T.; Pedersen, S. L., Eds. Humana Press Inc: Totowa, 2013; vol. 1047, pp. 23-41.

Stefan B. Lawrenson, Roy Arav and Michael North; The greening of peptide synthesis; Green Chem., 2017, 19, 1685-1691; The Royal Society of Chemistry.

Suresh Pindi, Parminder Kaur, Gaurav Shakya and Guigen Li; N-Phosphinyl Imine Chemistry (I): Design andSynthesis of Novel N-Phosphinyl Imines and their Application to Asymmetric aza-Henry Reaction; Chem Biol Drug Des 2011; 77: 20-29; Sep. 19, 2010; Chemical Biology & Drug Design.

Takayuki Shioiri; Recent Advances of Protective Groups in Peptide Synthesis; Journal of Synthetic Organic Chemistry, 1978, 36(9), 740-748.

Teng Ai, Guigen Li; Chiral N-phosphonyl imine chemistry: Asymmetric synthesis of a,b-diamino esters by reacting phosphonyl imines with glycine enolates; Bioorganic & Medicinal Chemistry Letters 19 (2009) 3967-3969;Mar. 5, 2009; Published by Elsevier Ltd.

Tingting Fu, Hongwei Qiao, Zhimin Peng, Gaobo Hu, Xueji Wu, Yuxing Gao and Yufen Zhao; Palladium-catalyzed air-based oxidative coupling of arylboronic acids with H-phosphine oxides leading to aryl phosphine oxides; Org. Biomol. Chem.; Feb. 26, 2014 ; The Royal Society of Chemistry12, 2895-2902.

Wuts, P. G. M. Greene's Protective Groups in Organic Synthesis. 5 ed.; John Wiley & Sons, Inc: New Jersey, 2014.

Granoth et al., "A Monocyclic Phosphorane Oxide Anion and the Extraordinary Reactivity of its Tautomeric Phosphine Oxide Alkoxide", Journal of the Chemical Society, Chemical Communications, 1981, pp. 981-982.

Sukhorukov et al., "Rearrangement of Phosphinotripenylcarbinol", Izvestiya Akademii Nauk SSSR Seriuya Khimicheskaya (1975), (2), pp. 463-46, Abstracted in HCAPLUS 1975:410287.

Crich et al., "Dichotomous Reaction Pathways in The Reaction of Triarylphosphine Oxides With Mederwein's Salt", Tetrahedron Letters, 1989, vol. 30, No. 4, pp. 475-476.

Zhang et al "Ni(ii)ZN Catalyzed Reductive Coupling of Aryl Halides with Diphenylphosphine Oxide in Water", Organic Letters, 2011, vol. 13, No. 13, pp. 3478-3481.

International Search Report and Written Opinion for International Application No. PCT/US2022/071870, dated Sep. 1, 2022, 11 pages.

Wu et al., "Solution-Phase-Peptide Synthesis via the Group Assisted Purification (GAP) Chemistry Without Using Chromatography and Recrystallization", Chemical Communications, Feb. 7, 2014, vol. 50, No. 10, pp. 1-9.

Pubchem, Substance Record for SID 135946876, Modify Date Jan. 25, 2017, retrieved from the Internet at https://pubchem.ncbi.nlm,nih.gov/substance/135946876, 6 pages.

Seifert et al., "Asymmetric Carbamoyl Anion Additions to Chiral N-Phosphonyl Imines via the GAP Chemistry Process and Stereoselectivity Enrichments", The Journal of Organic Chemistry, 2015, vol. 80, pp. 447-452.

\* cited by examiner

Structures of the type H-Gap, H-Linker-Gap, H-Linker-Gap, H-Linker-Spacer-Gap
                                                        └─Gap
or H-Linker-Spacer-Gap, collectively known together as H-Anchor molecules, where H is the element
       └─Spacer-Gap
Hydrogen, and Linker, Spacer, and Gap molecules are as defined below

---

⸺Linker⸺ consists of the following:

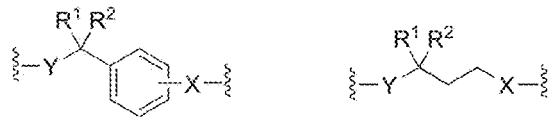

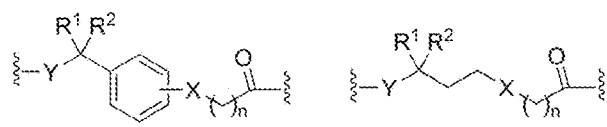

Wherein:
X = Y as defined below; -C(O)-; -(CH$_2$)$_a$- where "a" is as defined below
Y = S; NH; NMe; NEt; NBn; NPh; or O
R$^1$ = -(CH$_2$)$_b$-H where "b" is as defined below; -CCl$_3$; -CF$_3$; phenyl; isopropyl; tert-butyl; chlorophenyl; dichlorophenyl; methoxyphenyl; or dimethoxyphenyl
R$^2$ = -(CH$_2$)$_c$-H where "c" is as defined below; -CCl$_3$; -CF$_3$; phenyl; isopropyl; tert-butyl; chlorophenyl; dichlorophenyl; methoxyphenyl; or dimethoxyphenyl
a,b,c, and n = separate values that can be chosen from the following data set: any integer between 0 and 30

---

⸺Linker⸺ consists of the following:
     │
     └─

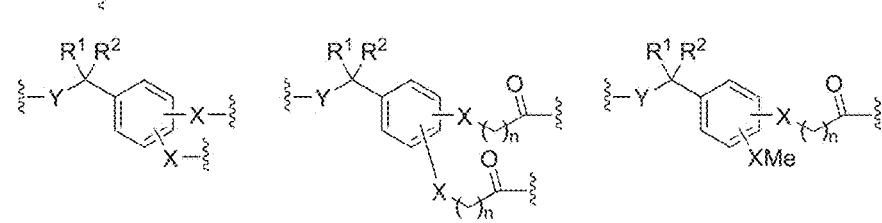

Wherein:
X = Y as defined below; -C(O)-; -(CH$_2$)$_a$- where "a" is as defined below
Y = S; NH; NMe; NEt; NBn; NPh; or O
R$^1$ = -(CH$_2$)$_b$-H where "b" is as defined below; -CCl$_3$; -CF$_3$; phenyl; isopropyl; tert-butyl; chlorophenyl; dichlorophenyl; methoxyphenyl; or dimethoxyphenyl
R$^2$ = -(CH$_2$)$_c$-H where "c" is as defined below; -CCl$_3$; -CF$_3$; phenyl; isopropyl; tert-butyl; chlorophenyl; dichlorophenyl; methoxyphenyl; or dimethoxyphenyl
a,b,c, and n = separate values that can be chosen from the following data set: any integer between 0 and 30

*FIG. 20A*

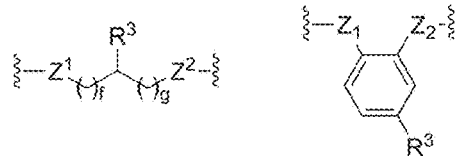

—Spacer— consists of the following:

Wherein:
$Z^1$ = S; O; NH; NMe; NEt; NBn; NPh; -C(O)-; -(CH$_2$)$_d$- where "d" is as defined below
$Z^2$ = S; O; NH; NMe; NEt; NBn; NPh; -C(O)-; -(CH$_2$)$_e$- where "e" is as defined below
d, e, f, g, h, i, and z = separate values that can be chosen from the following data set: any integer between 0 and 30
$R^3$ = H, methyl, ethyl, propyl, isopropyl, benzyl, isobutyl, sec-butyl, tert-butyl, 2-(methylmercapto)ethyl, or the structures listed below:

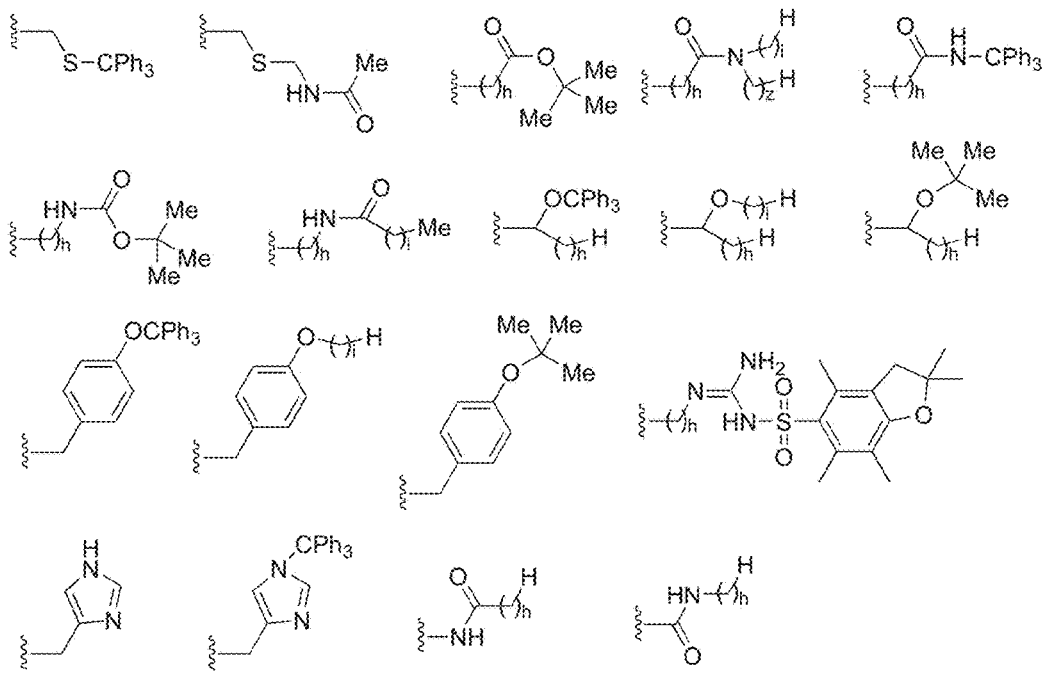

*FIG.20B*

⸞—Gap consists of the following:

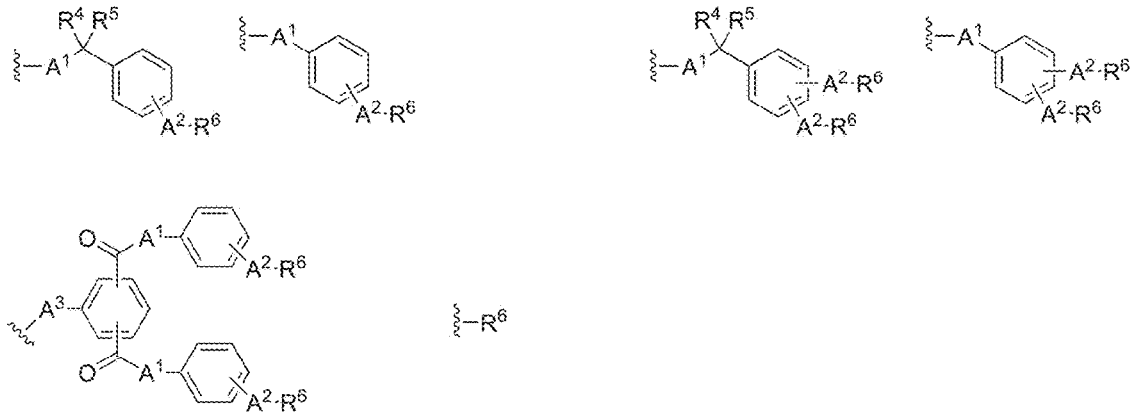

Wherein:
$A^1$ = S; O; NH; NMe; NEt; NBn; NPh; -C(O)-; -(CH$_2$)$_j$- where "j" is as defined below
$A^2$ = S; O; NH; NMe; NEt; NBn; NPh; -C(O)-; -(CH$_2$)$_k$- where "k" is as defined below
$A^3$ = S; O; NH; NMe; NEt; NBn; NPh
$R^4$ = -(CH$_2$)$_m$-H where "m" is as defined below; -CCl$_3$; -CF$_3$; phenyl; isopropyl; tert-butyl; chlorophenyl; dichlorophenyl; methoxyphenyl; or dimethoxyphenyl
$R^5$ = -(CH$_2$)$_p$-Me where "p" is as defined below; -CCl$_3$; -CF$_3$; phenyl; isopropyl; tert-butyl; chlorophenyl; dichlorophenyl; methoxyphenyl; or dimethoxyphenyl
$R^6$ = Dpp; Dpop; or Dap
$R^7$ = C$_y$H$_{(2y+1)}$ where "y" is as defined below; OC$_y$H$_{(2y+1)}$ where "y" is as defined below; NHC$_y$H$_{(2y+1)}$ where "y" is as defined below; (2-ethyl)hexyl; or isooctyl.

j, k, m, p, and y = separate values that can be chosen from the following data set: any integer between 0 and 30 wherein:

⸞—Dpp is an abbreviation for the following: ⸞—P(=O)(Ph)Ph

⸞—Dpop is an abbreviation for the following: ⸞—P(=O)(OPh)OPh

⸞—Dap is an abbreviation for the following: ⸞—P(=O)(R$^7$)R$^7$

*FIG.20C*

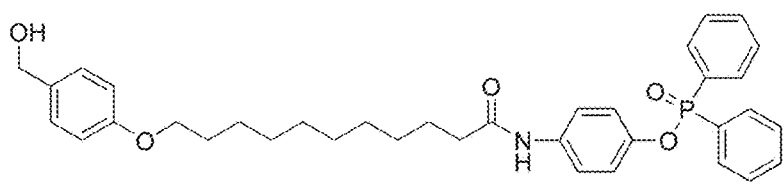
This H-Anchor molecule uses the H-Linker-Spacer-Gap format, with the following parent structures:
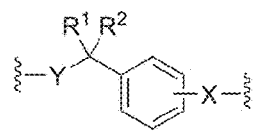
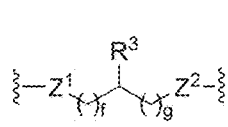
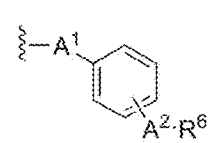
Linker    Spacer    Gap
Where Y = O; $R^1$ = H; $R^2$ = H; X = O in the para position; $Z^1$ = -(CH$_2$)- where d = 1; f = 8; $R^3$ = H; g = 0; $Z^2$ = -C(O)-; $A^1$ = NH; $A^2$ = O in the para position; $R^6$ = Dpp
*FIG. 20D*

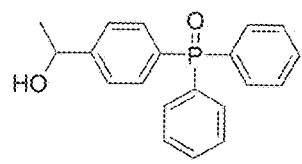
This H-Anchor molecule uses the H-Gap format, with the following parent structure:
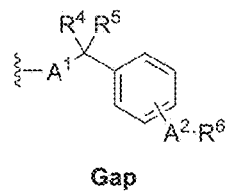
Gap
Wherein $A^1$ = O; $R^4$ = H; $R^5$ = -(CH$_2$)$_p$-Me where p = 0; $A^2$ = -(CH$_2$)$_k$- in the para position where k = 0; $R^6$ = Dpp
*FIG. 20E*

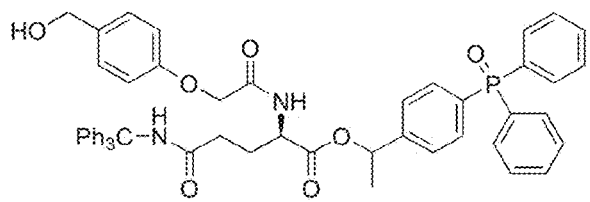
This H-Anchor molecule uses the H-Linker-Spacer-Gap format, with the following parent structures:
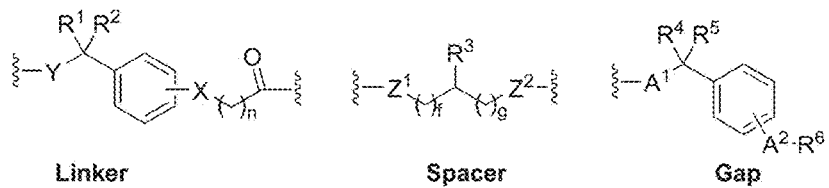
Where Y = O; $R^1$ = H; $R^2$ = H; X = O in the para position; n = 1; $Z^1$ = NH; f = 0; $R^3$ is as defined above where h = 2; g = 0; $Z^2$ = -C(O)-; $A^1$ = O; $R^4$ = H; $R^5$ = -$(CH_2)_p$-Me where p = 0; $A^2$ = -$(CH_2)_k$ - in the para position where k = 0; $R^6$ = Dpp; $R^3$ = 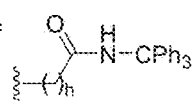
*FIG. 20F*

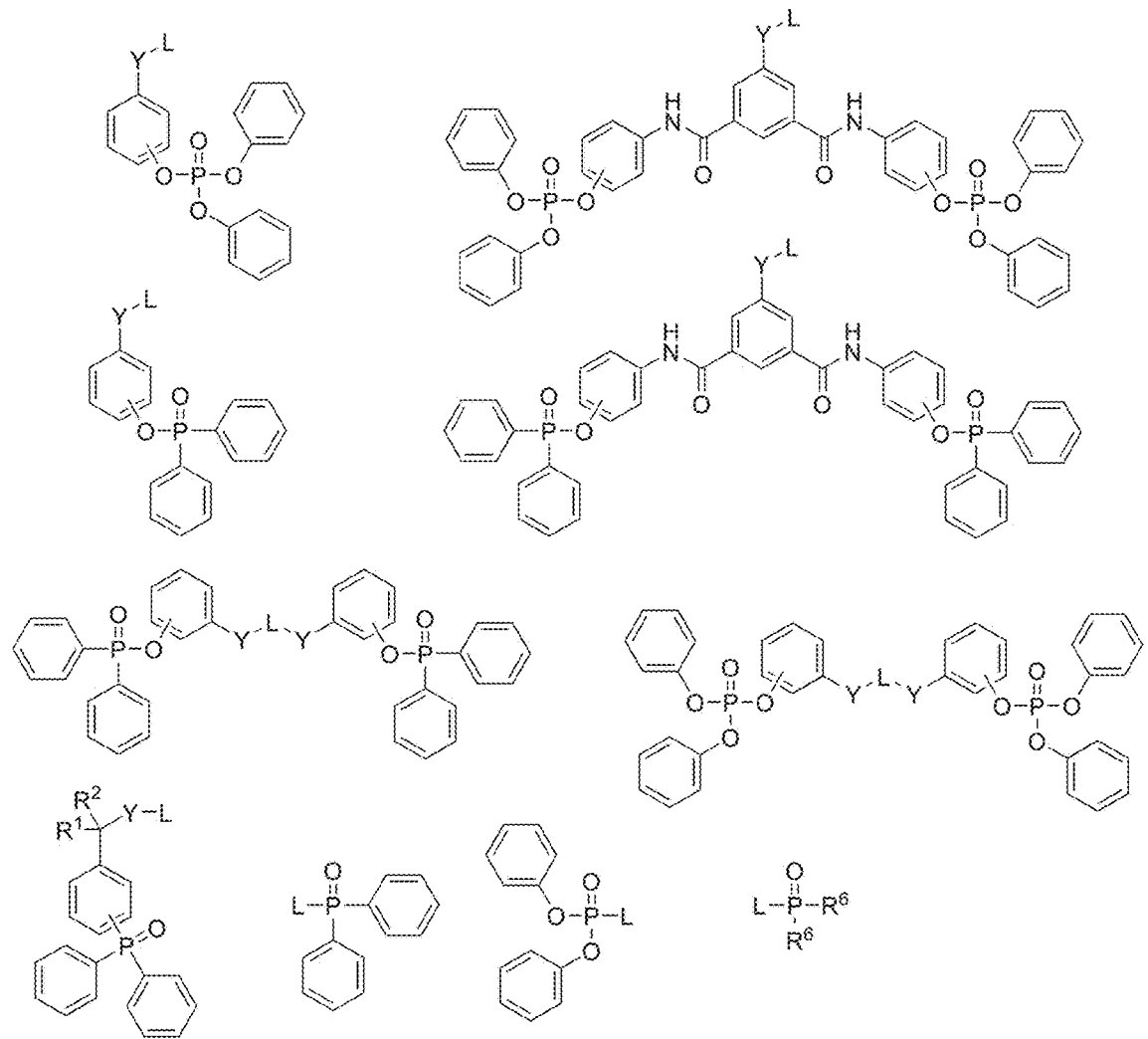

Wherein:
Y = S; O; NH; NMe; NEt; N-iPr
$R^1$ = H; -$(CH_2)_a$-H where "a" is any integer from 0 to 30; -$CCl_3$; -$CF_3$; phenyl; isopropyl; tert-butyl; chlorophenyl; dichlorophenyl; methoxyphenyl; or dimethoxyphenyl
$R^2$ = -$(CH_2)_b$-H where "b" is any integer from 1 to 30; -$CCl_3$; -$CF_3$; phenyl; isopropyl; tert-butyl; chlorophenyl; dichlorophenyl; methoxyphenyl; or dimethoxyphenyl
$R^6$ = $C_yH_{(2y+1)}$ where "y" is any integer from 1 to 30; $YC_yH_{(2y+1)}$ where "y" is any integer from 1 to 30 and Y is as defined above; (2-ethyl)hexyl; or isooctyl.
L is either hydrogen or chosen from the structures in FIG. 21B

*FIG.21A*

Wherein L =

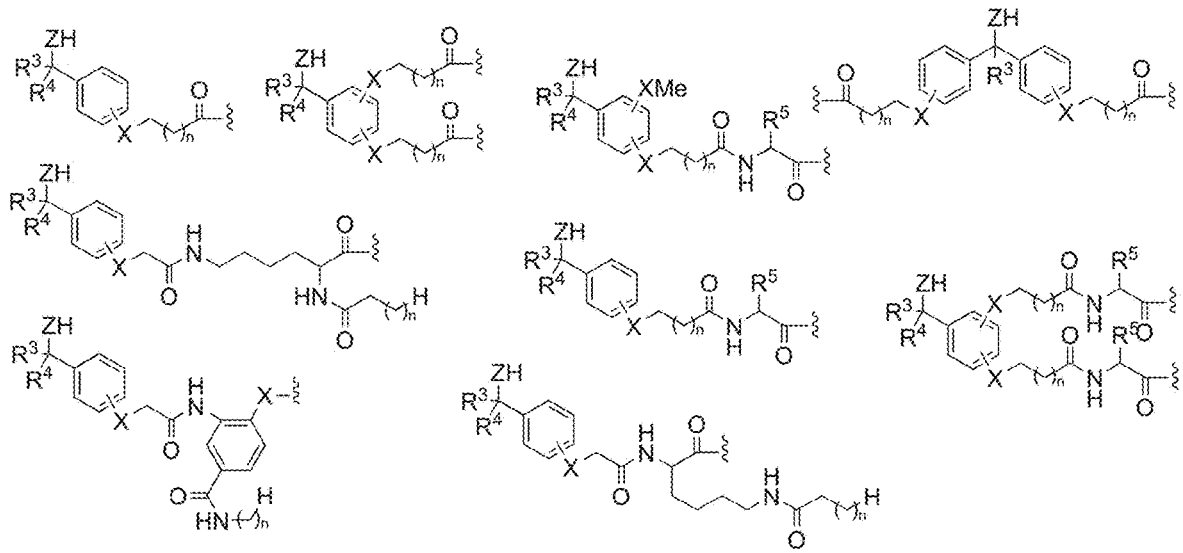

Wherein:

ZH is the attachment point of L to a target substrate

⸺ξ in the structures above is the attachment point of L to the molecuels in FIG. 21A Z = S; O; NH; NMe; NEt; N-iPr X = S; O; NH; NMe; NEt; N-iPr n = any integer from 0 to 30

$R^3$ = H; -$(CH_2)_c$-H where "c" is any integer from 0 to 30; -$CCl_3$; -$CF_3$; phenyl; isopropyl; tert-butyl; chlorophenyl; dichlorophenyl; methoxyphenyl; or dimethoxyphenyl $R^4$ = H; -$(CH_2)_d$-H where "d" is any integer from 0 to 30; -$CCl_3$; -$CF_3$; phenyl; isopropyl; tert-butyl; chlorophenyl; dichlorophenyl; methoxyphenyl; or dimethoxyphenyl $R^5$ is chosen from the structures below:

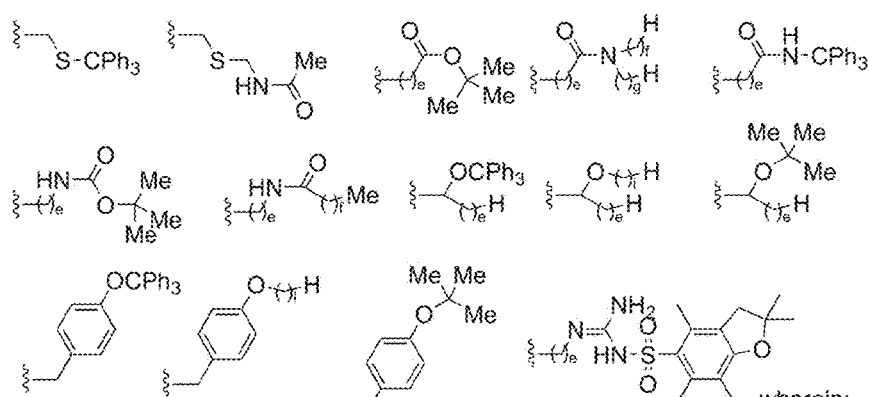

wherein:

⸺ξ is the attachment point of $R^5$ to L e = any integer from 0 to 30 f = any integer from 0 to 30 g = any integer from 0 to 30

*FIG. 21B*

COMPOSITIONS AND METHODS FOR CHEMICAL SYNTHESIS

CROSS-REFERENCE TO RELATED APPLICATIONS

Any and all applications for which a foreign or domestic priority claim is identified in the Application Data Sheet (either filed with the present application or subsequently amended) are hereby incorporated by reference under 37 CFR § 1.57. This application cross-references: i) PCT Application No. PCT/US16/68112, "System and method for solution phase GAP peptide synthesis," filed on 21 Dec. 2016; ii) PCT Application No. PCT/US19/29569, "Method for Solution-Phase Peptide Synthesis," filed Apr. 29, 2019; iii) PCT Application No. PCT/US19/33296, "Method for Solution-Phase Peptide Synthesis and Protecting Strategies Thereof," filed on May 21, 2019; and iv) PCT Application No. PCT/US20/15132, filed Jan. 26, 2020, and these applications are herein incorporated by reference as examples. This application claims priority to PCT/US19/33296, PCT/US20/15132, U.S. App. Ser. No. 62/678,564, and U.S. App. Ser. No. 62/800,142, which are herein incorporated by reference as examples.

STATEMENT OF FEDERALLY SPONSORED RESEARCH OR DEVELOPMENT

None.

REFERENCE TO A SEQUENCE LISTING, A TABLE, OR A COMPUTER LISTING COMPACT DISC APPENDIX

None.

BACKGROUND OF THE INVENTION

Recent research efforts have made significant advancements in the area of purification chemistry, focusing specifically on avoiding column chromatography and recrystallization. This research has been defined as Group-Assisted Purification (GAP) chemistry/technology as a chemistry for organic synthesis that avoids traditional purification methods such as chromatography and/or recrystallization by purposefully introducing a well-functionalized group in the starting material or in the newly generated product. These GAP groups can also often be used as protecting groups to prevent undesired side-reactions during the synthesis of target molecules. Such research has the potential to encompass the entire field of synthetic organic chemistry.

Protecting groups are found in almost every complex synthesis where multiple functional groups are present. In regards to GAP chemistry, an ideal example would be one in which a semi-permanent protecting group introduced needed solubility characteristics required for GAP. However, most traditional protecting groups are nonpolar, and therefore do not generate the required GAP solubility for most substrates. If a protecting group could be developed that generated adequate solubility control, then GAP chemistry could potentially be extended to all syntheses which require the use of that protecting group. Several approaches have been utilized. Published patent application WO 2014093723 A2, teaches the protection of imines with a GAP-equipped chiral auxiliary, then using these chiral, N-phosphonyl imines as electrophiles in asymmetric boron addition reactions. Purification was conducted via GAP processes. This work is valuable in that it provides facile access to chiral, α-boronic acid amines, which could potentially be used to synthesize novel amino acid derivatives, which could potentially be incorporated into novel peptide targets.

Effective protecting groups need to be robust to a wide variety of conditions and must be added and removed with high yield. Protecting groups are used extensively in peptide synthesis, either for solid or solution phase approaches. For traditional peptide synthesis protection strategies, one of the most commonly used strategies is Fmoc/tBu. U.S. Pat. No. 8,383,770 B2 teaches the use of the Fluorenylmethoxycarbonyl (Fmoc) and tert-Butyloxycarbonyl (Boc) N-terminus protecting groups in Solid-Phase Peptide Synthesis (SPPS). This technology is well known and widely applied in industry. The Fmoc group protects the N-terminus of amino acids to be added to the growing peptide, and tert-butyl (tBu) based groups protect the side chains of the same amino acids. The Fmoc group can be removed with a proper deprotection base while the tBu groups remain until acid-based global deprotection at the end of the synthesis. Boc and Fmoc groups have been used for decades in all areas of peptide chemistry, and the preferred Fmoc group is almost entirely restricted to SPPS.

Developed by Merrifield in the 1960s, SPPS has become a standard protocol used by multiple scientific disciplines for research and manufacturing (see FIG. 1A). The advantages of the polymer support or resin lie in its ability to allow facile purification of the growing peptide after each coupling/deprotection step, which avoids the use of column chromatography. The key disadvantage of SPPS lies in the difficulty of scale-up: many polymer supports are expensive and occupy the vast majority of the mass of the material to be worked with. Coupling reactions in SPPS are also inefficient because the reactions occur on a solid-liquid interface. Additionally, after each deprotection and coupling reaction, the resin must be washed with solvent to remove any impurities generated from previous reactions, and this generates significant solvent waste that can be extremely problematic on a large scale.

Examples of economically feasible Fmoc protection schemes for solution-phase peptide synthesis (SolPPS), however, are rare, with few examples in the literature at all. U.S. Pat. No. 5,516,891 A provides one of the few examples of Fmoc-based SolPPS. Again, the Fmoc peptide synthesis is almost entirely restricted to SPPS, due to the formation of N-fluorenylmethylpiperidine (NFMP) as a side product during deprotection, which is difficult to remove without polymer supports. The standard protocol for Fmoc deprotection is to stir the Fmoc-peptide in a solution of dimethylformamide (DMF) or dichloromethane (DCM) with excess piperidine, deprotecting the Fmoc group and forming NFMP in the process. The '891 patent teaches removal of this impurity by deprotecting with 4-aminomethylpiperidine (4AMP) instead of piperidine. This forms NFMP-$CH_2NH_2$ instead of NFMP, which due to the presence of the extra amino group, can be extracted into water. The problem with this method lies in the high cost of using 4AMP. This is why this method is cost prohibitive, and why it has not been accepted by the industry.

Another example of Fmoc-based SolPPS can be seen in published patent application WO2017112809A1. This publication teaches the use of a C-terminus GAP protecting group, benzyl diphenylphosphine oxide (HOBnDpp), to control the solubility of the target peptide to allow for selective precipitation after each successive coupling reaction (see FIG. 1B). The solubility is controlled such that the growing peptide remains in an organic solvent, such as ethyl acetate or DCM, and aqueous washes are performed to remove impurities; a subsequent concentration of the organic solvent followed by mixture in an alkane solvent selectively precipitates the peptide product. While this technology adapted Fmoc/tBu chemistry to solution-phase in a much more economically feasible manner than the '891 patent, there are potential limitations inherent in the method. First, the GAP group is not acid labile, preventing convenient one-step global deprotection with commonly used trifluoroacetic acid-based (TFA-based) or other acidic cocktails; hydrogenation or hydrolysis is required to remove HOBnDpp from the C-terminus of the peptide. Additionally, as the peptide continues to grow and change in sequence, HOBnDpp maintains less and less solubility control over the chain as it becomes longer, or as sequences lend different solubility characteristics to the peptide. HOBnDpp is also prone to hydrolysis or accidental cleavage during the synthesis. For example, during Fmoc deprotection of the second amino acid in the peptide sequence, diketopiperazine (DKP) formation facilitates the loss of HOBnDpp from the C-terminus. This cleaved HOBnDpp remains in the reaction solution and can react with activated amino acids during coupling reactions to generate impurities that are difficult or impossible to remove. Moreover, with the current cleavage techniques (either hydrolysis or hydrogenation) for deprotection of the C-terminus after the protected peptide is synthesized, the C-terminus of the final peptide product is a carboxylic acid. Many therapeutic peptides conversely require the C-terminus to be modified, such as into an amide, a cyclic peptide, a thioester, etc., in lieu of this carboxylic acid, further limiting the application of the GAP peptide synthesis method. Additionally, these cleavage reactions to remove HOBnDpp from the C-terminus are completely separate reactions from the global deprotection; the reactions require specific conditions and work ups, an inconvenience that costs both time and money.

Because of these and other issues with scale up in SPPS, as well as the limitations in the existing GAP peptide synthesis protection strategy, there is a need in the industry for not just SolPPS methods amenable to scale up, but SolPPS methods that are more amenable to (i) various cleavage conditions, (ii) longer or more difficult (from a solubility perspective) sequences, (iii) and C-terminus modification.

SUMMARY OF THE INVENTION

In one embodiment, the present disclosure can include a chemical composition comprising a GAP constituent, a spacer constituent, and a linker constituent, wherein the spacer constituent is disposed between the GAP constituent and the linker constituent.

In another embodiment, the present disclosure can include a method for synthesizing a peptide, the method comprising the steps of: coupling a first amino acid to an anchor molecule, wherein the anchor molecule comprises a GAP constituent and a linker constituent, and wherein the first amino acid is attached to the linker constituent of the anchor molecule; forming a peptide bond between a second amino acid and the first amino acid; and removing the anchor molecule from the first amino acid. In another embodiment, the present disclosure can include a method of forming a composition comprising a GAP anchor, the method comprising the steps of: providing a GAP constituent; and attaching the GAP constituent to a linker constituent.

In another embodiment, the present disclosure can include a method for synthesizing a peptide, the method comprising the steps of: coupling a GAP anchor to a first amino acid; forming a peptide bond between a second amino acid and the first amino acid; and removing the GAP anchor from the first amino acid; wherein the GAP anchor is selected from the group consisting of:

(Compound 1)

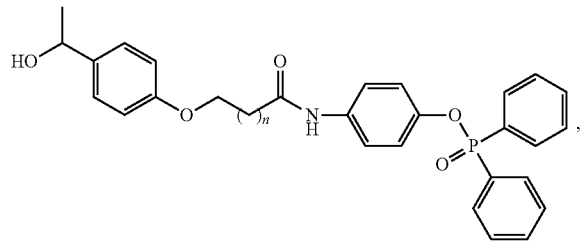

wherein n=2 or 9;

(Compound 2)

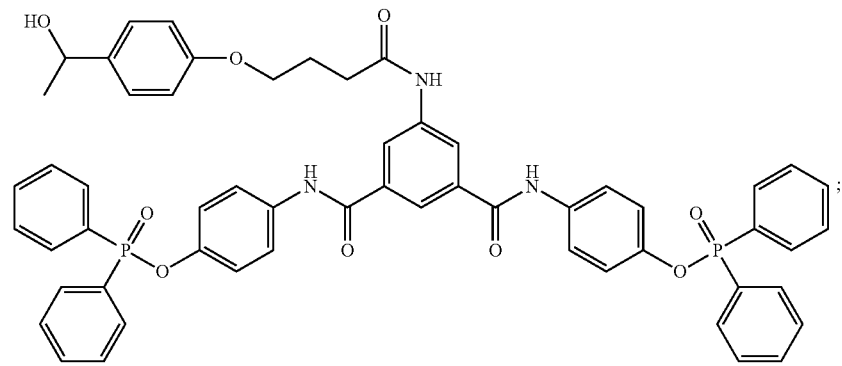

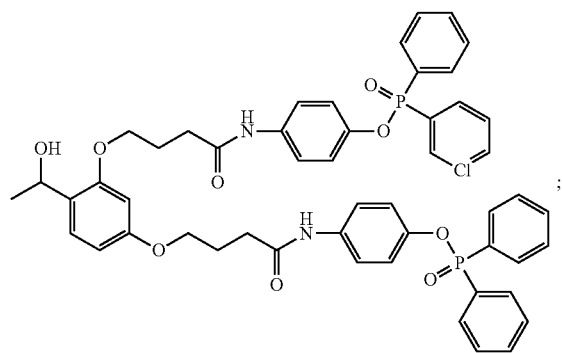
(Compound 3)
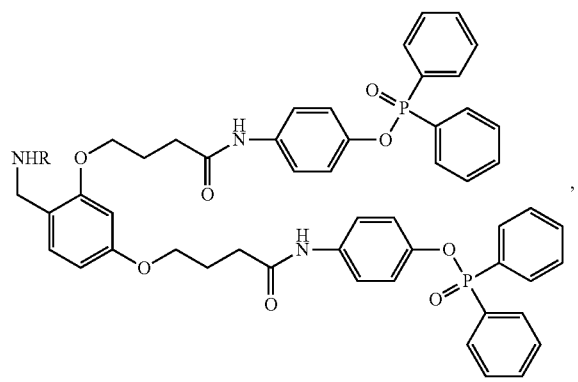
(Compound 4)
wherein R=H, Me, Et, or iPr;
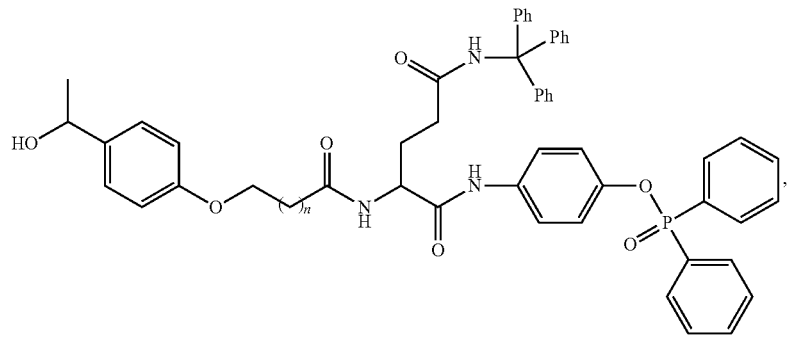
(Compound 5)
wherein n=0 or 2;
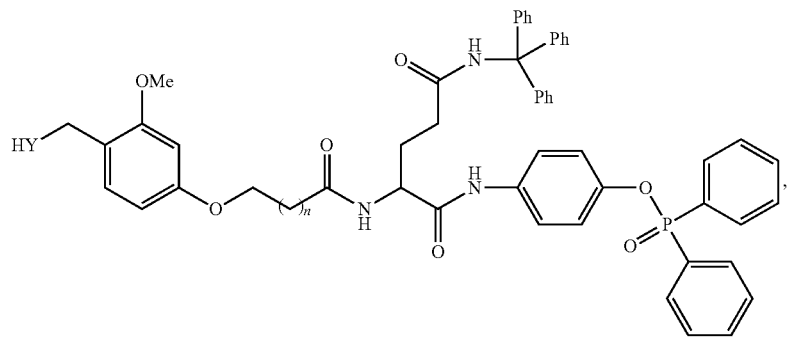
(Compound 6)
wherein n=0 or 2, and wherein Y=O, NMe, NEt, or N-iPr;

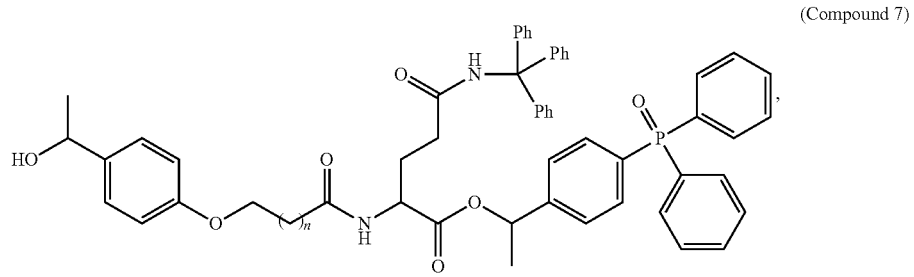
(Compound 7)
wherein n=0 or 2;
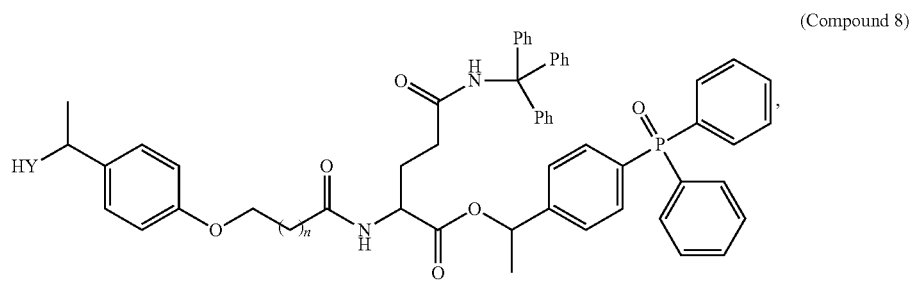
(Compound 8)
wherein n=0 or 2, and wherein Y=O, NMe, NEt, or N-iPr;
(Compound 9)
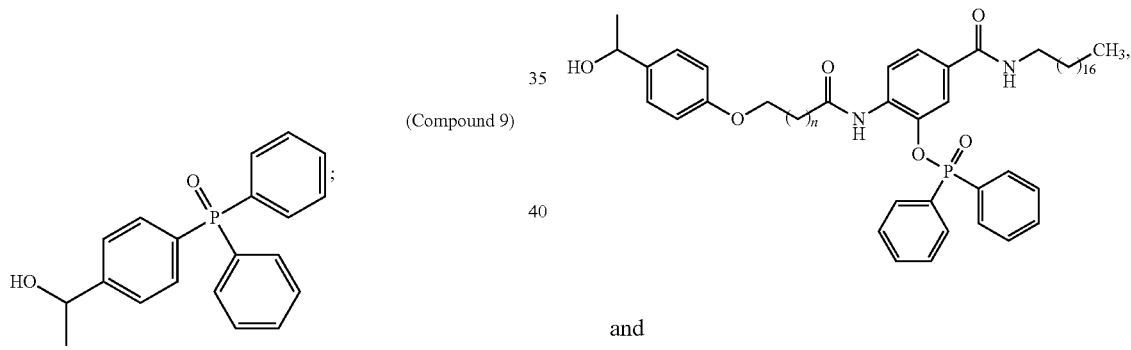
-continued
(Compound 10)
and
wherein n=0 or 2.
(Compound 11)
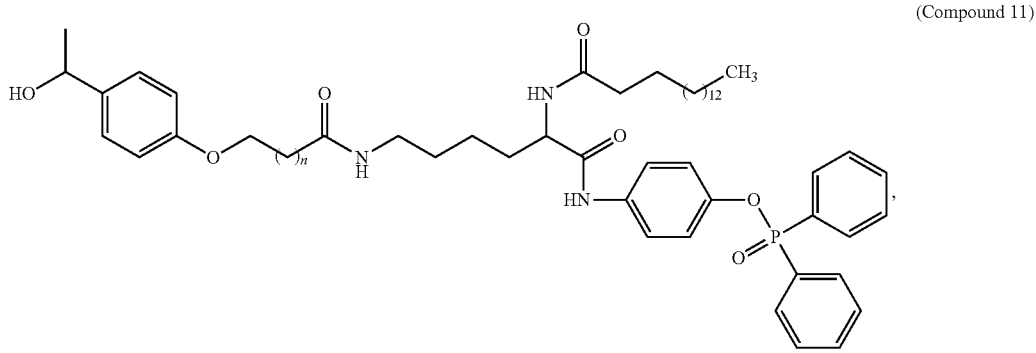
wherein n=0 or 2.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure. The figures are used as non-limiting examples, only intended to portray preferred embodiments without limiting the scope of this disclosure:

FIGS. 20A-20F show structures of H-Anchor molecules and Gap, Linker, and Spacer constituents thereof.

FIGS. 21A-21B depicts exemplary structures of GAP anchor or H-Anchor molecules in accordance with the present disclosure.

DETAILED DESCRIPTION OF THE DISCLOSURE

Figure 1A:
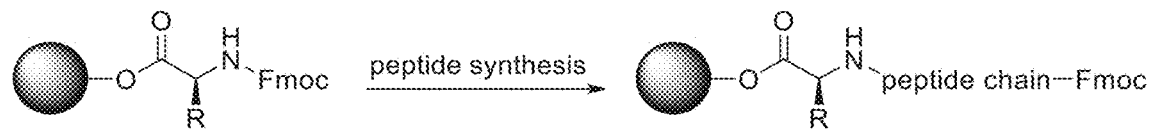
FIG. 1A depicts a prior art process of Solid Phase Peptide Synthesis (SPPS).

In the Summary of the Invention above and in the Detailed Description of the Invention, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference if made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(an initial number) to (a subsequent number)" or "(an initial number)–(a subsequent number)," this means a range whose lower limit is the initial number and whose upper limit is the subsequent number. For example, 25 to 100 mm means a range whose lower limit is 25 mm, and whose upper limit is 100 mm.

The term "first" is used to distinguish one element from another element and is not meant denote that an element is the primary or initial element in any given sequence of elements. For example, "a first amino acid" does not signify that the amino acid is the first in a sequence of amino acids or the first amino acid to be reacted. Instead, "a first amino acid" only indicates that the amino acid is separate and distinguishable from another amino acid, such as "a second amino acid."

The term "coupling reaction" is used to refer generally to the formation of a bond between two constituent molecules, which can be facilitated by a "coupling reagent." In peptide chemistry, these coupling reactions can occur via many different mechanisms under many different reaction conditions that can completely depend on the coupling reagent used. For example, a coupling reagent can "activate" the carboxylic acid of a constituent molecule such that the carbonyl carbon can be more prone to nucleophilic attack. Coupling reactions can result in the loss of a water molecule during the formation of the bond between the two constituent molecules.

In many types of protecting schemes for peptide synthesis, a repetition of similar reactions occurs to grow the peptide chain. Generally, either the N- or C-terminus of each amino acid added to the chain is initially protected, and the other terminus of the amino acid is free to participate in a coupling reaction. After addition to the chain via the initially-free terminus, a deprotection reaction is run, freeing up the protected N- or C-terminus to participate in a subsequent coupling reaction to create a peptide bond with the next amino acid. For example, in Fmoc/tBu-based peptide synthesis, the Fmoc group protects the N-terminus of amino acids, and side chains of amino acids are protected with tBu-based protecting groups, including but not limited to butyl, trityl (triphenylmethyl), Boc (butyloxycarbonyl), Pbf (2,2,4,6,7-pentamethyl-2,3-dihydrobenzofuran-5-sulfonyl), Pmc (2,2,5,7,8-pentamethylchromane-6-sulfonyl), and Acm (acetamidomethyl) (some amino acids do not require side-chain protection because the side-chains are naturally inert to coupling and deprotection conditions). The C-terminus of the primary amino acid in the peptide sequence is connected to and protected by a resin or polymer in SPPS, and a protecting group in SolPPS. The Fmoc/tBu peptide synthesis scheme is designed such that the Fmoc group on the N-termini of amino acids is base-labile, and treatment with the proper deprotection base removes the Fmoc group from the N-termini without interfering with any C-terminus connections or side-chain protections. Once the deprotection reaction is performed, the N-terminus of the primary amino acid is free, while the C-terminus and side chain are protected or otherwise inert. Then, the next amino acid, with the N-terminus Fmoc-protected and the side chain protected or naturally inert, is activated at the free C-terminus with a coupling reagent, and such activation facilitates nucleophilic attack by the free N-terminus of the primary amino acid on the activated carbonyl to form a peptide bond between the primary and next amino acid. This process is repeated until the proper peptide sequence is achieved. After Fmoc deprotection of the final amino acid, the peptide is still protected at the C-terminus and at the side chains. A global deprotection with a strong acid cocktail such as a TFA-based cocktail is then performed to remove all of the side-chain protecting groups; in some cases, the C-terminal resin or protecting group can also be cleaved.

The present disclosure addresses failings in the art by providing a method for solution-phase peptide synthesis that allows for various global deprotection strategies, the synthesis of longer or more difficult (solubility-wise) peptide sequences, and C-terminus modifications on target peptides while maintaining solubility control of the target peptide and overall synthesis process. By utilizing novel protection strategies on the C-terminus and side chains of the growing peptide, a SolPPS strategy is presented that is economically feasible and useful for the commercial production of peptides.

It is therefore a non-limiting object of the present disclosure to enable a novel method of SolPPS. In one aspect, HOBnDpp, traditionally a C-terminus GAP protecting group, is used to directly protect the side chains of amino acid residues, including, but not limited to, serine, threonine, tyrosine, or cysteine, in lieu of or in addition to the C-terminus of the peptide chain. The other amino acid residues of the desired peptide can be protected using a number of different protection strategies, including, but not limited to, Fmoc/tBu, Boc/benzyl, Cbz (benzyloxycarbonyl)/tBu, Cbz/benzyl, etc. This enhanced protection strategy allows for the synthesis of longer and/or more difficult sequences while maintaining solubility control of the peptide chain. This strategy also enables the use of different C-terminus protecting groups for solubility, deprotection, or post-synthesis C-terminus modification purposes. In another aspect, novel GAP molecules as discussed below are used to protect the C-terminus and/or side chains of certain amino acids to allow for peptide synthesis in solution in the C to N direction.

In another aspect, a novel SolPPS method is accomplished through specially designed C-terminal protecting strategies, wherein novel GAP molecule protecting groups maintain benefits of original GAP peptide synthesis (GAP-PS) while allowing for a wider range of cleavage conditions, the synthesis of longer peptides, minimized unintentional or accidental deprotection, and C-terminal modifications upon cleavage. Depending on the GAP molecule used, C-terminus deprotection can be accomplished under either acidic conditions, including but not limited to treatment with trifluoroacetic acid (TFA), hydrofluoric acid (HF), toluenesulfonic acid (TsOH), methanesulfonic aicd (MsOH) or others, as well as basic hydrolysis conditions, including but not limited to metal hydroxides in either aqueous or alcoholic systems, or bi-phasic systems with phase-transfer catalysts, as well as reductive conditions, including but not limited to molecular hydrogen over transition metal catalysts such at $Pd^0$ or $Pt^0$ or Ru, transfer hydrogenation, or other hydrogen sources such as borohydrides, aluminum hydrides, silanes, ammonium formate, etc. Also depending on the specific GAP molecule, C-terminus amide formation or other post-synthesis modifications can be accomplished during the cleavage of the C-terminus GAP molecule, generating desired peptide products while avoiding extra post-synthesis processing steps. These novel GAP molecules can remain stable to acid-catalyzed deprotection reactions, as well as hydrogenation-based and hydrolysis reactions, allowing for increased post-peptide-synthesis recovery of the GAP protecting groups. Additionally, loss of C-terminal protection mid-synthesis is also minimized by these novel GAP molecules.

In another aspect, any of the novel GAP molecules described above are used to protect the side chains of various amino acids, including, but not limited to, aspartic acid, cysteine, serine, threonine, lysine, glutamic acid, asparagine, and glutamine, in lieu of or in addition to the C-terminus of the peptide. This strategy allows for the protection of reactive side chains while simultaneously controlling the solubility of the target peptide.

In another aspect, methods of synthesizing these novel GAP molecules and derivatives thereof are presented. As a non-limiting example, HOBnDpp is attached to carboxylic acid moiety of a linker molecule, examples of which can be seen in FIG. 18, either directly or through an intermediary, and a resulting novel GAP protecting group is then attached to the C-terminus of the peptide. As another non-limiting example, aniline diphenylphosphine oxide (i.e. $NH_2PhDpp$), is coupled to different linkers in a similar manner to achieve novel GAP protecting groups that can be used in a similar manner.

In another aspect, any of these different strategies discussed above are utilized in different combinations to enable the best possible synthesis strategy for a given peptide. As a non-limiting example, when used appropriately, these strategies allow for the synthesis of longer peptides entirely in solution, with C-terminus deprotection and C-terminus amide formation being accomplished along with side chain deprotection in a one-step reaction.

It is therefore a non-limiting object of the present disclosure to provide a method for SolPPS. In designing this method, it was apparent that the method should seek to maintain the advantages of other solution-phase methods like GAP-PS, such as avoiding arduous distillation and purification strategies that hinder large scale productions. An enhanced protection strategy would need to be designed to maintain solubility control of the target peptide to allow separation of the product from generated amino acid and deprotection protocol impurities, while also addressing the shortcomings in the art.

Figure 1B:
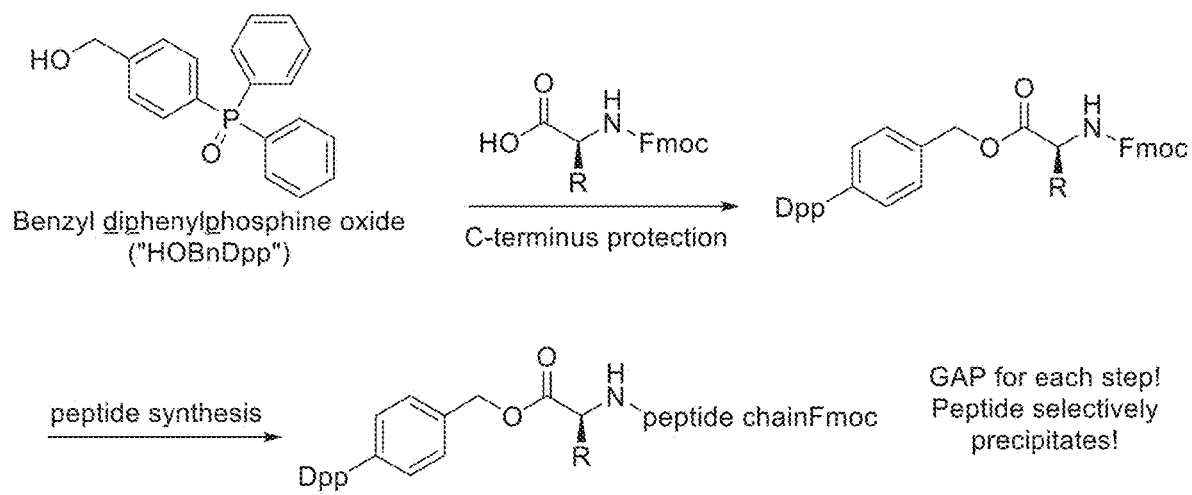
FIG. 1B depicts steps of the GAP Peptide Synthesis (GAP-PS) process, specifically the use of a HOBnDpp for C-terminus protection.
Figure 2:
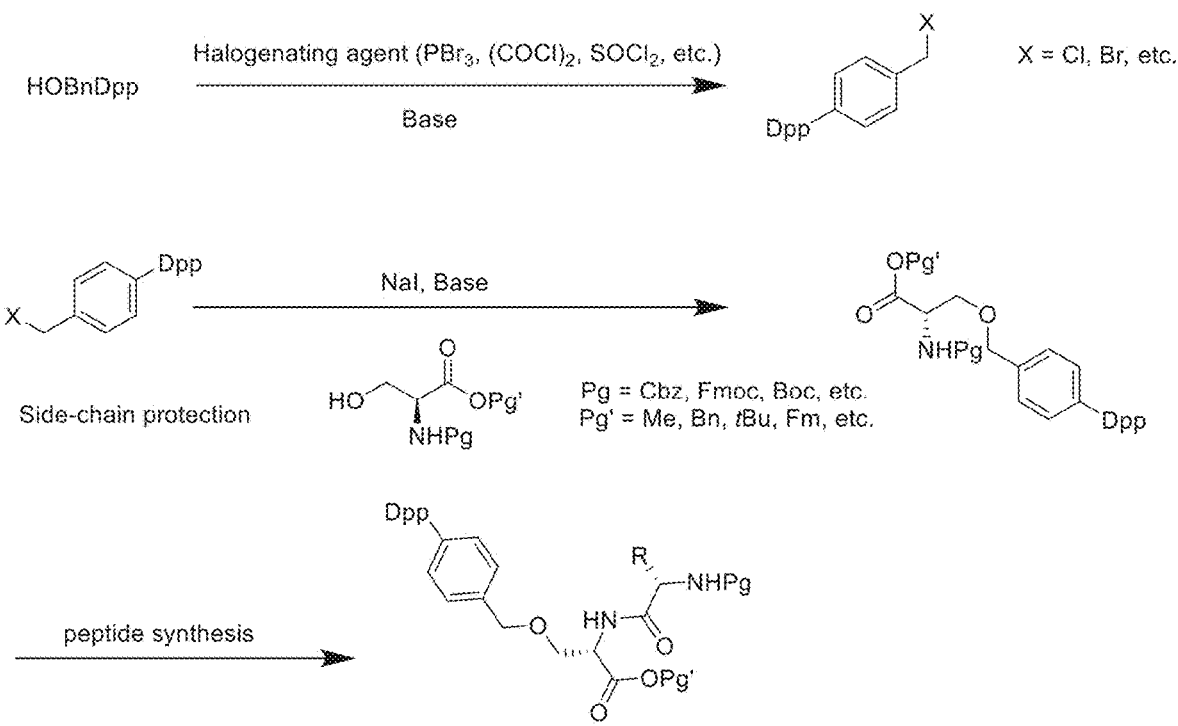
FIG. 2 depicts a process for attaching the protecting group of FIG. 1B to the side chain of an amino acid residue, specifically serine in this non-limiting embodiment, followed by GAP-PS.

In a non-limiting exemplary embodiment of the present disclosure, a novel SolPPS method can begin with attachment of HOBnDpp directly to the C-terminus of the primary amino acid in a given sequence (see FIG. 1B). Alternatively, or in addition, to protecting the C-terminus of a primary amino acid with HOBnDpp, attachment of HOBnDpp to side chains of amino acid residues, such as, but not limited to, serine, threonine, tyrosine, and/or cysteine, with subsequent incorporation into the growing peptide, can also be executed to better control solubility and protect the side chains of certain amino acids (see FIG. 2). To accomplish side-chain protection with HOBnDpp, HOBnDpp is initially reacted with a halogenating agent (for example, $PBr_3$, $POBr_3$, $(COCl)_2$, $SOCl_2$, etc.) in the presence of a base (for example, triethylamine, diisopropylethylamine, sodium bicarbonate, etc) to provide either IBnDpp, ClBnDpp or BrBnDpp, depending on the halogenating reagent used. The reaction can occur at a range of conditions depending on the halogenating agent and base used for the reaction. As an example, the reaction can be conducted at a pressure from 1 to 100 bar, at a temperature from $-78°$ C. to $100°$ C., and in mono-phasic or bi-phasic reaction medium. This halogenated compound can then be reacted with an amino acid with a primary protecting group (Pg) on the N-terminus and a secondary protecting group (Pg') on the C-terminus to effectively protect the side chain of the amino acid. Peptide synthesis can then be run in the C to N direction if a GAP molecule protects the C-terminus of the peptide in lieu of or in addition to GAP protection of the side chain of one or multiple amino acids to be integrated into the peptide sequence; alternatively, peptide synthesis can be run or in the N to C direction if HOBnDpp or other GAP molecule only protects an amino acid side chain. A myriad of protecting strategies for N-terminus and side-chain protection can be possible. Potential N-terminus or C-terminus protecting groups can include, but are not limited to, Cbz, Fmoc, Boc, methyl, Bn (benzyl), or any of the GAP molecules discussed herein, and side chain protecting groups can include, but are not limited to, tBu, Acm, Trityl, Boc, Pbf, Pmc, Fm (fluorenylmethyl), and any of the GAP molecules discussed herein.

Figure 3:
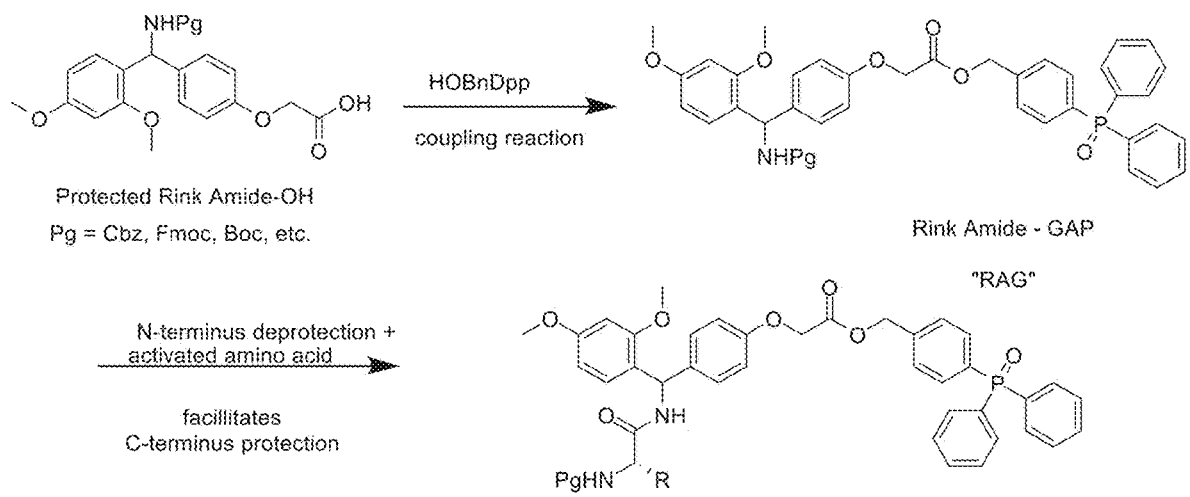
FIG. 3 depicts a schematic for synthesizing, as an example, a novel GAP molecule and attaching it to a peptide, wherein HOBnDpp is reacted with protected Rink Amide-OH and the resulting new chemical entity Rink Amide-GAP (RAG) is attached to the C-terminus of an amino acid.
Figure 4:
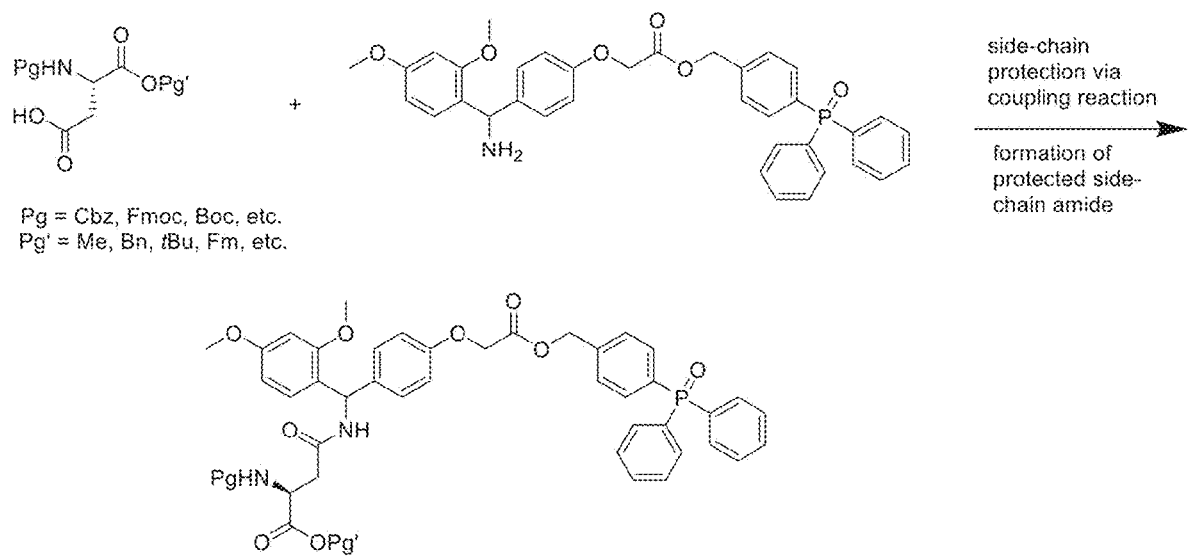
FIG. 4 depicts the attachment of a novel GAP molecule to the side chain of an amino acid. In this non-limiting example, the GAP molecule RAG is used to protect the side chain of aspartic acid, resulting in synthesis of RAG-protected asparagine. Specifically, a coupling reaction is performed to form an amide bond between the free amine on the RAG molecule and the carbonyl carbon of asparagine.

In another non-limiting exemplary embodiment, a novel SolPPS method can begin with a novel GAP molecule (here, RAG) being used for C-terminus protection as seen in FIG. 3, enabling both acid-labile C-terminus protection of the peptide and C-terminus amide formation upon cleavage of RAG from the peptide. Once C-terminal protection with RAG is accomplished, peptide synthesis can run in the C to N direction, utilizing a myriad of N-terminus and side-chain protection strategies, such as, but not limited to, the Fmoc/tBu strategy. To synthesize RAG, HOBnDpp can be coupled to protected Rink Amide-OH via a multitude of coupling reagents, such as, but not limited to, TFFH ("N-((dimethylamino)fluoromethylene)-N-methylmethanaminium hexafluorophosphate"), TBTU ("1-((dimethylamino)(dimethyliminio)methyl)-1H-benzo[d][1,2,3]triazole 3-oxide tetrafluoroborate"), HBTU ("1-((dimethylamino)(dimethyliminio)methyl)-1H-benzo[d][1,2,3]triazole 3-oxide hexafluorophosphate"), EDCI ("3-(((ethylimino)methylene)amino)-N,N-dimethylpropan-1-amine"), or COMU ("(1-Cyano-2-ethoxy-2-oxoethylidenaminooxy)dimethylamino-morpholino-carbenium hexafluorophosphate") to provide the GAP molecule RAG. The coupling reaction can occur at a range of conditions depending on the specific coupling reagent used. As an example, the reaction can be conducted at atmospheric pressure at room temperature with light stirring with TBTU. Once the protected RAG molecule is synthesized, a deprotection reaction can occur (for example, an Fmoc deprotection reaction) to free up the amine on the Rink Amide to participate in a coupling reaction to a carboxylic acid, such as can be found at the C-terminus of an amino acid. RAG can alternatively or additionally be attached to the side chains of amino acid residues, including, but not limited to, aspartic acid and glutamic acid (see FIG. 4) to allow for enhanced protection or solubility control upon the addition of those amino acids to the growing sequence. Upon cleavage of RAG from the side chains of amino acids, amide-forms of those side chains (here, asparagine and glutamine, respectively) can be generated (see FIG. 4).

In another non-limiting exemplary embodiment, a novel SolPPS method can begin with a novel GAP molecule (here, (Rink Amide)-phenylalanine-GAP, i.e. RPG) being used for C-terminus protection. RPG can be synthesized similarly to FIG. 5. Specifically, HOBnDpp may be coupled to Fmoc-protected phenylalanine to form Fmoc-phenylalanine-GAP (i.e. Fmoc-F-GAP), and after Fmoc deprotection, the now-free N-terminus of GAP-protected phenylalanine may be coupled the carboxylic acid moiety of protected Rink Amide-OH (the molecular structure of protected Rink Amide-OH may be seen in FIG. 3). The resulting structure can then be deprotected at the N-terminus of the Rink Amide molecule, and the free N-terminus can then participate in a coupling reaction to form a peptide bond with the primary amino acid in a given peptide sequence. Peptide synthesis can then proceed in the C to N direction with RPG providing C-terminus protection of the growing peptide. RPG as a C-terminal protecting group can be used in conjunction with any of the disclosed GAP molecules that provide side-chain protection, or with any other protecting strategies available for N-terminus and side-chain protection. RPG can also be used to protect the side chains of amino acids just as RAG is used, either in addition to or in lieu of C-terminal protection.

In another non-limiting example, a novel SolPPS method can utilize a different novel GAP molecule, such as HG or HPG, for C-terminus protection. Synthesis of these GAP molecules can be seen in FIG. 5, and these molecules can be attached to the C-terminus of a peptide to allow for acid-labile C-terminus protection without C-terminus amide formation upon cleavage (see FIG. 6). In lieu of or in addition to protecting the C-terminus of amino acids, HG and/or HPG can also be attached to the side chains of amino acid residues, including, but not limited to, aspartic acid, cysteine, serine, threonine, tyrosine, and glutamic acid, to assist in solubility control (see FIG. 6). Peptide synthesis can then proceed in the C to N direction utilizing a myriad of protection strategies, such as, but not limited to, the Fmoc/tBu strategy.

Figure 6:
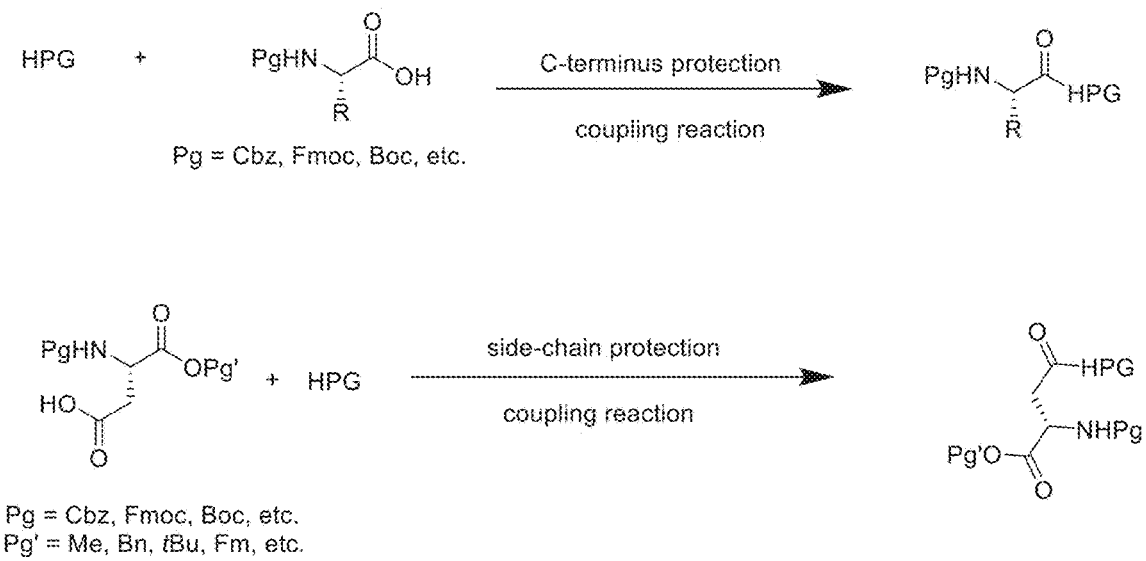
FIG. 6 depicts the attachment of HPG from FIG. 5 to the C-terminus of a generic amino acid, as well as to, in a preferred embodiment of this disclosure, the side chain of aspartic acid. Specifically, this reaction is a coupling reaction that can be accomplished through the use of multiple different coupling reagents, wherein the free alcohol of HPG couples to the carbonyl group of an activated carboxylic acid.
Figure 7:
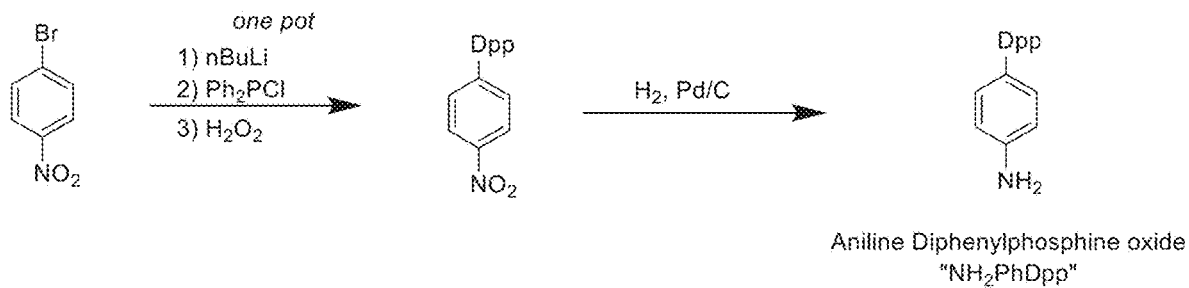
FIG. 7 depicts a non-limiting example of the synthesis of a novel GAP molecule, aniline diphenylphosphine oxide ("NH$_2$PhDpp").

In another non-limiting exemplary embodiment, a novel SolPPS method can begin with the synthesis of aniline diphenylphosphine oxide (i.e. $NH_2PhDpp$) as seen in FIG. 7. Specifically, synthesis of $NH_2PhDpp$ begins with 4-bromonitrobenzene, which can be activated N-butyllithium (nBuLi) in ethereal solvent at ultra-low temperature ($-100$ to $-30°$ C.) and room pressure to form an organolithium reagent. This reagent can then react in-situ with a slow addition of chlorodiphenyl phosphine which, after phosphine oxidation with hydrogen peroxide and nitro group reduction with $H_2$ and 10% Pd/C, will afford $NH_2PhDpp$. This molecule can then be attached, in a non-limiting example, to Rink Amide-OH (see FIGS. 8, 18), and the resulting GAP molecule can be attached to the C-terminus of a peptide similarly to FIG. 3 and/or the side chains of aspartic acid or glutamic acid (creating protected asparagine or glutamine, respectively) similarly to FIG. 4. In another non-limiting example, another novel GAP molecule can be synthesized via reaction of $NH_2PhDpp$ with the carboxylic acid moiety of a linker (here, HMPA) either directly or through an amine-based intermediary as seen in FIG. 9. The resulting GAP molecule can then be attached to the C-terminus of the peptide and/or to the side chains of aspartic acid, cysteine, serine, threonine, and glutamic acid as seen in FIG. 6. Peptide synthesis can then proceed in the C to N direction utilizing a myriad of protection strategies, such as, but not limited to, the Fmoc/tBu strategy.

For all of the above non-limiting examples, HOBnDpp, $NH_2PhDpp$, or any other GAP molecule can be attached to the C-termini or to the side chains of amino acid residues in a number of different solvents, including, but not limited to, dichloromethane, ethyl acetate, isopropyl acetate, methyltetrahydrofuran, tetrahyrdrofuran, and propylene carbonate. For any of the coupling reactions described herein, whether for GAP molecule synthesis or attachment of a GAP molecule to an initial amino acid of a peptide to be synthesized, a myriad of different coupling reagents can be used, including, but not limited to, TFFH, TBTU, HBTU, COMU, or EDCI.

As a non-limiting exemplary embodiment, and with any of the above discussed examples or any combinations thereof, SolPPS can then be accomplished in the C to N direction, such as with Fmoc/tBu chemistry. Deprotection of the Fmoc group for the primary and subsequent amino acids can be carried out with a myriad of deprotection reagents, including diethylamine, DBU (diazabicycloundecene), piperidine, tertybutylamine, and other alkyl amines, and additional coupling reactions can be performed to grow the peptide chain. After each coupling reaction, different quenching agents can be used to nullify excess activated amino acids and lend desired solubility characteristics to the resulting molecule. In a non-limiting example, decylamine can be used to quench activated amino acid and increase the resulting molecule's solubility in alkane solvents. Subsequently, depending on the reaction solvent, liquid-liquid extraction techniques or selective precipitation can be performed to purify the reaction mixture. The novel GAP molecules disclosed herein allow for solubility control and enable a novel SolPPS method, wherein selective precipitation or extraction effectively removes amino acid and fulvene impurities (i.e., NFMP). After the last amino acid of the desired peptide sequence is coupled, in a non-limiting example, global deprotection with an appropriate TFA cocktail can be performed to remove the acid-labile GAP molecules from the C-terminus and appropriate side chains; such deprotection can also remove other acid-labile side-chain protecting groups, such as tBu-based side-chain protecting groups. This novel SolPPS method enables a one-step global deprotection to yield the native peptide sequence, avoiding additional reactions like hydrogenation or hydrolysis to remove the C-terminal protecting group. Additionally, if a GAP molecule such as RAG is used, the C-terminal amide can be formed during the TFA cleavage, successfully avoiding post-synthesis reactions that would normally be required for such modification. These novel GAP molecules disclosed herein additionally remain stable during peptide synthesis, with no accidental hydrolysis or removal due to DKP formation.

Figure 17:
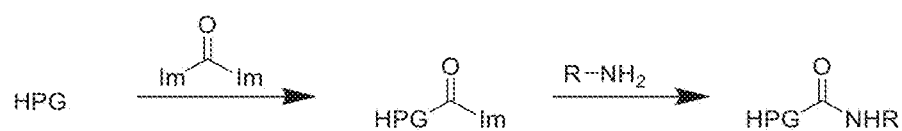
FIG. 17 shows a general methodology for protecting amines with novel GAP molecules. In this particular non-limiting embodiment, HPG is used.

In one non-limiting embodiment, these novel GAP molecules can be used to protect the N-terminus of any given peptide, as well as the amine-based side chains of certain amino acid residues, including, but not limited to, lysine. In a non-limiting example, HPG and diimidazole carbonyl are dissolved in an appropriate reaction solvent, such as DCM, and lightly stirred at room temperature and pressure for one hour or more. An amine is then added to the reaction mixture at room temperature and pressure to yield an HPG-protected carbamate product (see FIG. 17).

Figure 5:
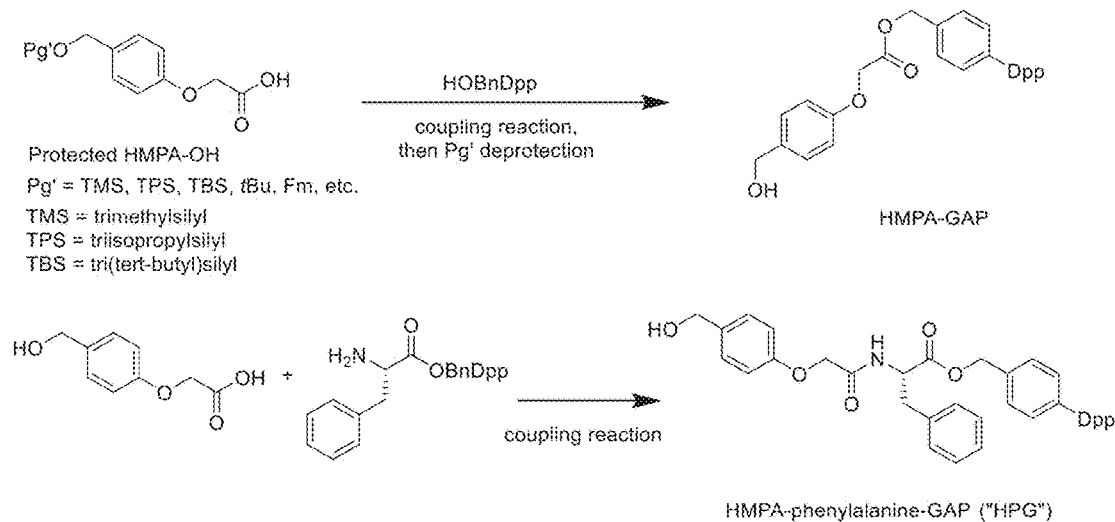
FIG. 5 depicts a non-limiting example of the synthesis of a novel GAP molecule. In this non-limiting example, HOBnDpp is connected to protected HMPA-OH directly to form HMPA-GAP (HG), as well as through an intermediary (phenylalanine in one embodiment) to form the GAP molecule, HMPA-phenylalanine-GAP (HPG). Specifically, HOBnDpp can be coupled to the carboxylic acid moiety of protected HMPA-OH, or HOBnDpp can be coupled initially to an amino acid followed by coupling to HMPA to create the GAP molecule HPG.
Figure 8:
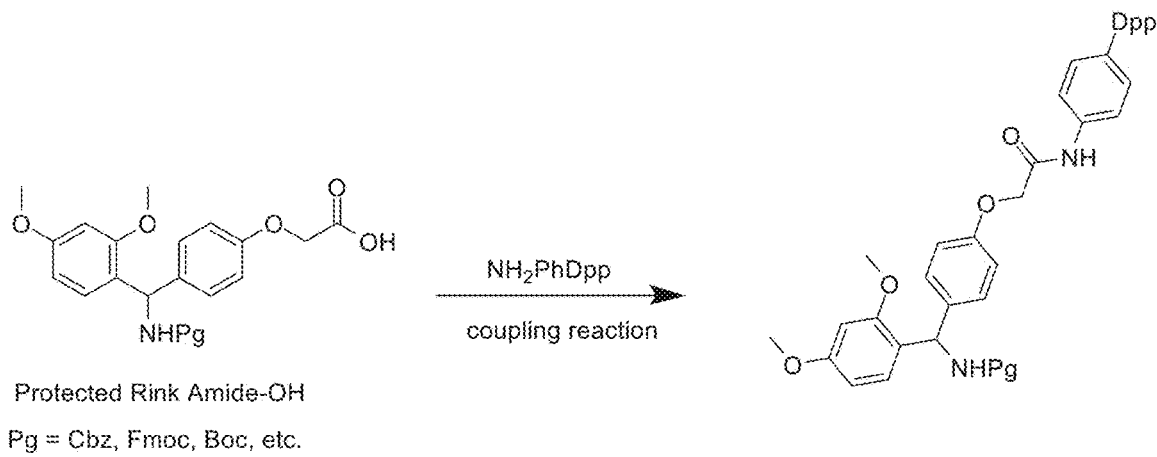
FIG. 8 depicts a non-limiting example of the synthesis of a novel GAP molecule, wherein NH$_2$PhDpp is reacted with protected Rink Amide-OH to achieve the target entity. Specifically, NH$_2$PhDpp can be coupled to the carboxylic acid moiety of protected Rink Amide-OH via a multitude of coupling reagents.
Figure 9:
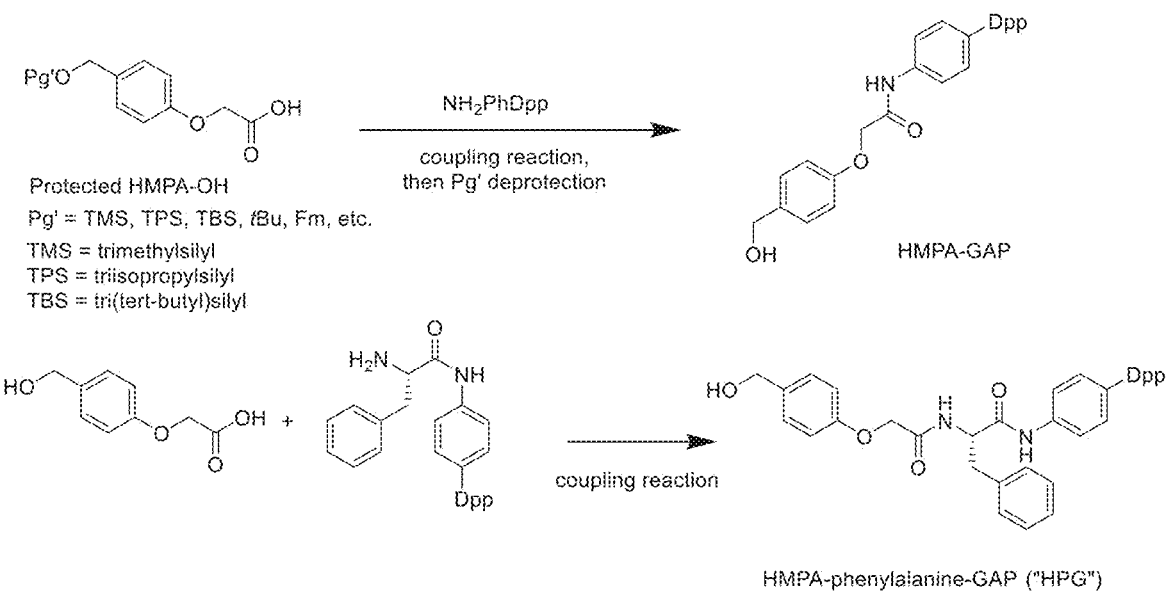
FIG. 9 depicts non-limiting examples of the synthesis of a novel GAP molecule, wherein NH$_2$PhDpp is reacted with protected HMPA-OH, either directly or through an intermediary, to form the target molecule. Multiple different coupling reagents can be used to facilitate these reactions.
Figure 18:
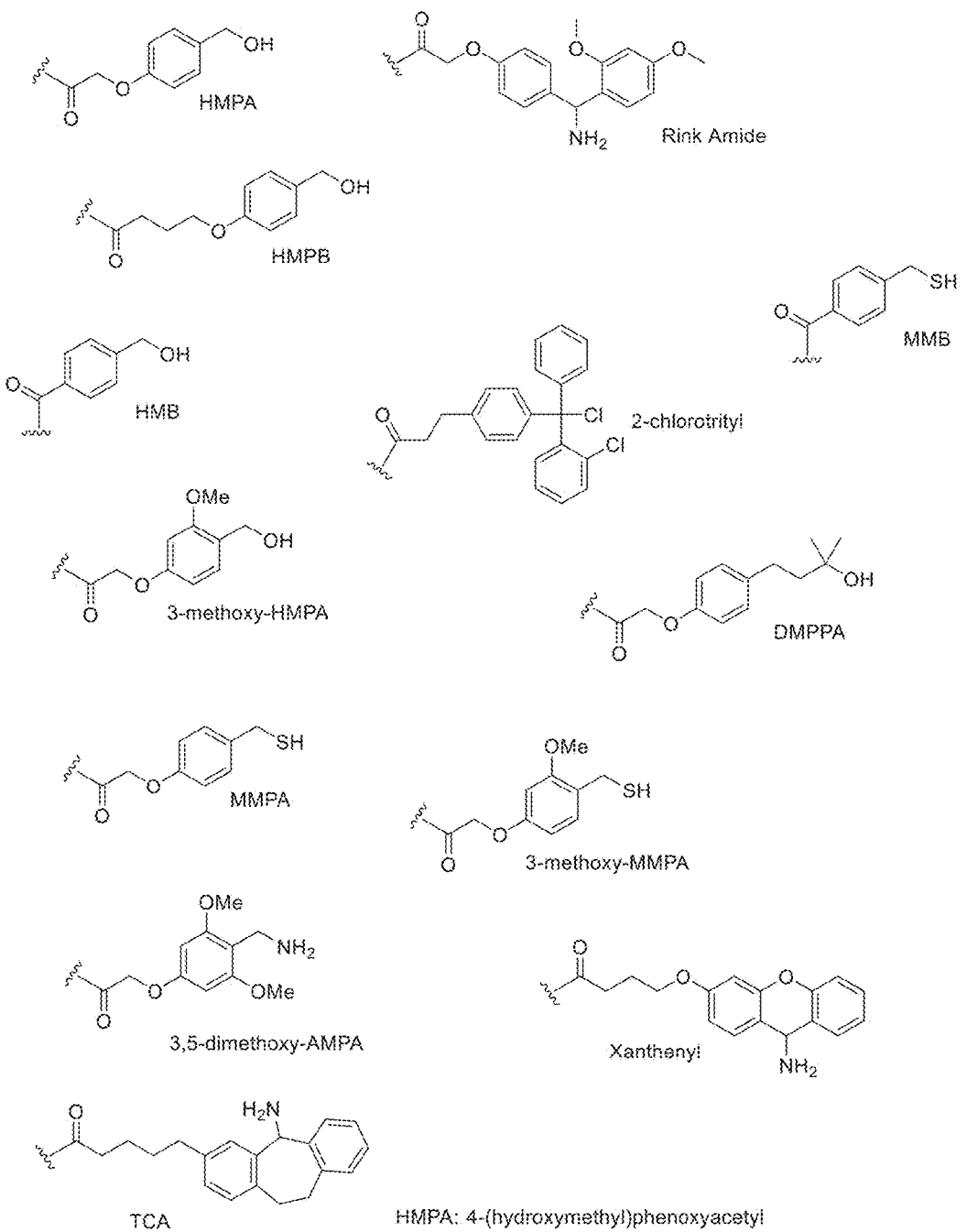
FIG. 18 shows as non-limiting examples a myriad of molecules that can serve as reagents for the synthesis of novel GAP molecules disclosed herein.

It another non-limiting embodiment, a novel SolPPS method can begin with the synthesis of novel GAP molecule protecting groups, wherein HOBnDpp, NH$_2$PhDpp, or a derivative thereof can be directly reacted with the carboxylic acid moiety of any given linker molecule, examples of which can be seen in FIG. 18, and in the table below:

HMPA: 4-(hydroxymethyl)phenoxyacetyl
HMPB: 4-(hydroxymethyl)phenoxybutanoyl
HMB: 4-(hydroxymethyl)benzoyl
MMB: 4-(mercaptomethyl)benzoyl
MMPA: 4-(mercaptomethyl)phenoxyacetyl
AMPA: 4-(aminomethyl)phenoxyacetyl
DMPPA: 4-(3,3-dimethyl-3-hydroxypropyl)phenoxyacetyl
Rink Amide: 2-(4-(amino(2,4-dimethoxyphenyl)methyl)phenoxy)acetyl
Xanthenyl: 4-((9-amino-9H-xanthen-3-yl)oxy)butanoyl
TCA: 5-(5-amino-10,11-dihydro-5H-dibenzo[a,d][7]annulen-3-yl)pentanoyl
2-Chlorotrityl: 3-(4-(chloro(2-chlorophenyl)(phenyl)methyl)phenyl)propanoyl An example of such reaction can be seen in FIGS. 3, 8, 9. These resulting GAP molecules can then be attached to any given amino acid to facilitate C terminus protection (as in FIG. 3), side-chain protection (as in FIG. 4), or N-terminus protection (a similar reaction as that seen in FIG. 17). In another non-limiting example, novel GAP molecules can be synthesized by reacting HOBnDpp or a derivative thereof with any given amino acid, followed by reacting with any given linker molecule at the carboxylic acid moiety as can be seen in FIGS. 5 and 9. The resulting GAP molecule can be used for C terminus protection (as in FIG. 3), side-chain protection (as in FIG. 4), or N-terminus protection (similarly to FIG. 17).

Figure 10:
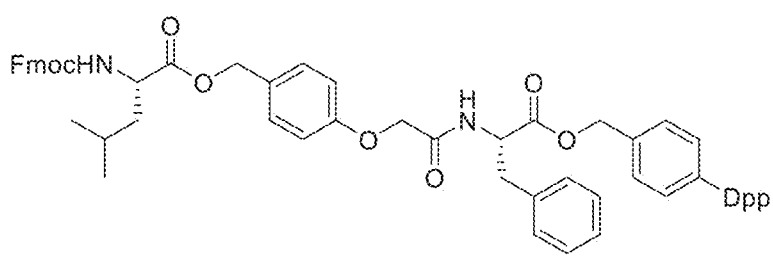
FIG. 10 shows, as a non-limiting example, the resulting compound of the attachment of the HPG GAP molecule to the C-terminus of Fmoc-protected leucine.
Figure 11:
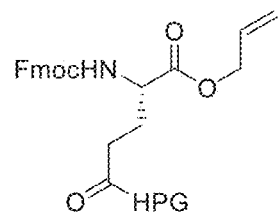
FIG. 11 depicts as a non-limiting example the compound resulting from the side-chain protection of glutamic acid with HPG, wherein the C-terminus of glutamic acid is protected with an allyl group as a non-limiting example of possible C-terminal protection strategies.
Figure 12:
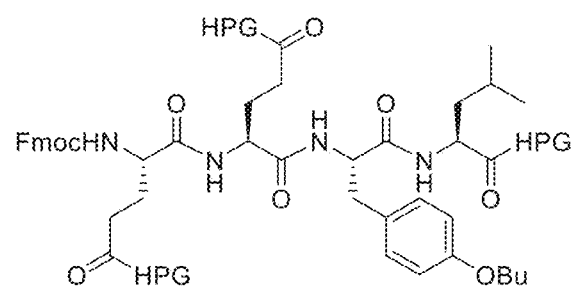
FIG. 12 shows, as a non-limiting example, the tetrapeptide, Fmoc-Glu(HPG)-Glu(HPG)-Tyr(tBu)-Leu-HPG, resulting from the novel SolPPS method disclosed herein.

The synthesis strategy of the pharmacologically interesting, biologically active peptide bivalirudin is shown as a non-limiting preferred embodiment of the novel method of SolPPS herein disclosed. FIG. 6 depicts a schematic for attaching the novel GAP molecule HPG to the C-terminus of an unspecified amino acid, and this schematic is followed for the C-terminus protection of Fmoc-leucine-OH to form the compound shown in FIG. 10. In this particular embodiment, HPG is chosen as the C-terminus protecting group to allow for post-synthesis acid labile C-terminus deprotection without facilitating C-terminus amide formation. Following this initial step, standard Fmoc/tBu chemistry is run to couple Fmoc-Tyr(tBu)-OH and form the Fmoc-protected dipeptide. Subsequently, the schematic shown in FIG. 6 for amino acid side-chain protection is followed to protect the side chain of Fmoc-Glu-OAllyl with HPG before incorporation into the growing peptide, resulting in in the compound shown in FIG. 11. Allyl deprotection of the C-terminus of the Fmoc-Glu(HPG)-OAllyl is performed by treatment with Pd(PPh$_3$)$_4$ and triisopropyl or phenyl silane, followed by activation of the resulting molecule and coupling to the peptide. This process is repeated once more to attach the next HPG-protected glutamic acid residue, yielding the Fmoc-protected tetra-peptide shown in FIG. 12. Standard Fmoc/tBu peptide synthesis is performed to add proline and isoleucine, the above discussed procedure is performed to add the next two glutamic acid residues, and phenylalanine is subsequently added. The aspartic acid residue is protected with HPG and added just as glutamic acid following the schematic shown in FIG. 6, and the glycine residue is added thereafter.

Figure 13:
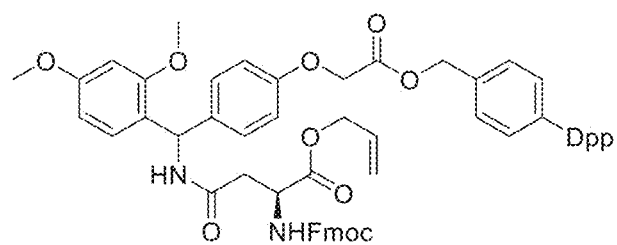
FIG. 13 depicts the compound resulting from the attachment of RAG to the side chain of an amino acid, specifically aspartic acid in this non-limiting example, wherein the C-terminus of aspartic acid is protected with an allyl group as a non-limiting example of C-terminal protection strategies.
Figure 14:
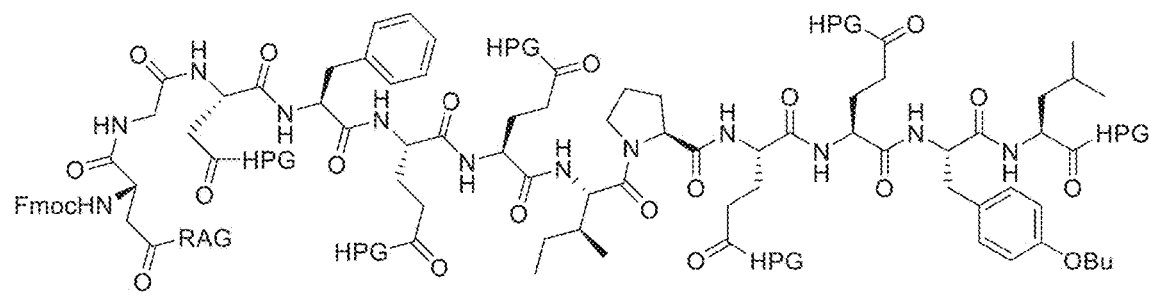
FIG. 14 shows as a non-limiting example the protected peptide resulting from the SolPPS method disclosed herein.
Figure 15:
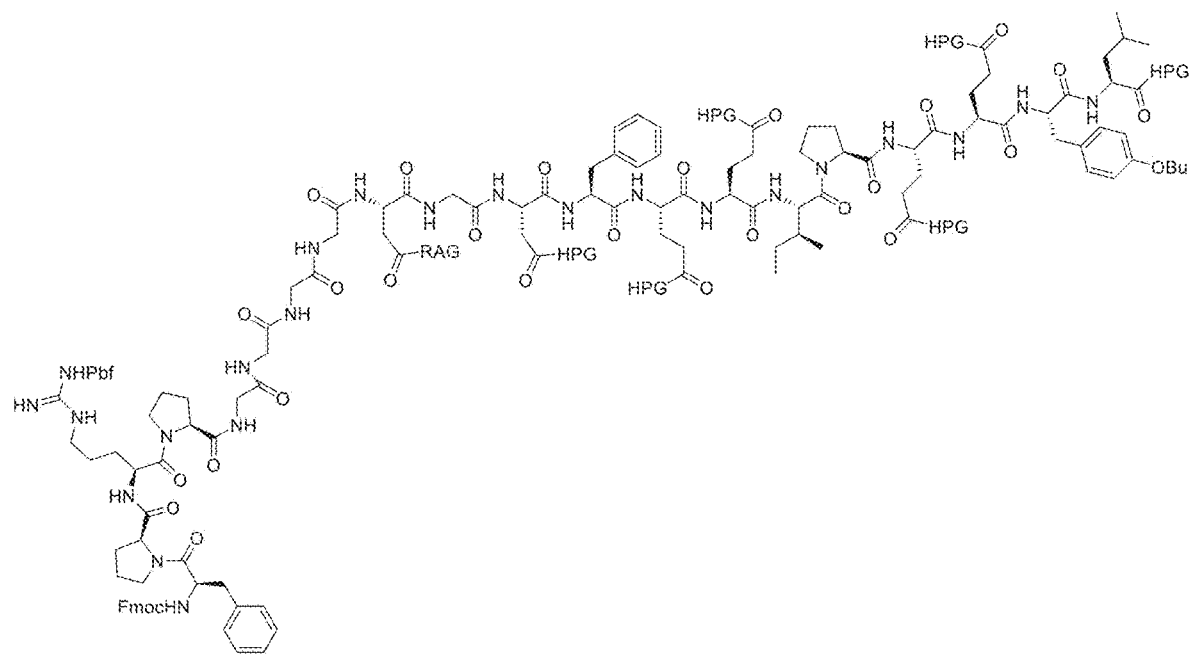
FIG. 15 depicts, as a non-limiting example, the peptide bivalirudin fully protected with novel GAP molecules.

In another preferred embodiment, the novel GAP molecule RAG is reacted with Fmoc-Asp-OAllyl to yield Fmoc-Asp(RAG)-OAllyl, the compound shown in FIG. 13. Allyl deprotection of that compound is performed and it is subsequently activated and coupled to the peptide chain, yielding the Fmoc-protected peptide shown in FIG. 14. Subsequently, standard Fmoc/tBu peptide synthesis is carried out to add four glycines, proline, arginine, another proline, and D-phenylalanine to attain the fully protected bivalirudin peptide as shown in FIG. 15.

Figure 16:
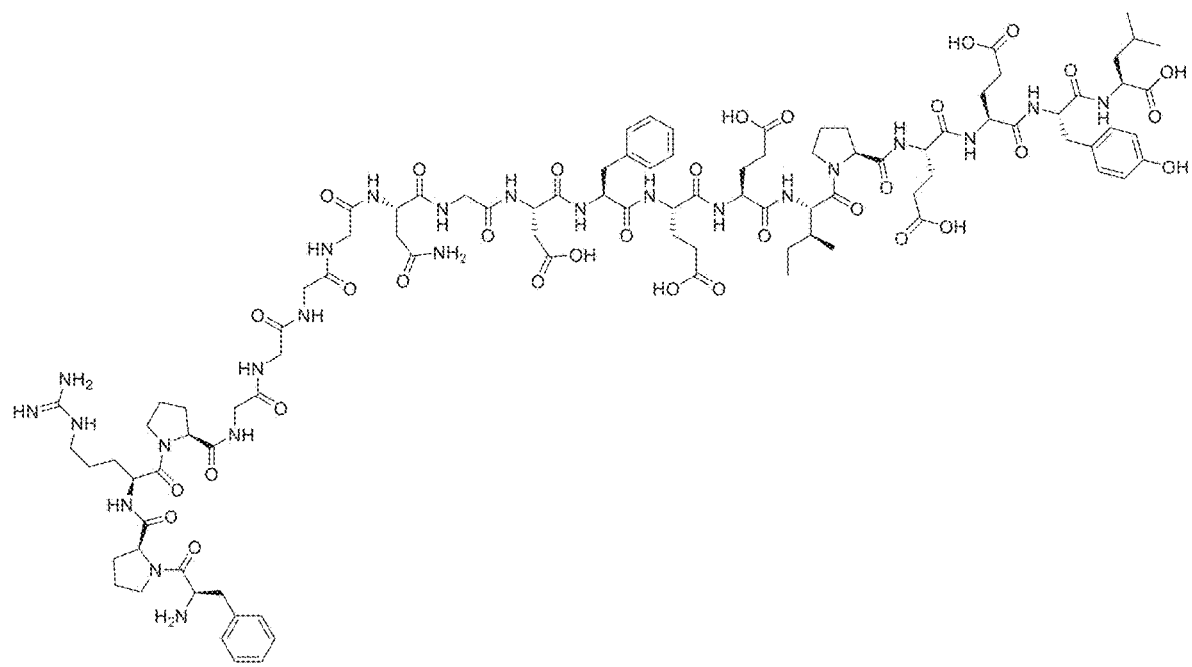
FIG. 16 depicts fully deprotected bivalirudin, attained through a one-step global deprotection that removes all side-chain and C-terminal protecting groups subsequent to Fmoc-deprotection.

In this particular embodiment, after Fmoc-deprotection of the fully protected bivalirudin, a one-step global deprotection with a TFA cocktail (i.e. 90% TFA, 5% H$_2$O, 5% triisopropylsilane (TIPS)) can be performed to cleave all of the side chain protecting groups (including the novel GAP molecules), as well as the HPG C-terminus protecting group (see FIG. 16). During this global deprotection, RAG-protected aspartic acid is also converted into deprotected asparagine. The molecule resulting from the global deprotection with the TFA cocktail is native bivalirudin.

General procedure for Fmoc deprotection and coupling: For the novel SolPPS method run in propylene carbonate (PC): To Fmoc-(AA)n-OBnDpp, Fmoc-(AA)n-HPG, Fmoc-(AA)n-RAG, or any amino acid protected at the C-terminus with any GAP protecting group, pre-dissolved in propylene carbonate (200 mM) is added deprotection base and octane thiol, followed by stirring at room temperature for 15 minutes with an alkane bilayer. Reaction mixture is then washed 2 times (X2) with fresh alkane solvent, and then washed 3 times with saturated ammonium chloride aqueous solution, and then dried. In a separate propylene carbonate solution is added 3.0 equivalents (eq.) of TBTU or TFFH, 3.0 eq Fmoc-AA-OH, and 3.0 eq. diisopropylethylamine (DIPEA) and the reaction is stirred for 7 min. This solution is then added to the previously dried PC solution containing H-(AA)n-(GAP molecule) and allowed to couple with stirring for 10-60 min. An excess of quenching agent is then added, such as long-chain (having 10 to 18 carbons linearly linked, i.e. C10-C18) aliphatic thiols, long-chain (C10-C18) aliphatic alcohols, long-chain (C10-C18) aliphatic amines, long-chain (C10-C18) aliphatic selenols, aliphatic polyamines, or aliphatic polyalcohols. The reaction mixture is then washed 3 times with saturated ammonium chloride aqueous solution and then dried to afford the elongated peptide in PC solution. This process is repeated as necessary to generate the peptide with the desired sequence and length. For the novel SolPPS method run in dichloromethane or ethyl acetate: To Fmoc-(AA)n-OBnDpp, Fmoc-(AA)n-

HPG, Fmoc-(AA)n-RAG, or any amino acid protected at the C-terminus with any GAP protecting group, pre-dissolved in DCM or ethyl acetate (100 mM) is added deprotection base, followed by stirring at room temperature for 10 minutes. Reaction mixture is then washed 3 times with saturated ammonium chloride aqueous solution, 3 times with saturated sodium bicarbonate aqueous solution, and then dried. In a separate DCM or ethyl acetate solution is added 2.0 eq of TBTU or TFFH, 2.0 eq Fmoc-AA-OH, and 5.0 eq. DIPEA and the reaction is stirred for 7 min. This solution is then added to the previously dried DCM or ethyl acetate solution containing H-(AA)n-(GAP molecule) and allowed to couple with stirring for 10-60 min. An excess of quenching agent is then added, such as long-chain (C10-C18) aliphatic thiols, long-chain (C10-C18) aliphatic alcohols, long-chain (C10-C18) aliphatic amines, long-chain (C10-C18) aliphatic selenols, aliphatic polyamines, or aliphatic polyalcohols. The reaction mixture is then washed 3 times with saturated ammonium chloride aqueous solution and then dried to afford the elongated peptide in DCM or ethyl acetate solution. This process is repeated as needed to generate the peptide with the desired sequence and length.

General procedure for EDCI coupling: Reaction mixture containing a deprotected N-terminus of an amino acid or peptide is cooled in an ice bath. 2 eq of the amino acid to be coupled to such free N-terminus is subsequently added to the reaction mixture, followed by 2 eq of EDCI. The resulting mixture is removed from the ice bath and stirred for 1 hour, and an excess of quenching agent is then added, such as long-chain (C10-C18) aliphatic thiols, long-chain (C10-C18) aliphatic alcohols, long-chain (C10-C18) aliphatic amines, long-chain (C10-C18) aliphatic selenols, aliphatic polyamines, or aliphatic polyalcohols. Reaction mixture is then washed 3 times with saturated ammonium chloride aqueous solution, 3 times with saturated sodium bicarbonate aqueous solution, and then dried.

In another embodiment, the present disclosure can include a chemical composition comprising a group-assisted purification (GAP) constituent and a linker constituent. In one embodiment, a GAP constituent can be any molecule displaying characteristics of a GAP molecule or anchor described herein, such as a GAP molecule that is capable of precipitation from non-polar organic solvents. For example, the GAP constituent can be sufficiently polar such that it is not soluble in non-polar organic solvents, such as petroleum ether, hexanes, heptane, etc. In another example, the GAP constituent can include a sufficiently polar bond to render the GAP constituent insoluble in non-polar organic solvents, such as a phosphorous-oxygen bond (phosphine oxide), sulfur-oxygen bond, nitrogen-oxygen bond, or any other polar bond sufficient to render the GAP constituent insoluble in non-polar organic solvents. In another embodiment, the GAP constituent can include moieties lending to pi-pi stacking, such as aromatic moieties; for example, the GAP constituent can include one or more phenyl substituents. In another embodiment, the GAP constituent can be any molecule suitable to exclude itself from non-polar organic solvents. In another embodiment, the GAP constituent can include a nucleophilic moiety capable of participating in a coupling reaction. For example, the GAP constituent can include an alcohol, amine, thiol, or any other nucleophilic moiety. In another embodiment, the GAP constituent can lend its solubility characteristics to the molecule to which it is attached. In another embodiment, the GAP constituent can include a hydrocarbon moiety; preferably, the hydrocarbon moiety can include at least six carbon atoms. In another embodiment, the GAP constituent can include an alkyl moiety; preferably, the alkyl moiety can include six to thirty carbons.

Preferably, the GAP constituent comprises a polar covalent bond with significant charge distribution. In one embodiment, significant charge distribution can result from p-orbitals of the bonding atoms being mismatched in size; in another embodiment, significant charge distribution can result when one of the bonding atoms is forced to hybridize all of its p-orbitals, creating reduced pi-overlap, which can cause charge separation. In another embodiment, the GAP constituent can further include one or more aromatic moieties to allow for pi-pi stacking, which can facilitate crystallization during precipitation and also reduce aqueous solubility. In another embodiment, the GAP constituent can further include additional alkyl substituents which can further reduce aqueous solubility. In another embodiment, the GAP constituent can include a nucleophilic moiety capable of participating in a nucleophilic substitution reaction, such as coupling reactions known in the art, especially with respect to peptide synthesis. In one embodiment, a GAP constituent can include a free alcohol, amine, or other nucleophilic moiety capable of participating in a nucleophilic substitution reaction. In another embodiment, a GAP constituent is preferably between 250 and 1250 Daltons.

For example, and in one embodiment as shown in FIG. 20C, a GAP constituent

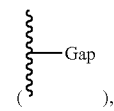

can include:

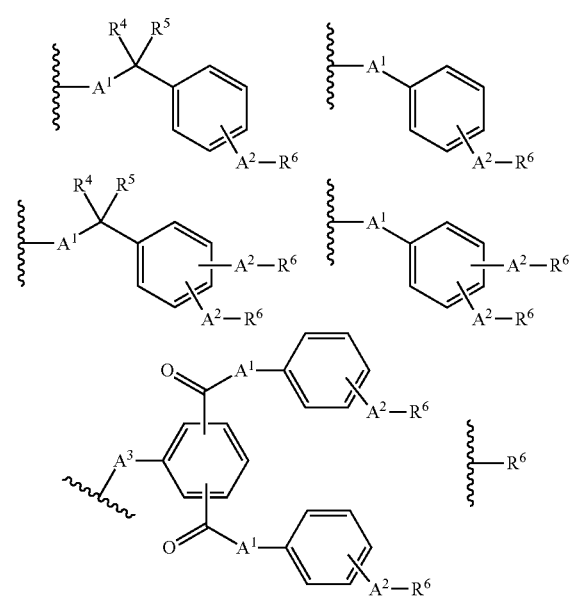

wherein: $A^1$ is selected from the group consisting of: S, O, NH, NMe, NEt, NBn, NPh, —C(O)—, and —(CH$_2$)$_j$— (wherein "j" is as defined below); $A^2$ is selected from the group consisting of: S, O, NH, NMe, NEt, NBn, NPh, —C(O)—, and —(CH$_2$)$_k$— (wherein "k" is as defined below); $A^3$ is selected from the group consisting of: S, O;

NH, NMe, NEt, NBn, and NPh; $R^4$ is selected from the group consisting of: —$(CH_2)_m$—H (wherein "m" is as defined below), —$CCl_3$, —$CF_3$, phenyl, isopropyl, tert-butyl, chlorophenyl, dichlorophenyl, methoxyphenyl, and dimethoxyphenyl; $R^5$ is selected from the group consisting of: —$(CH_2)_p$-Me (wherein "p" is as defined below), —$CCl_3$, —$CF_3$, phenyl, isopropyl, tert-butyl, chlorophenyl, dichlorophenyl, methoxyphenyl, and dimethoxyphenyl; $R^6$=Dpp; Dpop; or Dap, wherein:

Dpp is an abbreviation for the following:

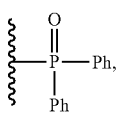

Dpop is an abbreviation for the following:

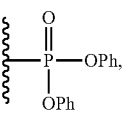

and

Dap is an abbreviation for the following:

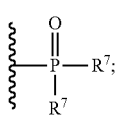

$R^7$ is selected from the group consisting of $C_yH_{(2y+1)}$ (wherein "y" is as defined below), $OC_yH_{(2y+1)}$ (wherein "y" is as defined below), $NHC_yH_{(2y+1)}$ (wherein "y" is as defined below), (2-ethyl)hexyl, and isooctyl; and j, k, m, p, and y are separate values selected from the group consisting of any integer between 0 and 30.

Constituents discussed herein can be attached to other constituents or molecules as shown by the wavy line, such as those above.

In one embodiment, a linker constituent can include any of the linker molecules discussed herein. For example, the linker constituent can substantially take the form of any of the linker molecules depicted in FIG. 18 and discussed herein. In another embodiment, the linker constituent can include a molecule with a first and second chemical moiety. In one embodiment, the first moiety can be capable of forming a bond with the GAP constituent or a spacer constituent (discussed further below). For example, the first moiety can include an electrophile capable of participating in a nucleophilic substitution reaction, such as a coupling reaction. In another example, the first moiety can be a carbonyl; in another example, the first moiety can be a carboxylic acid moiety. In another embodiment, the second moiety can be capable of forming a bond with an amino acid. For example, the second moiety can be a free alcohol, amine, or other nucleophilic moiety. In another example, the second moiety can be capable of participating in a coupling reaction. In another example, the second moiety can be capable of forming a bond with the C-terminus of an amino acid. In one embodiment, the linker constituent can be any molecule capable of linking a GAP constituent to another molecule; in another embodiment, the linker constituent can be any molecule capable of linking a spacer constituent with an attached GAP constituent to a target molecule. In another embodiment, a linker constituent can be composed such that if a charge is incurred on the atom adjacent to a nucleophilic moiety, that charge can be stabilized via resonance or conjugation. For example, with respect to the RAG molecule discussed herein, the linker constituent (in this example, Rink Amide) can incur a charge on the benzyhydryl carbon upon cleavage of the carbon-nitrogen bond that leaves the nitrogen attached to the target molecule. The linker constituent (and therefore the GAP anchor comprising the linker constituent) can include conjugation that is capable of stabilizing the charge incurred on the benzydryl carbon such that the cleavage reaction to remove the GAP anchor from the target molecule is energetically favorable. In another embodiment, a charge incurred on a carbon adjacent a nucleophilic moiety can be stabilized by virtue of the fact that the carbon atom is a tri-substituted (tertiary) carbon. In another embodiment, a linker constituent can be affixed to a target molecule via a bond that is susceptible to cleavage under hydrolytic conditions known in the art.

Figure 19:
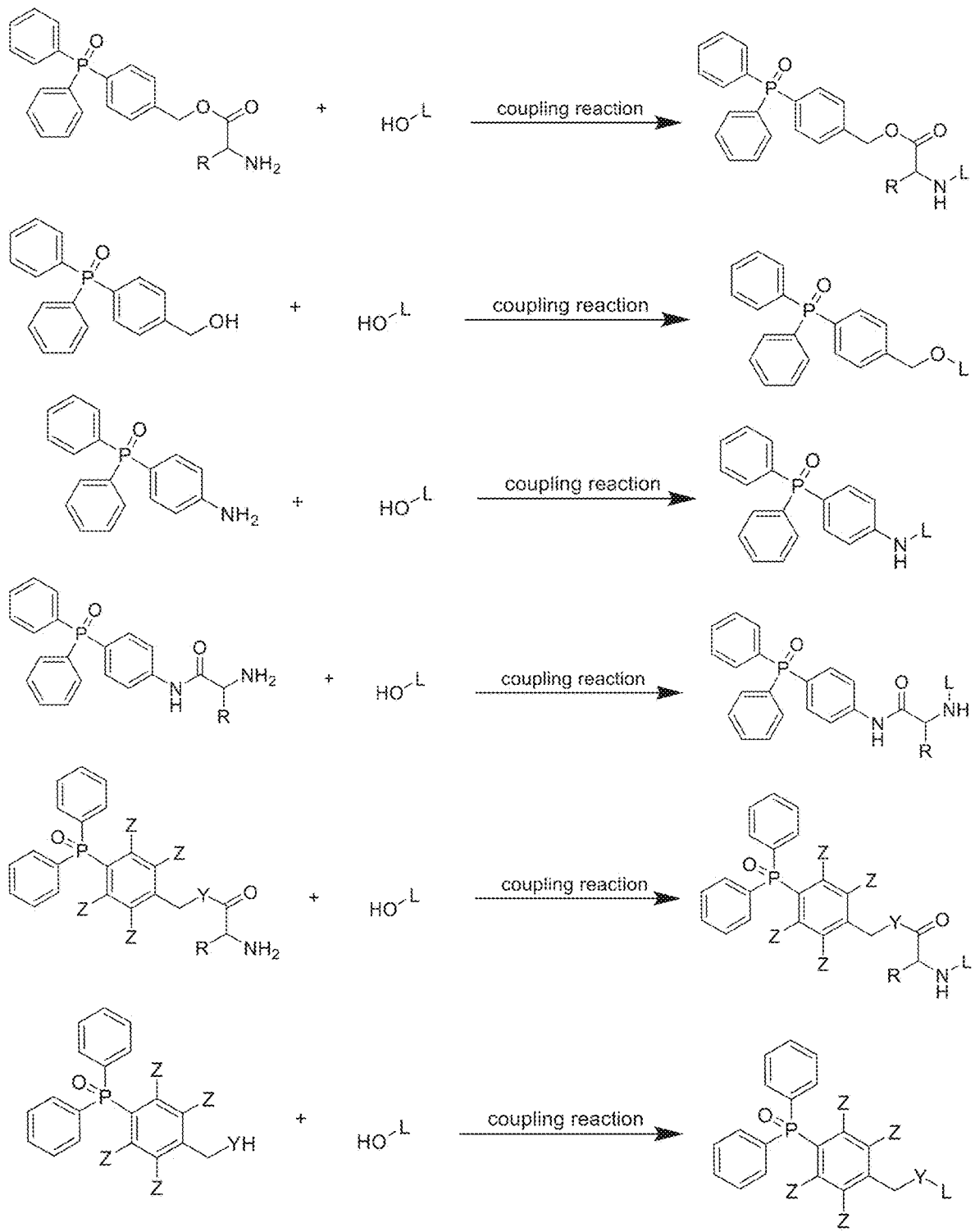
FIG. 19 shows a myriad of representative coupling reactions to synthesize novel GAP molecules disclosed herein.
Figure 19:
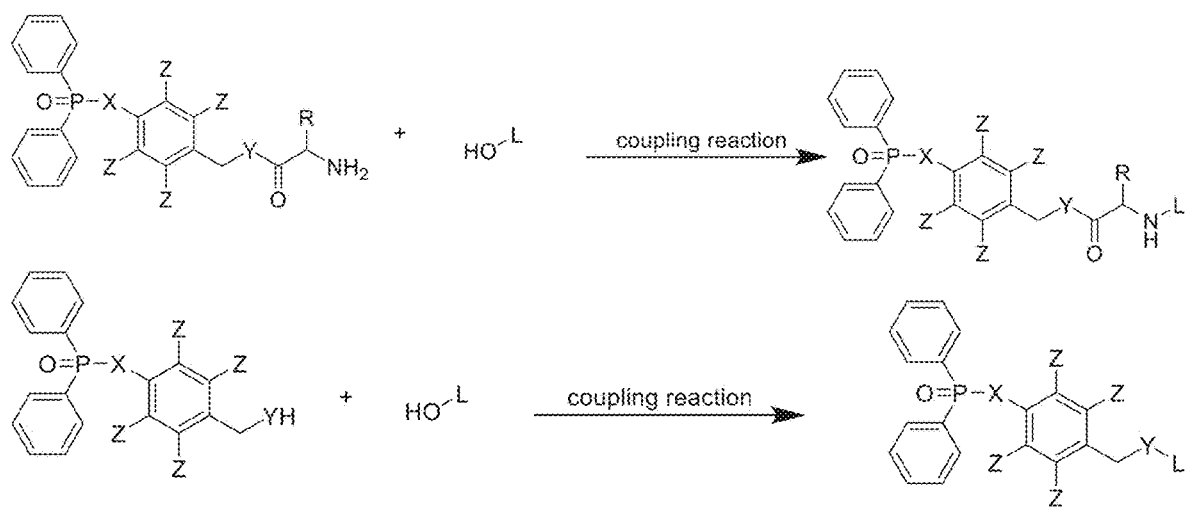

Preferably, the linker constituent can enable the composition comprising the linker and GAP constituents to be removably coupled to another molecule via the second moiety of the linker constituent. For example, the first moiety of the linker constituent can participate in a bond with either the GAP constituent or spacer constituent, and such bond can be stable to a myriad of conditions, such as acid and base deprotection reactions known in the art (i.e. TFA global deprotections like those discussed herein, hydrolysis reactions, etc.). In this manner, the composition can be resistant to degradation and maintain its chemical structure in a number of conditions. Preferably, a bond formed between the second moiety of the linker constituent and another molecule can be labile to a reaction to which the first moiety bond is stable. In this manner, the composition can be cleaved from another molecule at the second moiety of the linker constituent while maintaining the bond between the first moiety and either the spacer constituent or GAP constituent. In one embodiment, this functionality (i.e. orthogonality of the second moiety bond relative to the first moiety bond) can be enabled by the inherent structure of the linker constituent, such as those described in FIGS. 19 and 22A. For example, a linker constituent can be specially designed to exhibit this functionality, such as with linker molecules known in the art, examples of which can be found in FIGS. 19 and 22A. In another embodiment, the bond between the first moiety and either the spacer constituent or GAP constituent, and the second moiety and another molecule, can be cleavable under the same conditions.

For example, a linker constituent can be exemplified by HMPA-OH, such as is seen in FIG. 5. HMPA-OH comprises first and second chemical moieties. The first moiety of HMPA-OH is a carboxylic acid that is vulnerable to nucleophilic attack—in this manner, a nucleophilic moiety (for example, a GAP constituent nucleophile, or the N-terminus of an amino acid) can form a bond with the first moiety of HMPA-OH via nucleophilic substitution. The second moiety of HMPA-OH is a benzyl alcohol, which itself is a nucleophilic moiety capable of attacking an electrophile, such as the carbonyl carbon at the C-terminus of an amino acid, to similarly form a bond via nucleophilic substitution. Further, the structure of HMPA-OH enables the bond formed at the second moiety of the linker constituent to be cleaved under strong acid conditions. Preferably, the bond formed at the first moiety (such as with HOBnDpp, or with an amino acid, as depicted in FIG. 5) remains stable to such conditions.

In one embodiment, a linker constituent

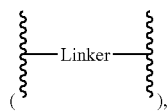

which can be attached to two other constituents (i.e. a GAP constituent, another linker constituent, a spacer constituent, or any combination thereof) can include, as seen in FIG. 20A:

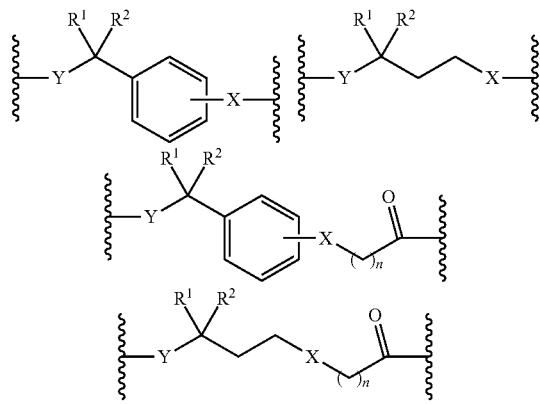

wherein X is selected from the group consisting of: Y (as defined below), —C(O)—, and —(CH$_2$)$_a$— (wherein "a" is as defined below); Y is selected from the group consisting of: S, NH, NMe, NEt, NBn, NPh, and O; R$^1$ is selected from the group consisting of: —(CH$_2$)$_b$—H (wherein "b" is as defined below), —CCl$_3$, —CF$_3$, phenyl, isopropyl, tert-butyl, chlorophenyl, dichlorophenyl, methoxyphenyl, and dimethoxyphenyl; R$^2$ is selected from the group consisting of: —(CH$_2$)$_c$—H (wherein "c" is as defined below), —CCl$_3$, —CF$_3$, phenyl, isopropyl, tert-butyl, chlorophenyl, dichlorophenyl, methoxyphenyl, and dimethoxyphenyl; and a, b, c, and n are separate values selected from the group consisting of any integer between 0 and 30.

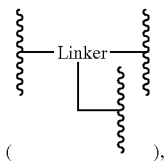

In another embodiment, a linker constituent which can be attached to three other constituents (i.e. a GAP constituent, another linker constituent, a spacer constituent, or any combination thereof), can include, as seen in FIG. 20A:

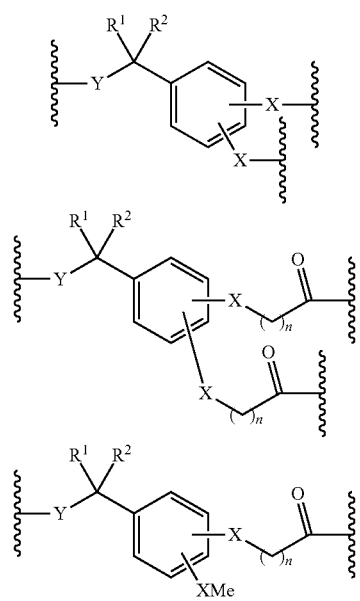

wherein X is selected from the group consisting of: Y (as defined below), —C(O)—, and —(CH$_2$)$_a$— (wherein "a" is as defined below); Y is selected from the group consisting of: S, NH, NMe, NEt, NBn; NPh; and O; R$^1$ is selected from the group consisting of: —(CH$_2$)$_b$—H (wherein "b" is as defined below), —CCl$_3$, —CF$_3$, phenyl, isopropyl, tert-butyl, chlorophenyl, dichlorophenyl, methoxyphenyl, and dimethoxyphenyl; R$^2$ is selected from the group consisting of: —(CH$_2$)$_c$—H (wherein "c" is as defined below), —CCl$_3$, —CF$_3$, phenyl, isopropyl, tert-butyl, chlorophenyl, dichlorophenyl, methoxyphenyl, and dimethoxyphenyl; and a, b, c, and n are separate values selected from the group consisting of any integer between 0 and 30.

In another embodiment, the present disclosure can include a chemical composition comprising a GAP constituent, a linker constituent (linker), and a spacer constituent (spacer). In one embodiment, the spacer can be any molecule capable of facilitating connection between the GAP constituent and the linker constituent. For example, the spacer constituent can comprise a first moiety operable to bond with the GAP constituent, and a second moiety operable to bond with the linker constituent. In one embodiment, the spacer can be an amino acid with a C-terminus and an N-terminus, and the C-terminus can bond with a nucleophilic moiety of the GAP constituent, and the N-terminus can bond with an electrophilic moiety of the linker. In another embodiment, the spacer can lend desired solubility characteristics to the overall chemical composition. For example, the spacer can include alkyl chains, amino acids, polar-organic moieties, or any other chemical moieties displaying a desired solubility characteristic. In another embodiment, a spacer constituent can provide enough non-conjugating physical separation between the linker and the GAP constituents, such as through a series of sp3 hybridized carbon atoms, such that the GAP and linker constituents are electronically isolated from each other. Such isolation can prevent either constituent from negatively influencing the other, such as in a way that could interfere with properties displayed by each constituent as disclosed herein. For example, a spacer constituent can prevent the chemical-electronic properties of a GAP constituent from interfering with conjugation found in a linker constituent, such as conjugation that enables a bond formed by, e.g., a second moiety of the linker, to be cleavable under known conditions. In another example, a spacer can be disposed between and thereby provide distance between the moieties of GAP and linker constituents that are capable of participating in a coupling or other bond-forming reaction with each other, such as to reduce steric hindrance that could render the reaction inefficient.

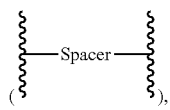

In one embodiment, and as shown in FIG. 20B, a spacer constituent such as when attached to two other constituents (i.e. a GAP constituent, a linker constituent, another spacer constituent, or any combination thereof), can include:

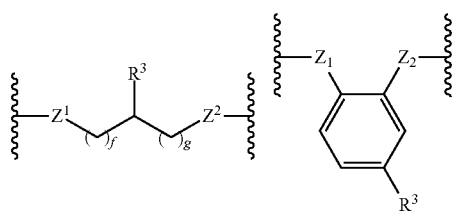

wherein: $Z^1$ is selected from the group consisting of: S, O, NH, NMe, NEt, NBn, NPh, —C(O)—, and —(CH$_2$)$_d$— (wherein "d" is as defined below); $Z^2$ is selected from the group consisting of: S, O, NH, NMe, NEt, NBn, NPh, —C(O)—, and —(CH$_2$)$_e$— (wherein "e" is as defined below); $R^3$ is selected from the group consisting of: H, methyl, ethyl, propyl, isopropyl, benzyl, isobutyl, sec-butyl, tert-butyl, 2-(methylmercapto)ethyl, and the structures listed below:

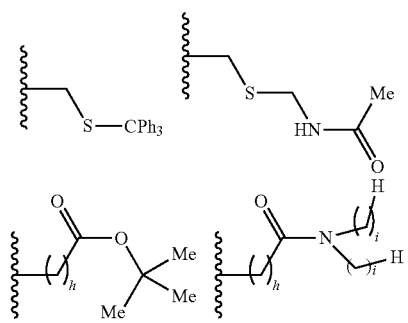

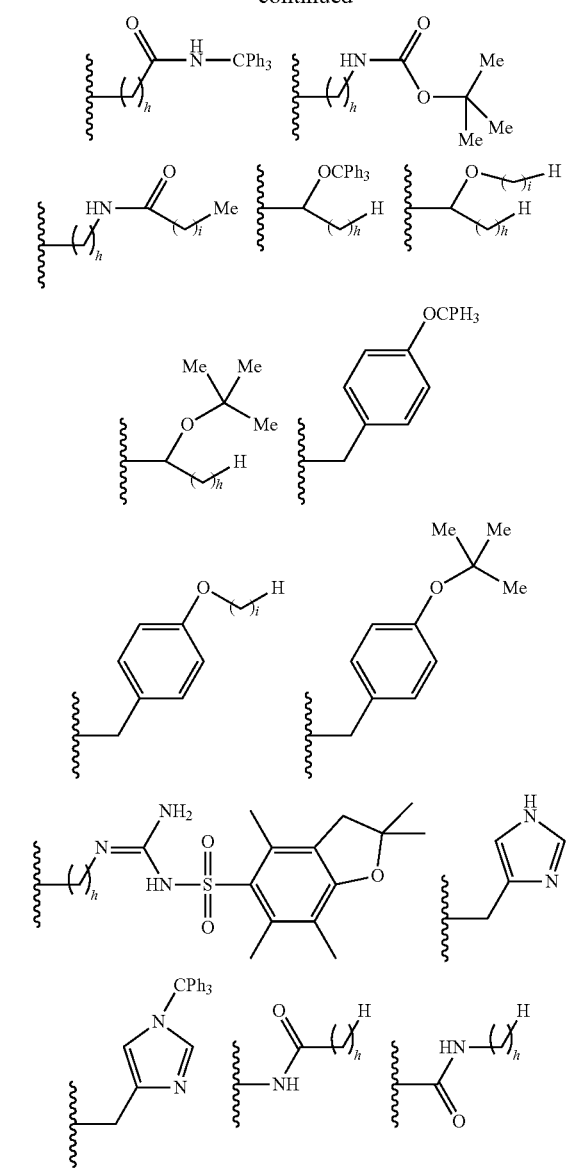

and d, e, f, g, h and i are separate values selected from the group consisting of any integer between 0 and 30.

In one embodiment, the present disclosure can include a group-assisted purification (GAP) anchor molecule. For example, a GAP anchor (anchor molecule) (GAP molecule) (GAP protecting group) can be a product of the reactions shown in FIG. 19. In another example, a GAP anchor can be RAG, HPG, or NH$_2$PhDpp as described herein and shown in FIGS. 3, 5 and 7, respectively. In another embodiment, a GAP anchor can be a molecule defined in FIGS. 20A-20F, 21A-21B, and 22. In another example, a GAP anchor can be a GAP constituent. In another embodiment, a GAP anchor can be a molecule comprising a GAP constituent and a linker constituent; in another embodiment, a GAP anchor can comprise a GAP constituent, linker constituent, and spacer constituent. For example, a GAP anchor can incorporate any number of GAP constituents, linker constituents, or spacer constituents. Preferably, a GAP anchor (H-Anchor) can take the form as shown in FIG. 20A:

Structures of the type H-Gap, H-Linker-Gap,

H-Linker-Gap,
  └─Gap

H-Linker-Spacer-Gap or

H-Linker-Spacer-Gap,
  └─Spacer-Gap collectively known together as H-Anchor molecules, where H is the element Hydrogen, and Linker, Spacer, and Gap molecules are as defined below Preferably, and as exemplified in FIGS. 20A-20C, different combinations of GAP, linker, and spacer constituents can be used to accomplish specific purposes. For example, the HPG molecule can be an example of a GAP anchor (H-Anchor) discussed herein. As seen in FIG. 5, a linker constituent can be, for example, HMPA-OH, which can be attached to GAP constituent (for example, OBnDpp) via a spacer constituent (for example, phenylalanine) to form HPG, an exemplary GAP anchor. A linker constituent can include HMPA-OH, which has an electrophilic moiety capable of participating in a nucleophilic substitution reaction (i.e. a carbonyl), and a nucleophilic moiety. When GAP constituent (i.e. HOBnDpp) nucleophile attacks the carbonyl, a bond can form via nucleophilic substitution. The nucleophilic moiety of the HMPA-OH (i.e. the benzyl alcohol) can then act as a nucleophile itself and attack an electrophilic moiety, such as the C-terminus of an amino acid. Alternatively, a GAP constituent, coupled with a spacer (for example, phenylalanine), can bond with HMPA-OH to form a GAP anchor HPG.

As an example, and as shown in FIG. 20D, a GAP anchor (H-Anchor) can include:

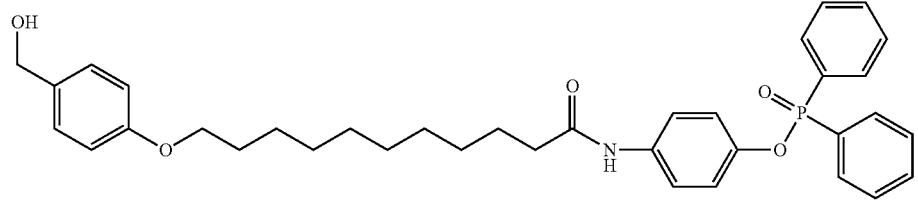 [SMILES: O=C(CCCCCCCCCCOc1ccc(CO)cc1)Nc1ccc(OP(=O)(c2ccccc2)c2ccccc2)cc1]

In this example, the H-Anchor (GAP anchor) comprises the H-Linker-Spacer-GAP format with the following specific constituents:

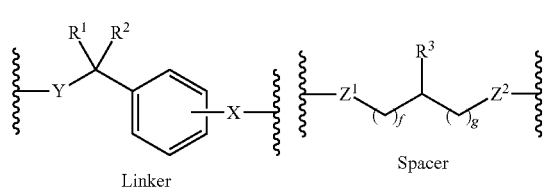

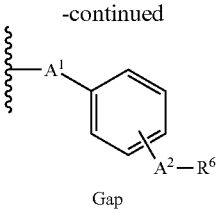

wherein $Y=O$; $R^1=H$; $R^2=H$; $X=O$ in the para position; $Z^1=-(CH_2)_d-$ where $d=1$; $f=8$; $R^3=H$; $g=0$; $Z^2=-C(O)-$; $A^1=NH$; $A^2=O$ in the para position; and $R^6=Dpp$.

In another embodiment, and as shown in FIG. 20E, an H-Anchor can comprise:

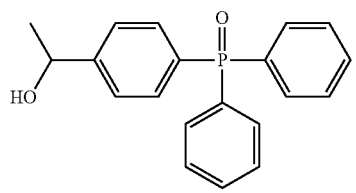 [SMILES: CC(O)c1ccc(P(=O)(c2ccccc2)c2ccccc2)cc1]

In this embodiment, the GAP anchor is in the H-Gap format with the following GAP constituent:

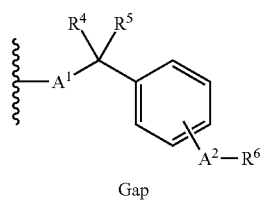

wherein $A^1=O$; $R^4=H$; $R^5=-(CH_2)_p$-Me where $p=0$; $A2=-(CH_2)_k-$ in the para position where $k=0$; and $R^6=Dpp$.

In another example, a GAP anchor can include:

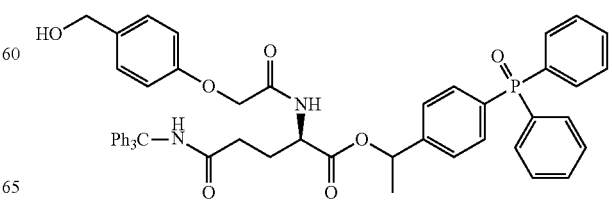

This H-Anchor molecule comprises the H-Linker-Spacer-Gap format with the following specific constituents:

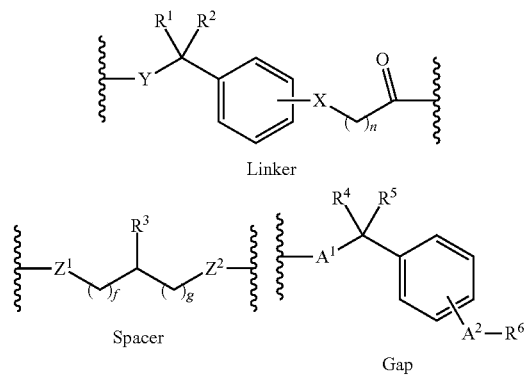

Linker

Spacer

Gap wherein Y=O; $R^1$=H; $R^2$=H; X=O in the para position; n=1; $Z^1$=NH; f=0; $R^3$ is as defined above where h=2; g=0; $Z^2$=—C(O)—; $A^1$=O; $R^4$=H; $R^5$=—$(CH_2)_p$-Me where p=0; $A^2$=—$(CH_2)_k$— in the para position where k=0; $R^6$=Dpp; and

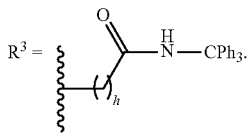

In another embodiment, the present disclosure can include, as seen in FIGS. 21A-21B, chemical compositions such as:

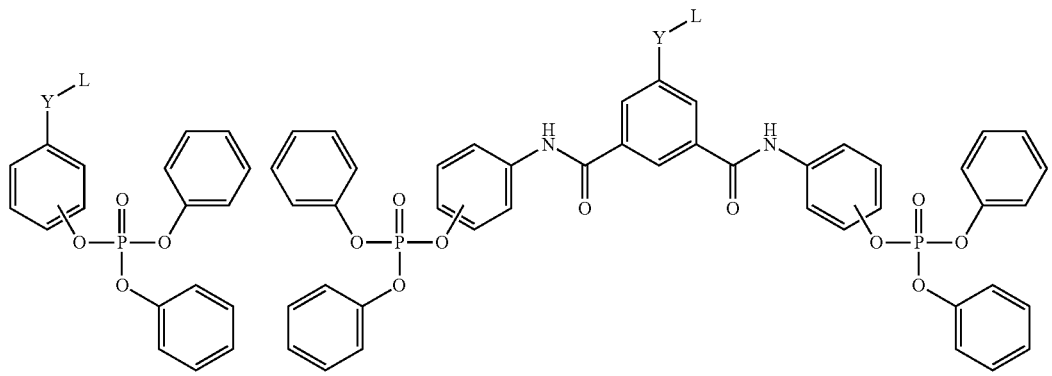

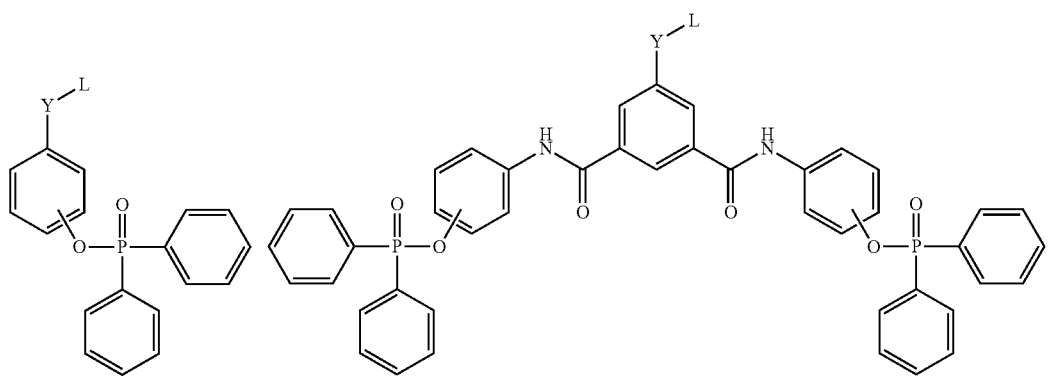

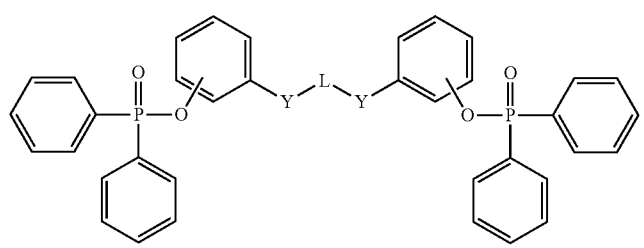

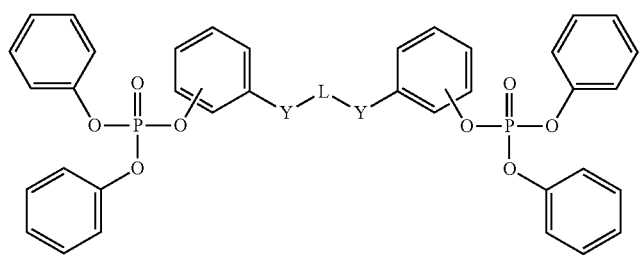
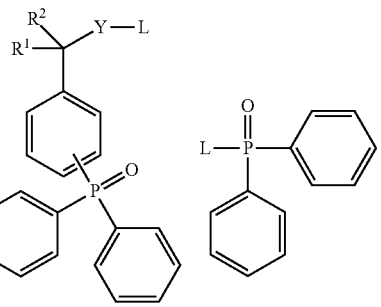
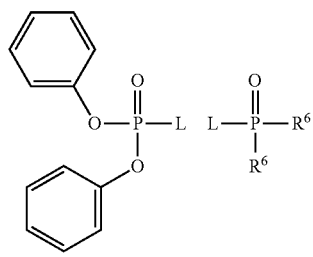

wherein: Y is selected from the group consisting of: S, O, NH, NMe, NEt, and N-iPr; $R^1$ is selected from the group consisting of: H, —$(CH_2)_a$—H (wherein "a" is selected from the group consisting of any integer from 0 to 30), —$CCl_3$, —$CF_3$, phenyl, isopropyl, tert-butyl, chlorophenyl, dichlorophenyl, methoxyphenyl, and dimethoxyphenyl; $R^2$ is selected from the group consisting of: —$(CH_2)_b$—H (wherein "b" is any integer from 1 to 30), —$CCl_3$, —$CF_3$, phenyl, isopropyl, tert-butyl, chlorophenyl, dichlorophenyl, methoxyphenyl, and dimethoxyphenyl; $R^6$ is selected from the group consisting of $C_yH_{(2y+1)}$ (wherein "y" is any integer from 1 to 30), $YC_yH_{(2y+1)}$ (wherein "y" is any integer from 1 to 30 and Y is as defined above), (2-ethyl)hexyl, and isooctyl; and L is either hydrogen or:

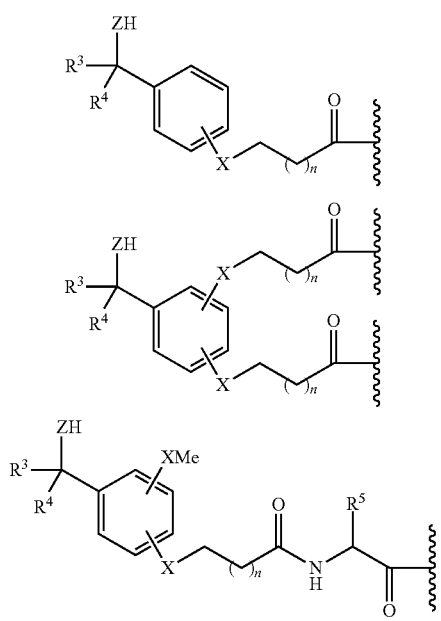

-continued

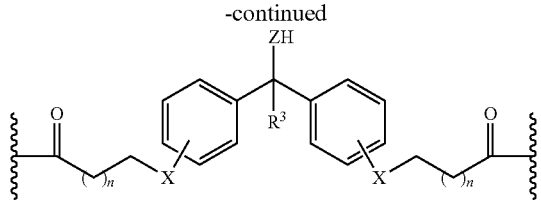

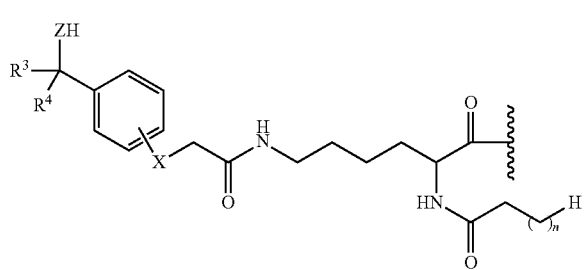

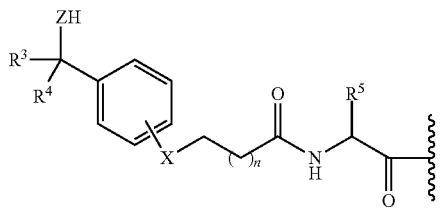

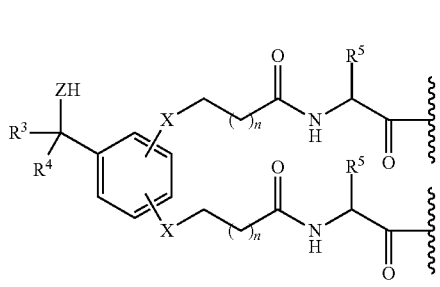

33

-continued

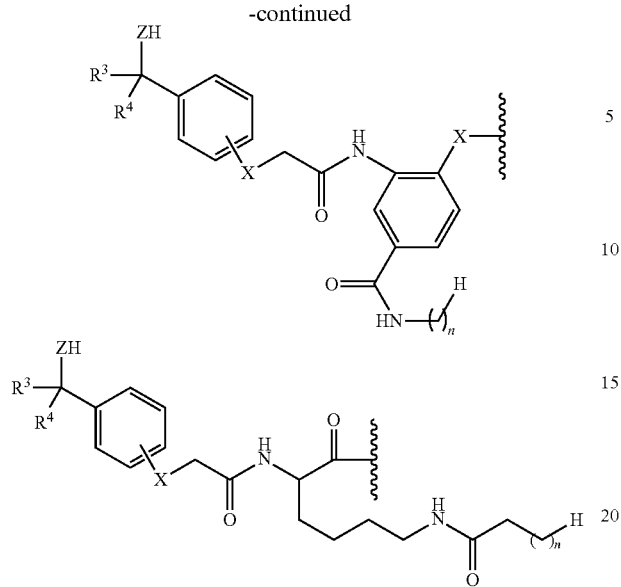

wherein Z is selected from the group consisting of: S, O, NH, NMe, NEt, and N-iPr; X is selected from the group consisting of: S, O, NH, NMe, NEt, and N-iPr; n is selected from the group consisting of any integer from 0 to 30; $R^3$ is selected from the group consisting of: H, —$(CH_2)_c$—H (wherein "c" is selected from the group consisting of any integer from 0 to 30), —$CCl_3$, —$CF_3$, phenyl, isopropyl, tert-butyl, chlorophenyl, dichlorophenyl, methoxyphenyl, and dimethoxyphenyl; $R^4$ is selected from the group consisting of: H, —$(CH_2)_d$—H (wherein "d" is selected from the group consisting of any integer from 0 to 30), —$CCl_3$, —$CF_3$, phenyl, isopropyl, tert-butyl, chlorophenyl, dichlorophenyl, methoxyphenyl, and dimethoxyphenyl;

is the attachment point to another constituent; and $R^5$ can be:

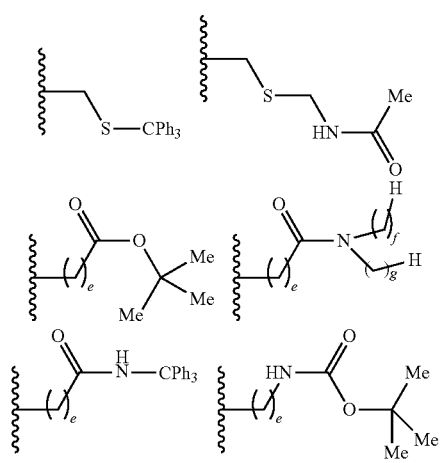

34

-continued

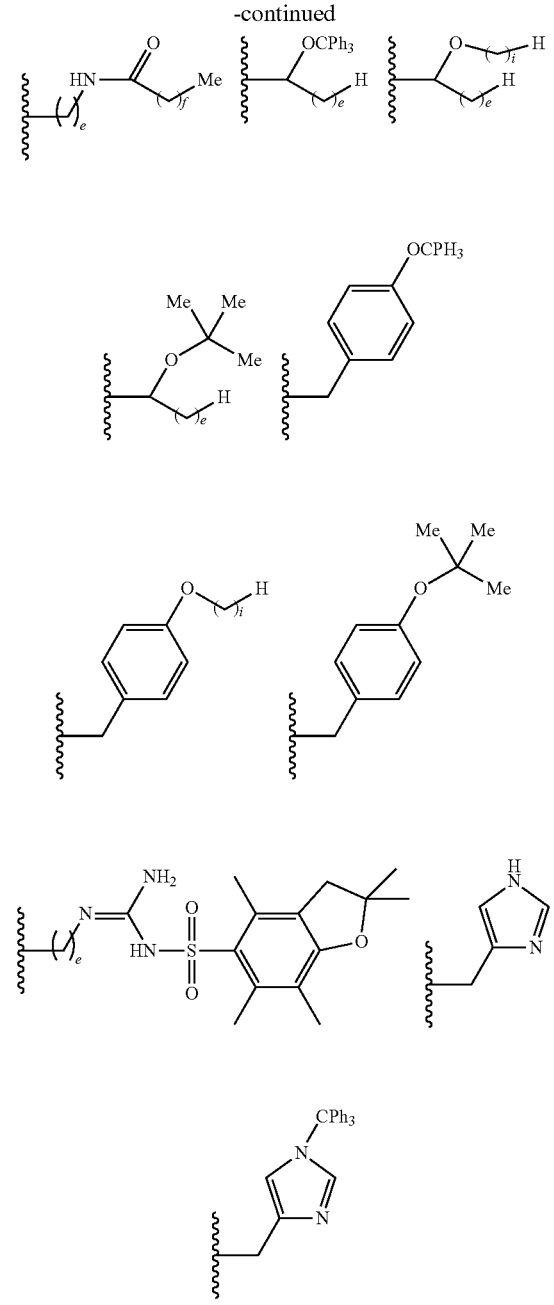

wherein:

is the attachment point to L; e is selected from the group consisting of any integer from 0 to 30; and e, f and g are selected from the group consisting of any integer from 0 to 30.

Figure 22:
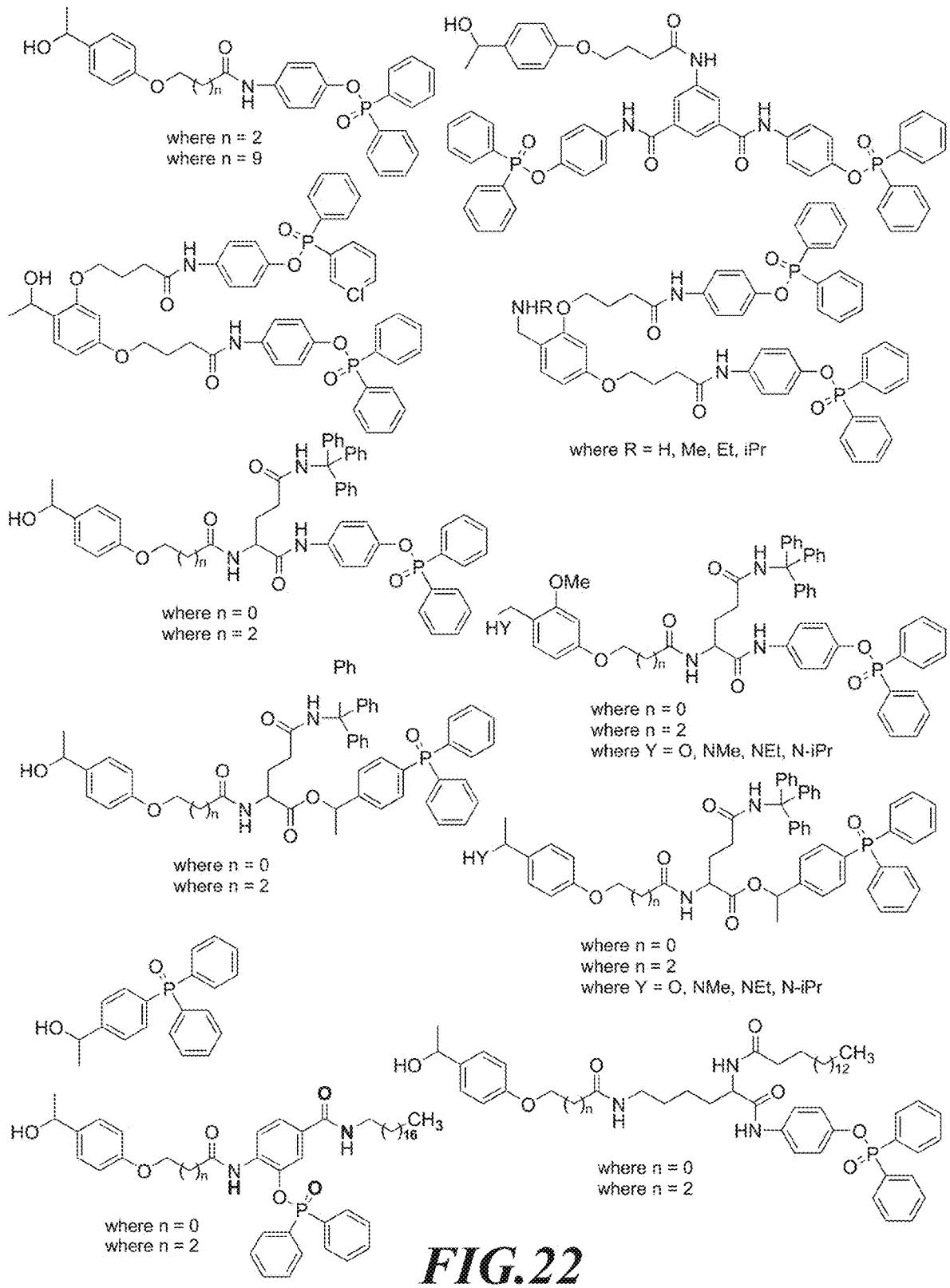
FIG. 22 depicts exemplary structures of GAP anchors (H-Anchors) in accordance with embodiments of the present disclosure.

In another embodiment, the present disclosure can include chemical compositions (such as anchor molecules disclosed herein), such as those seen in FIG. 22:

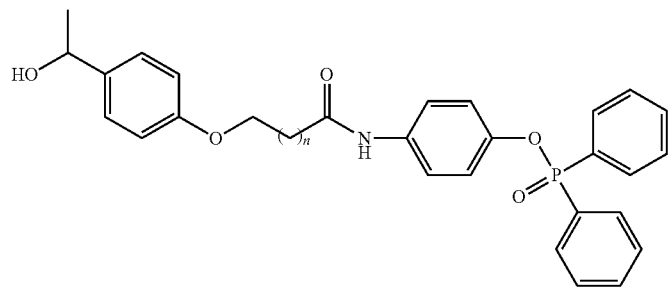
where n = 2
where n = 9
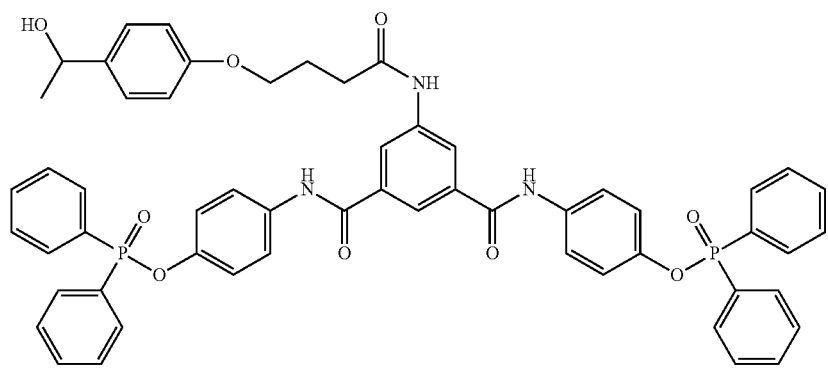
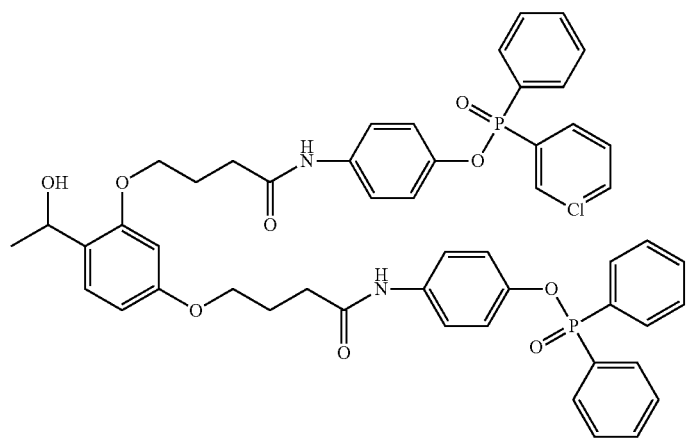
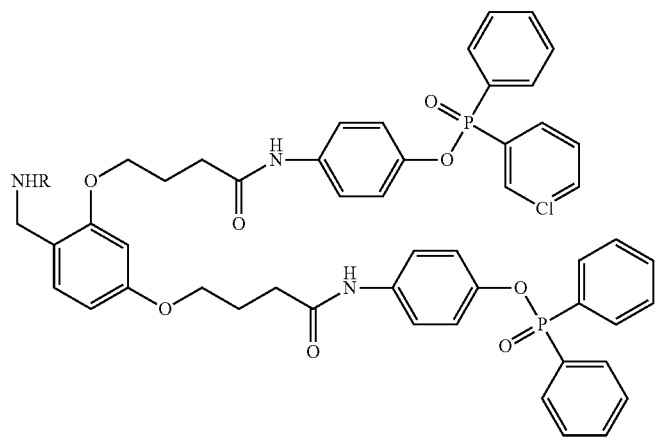
where R = H, Me, Et, iPr -continued
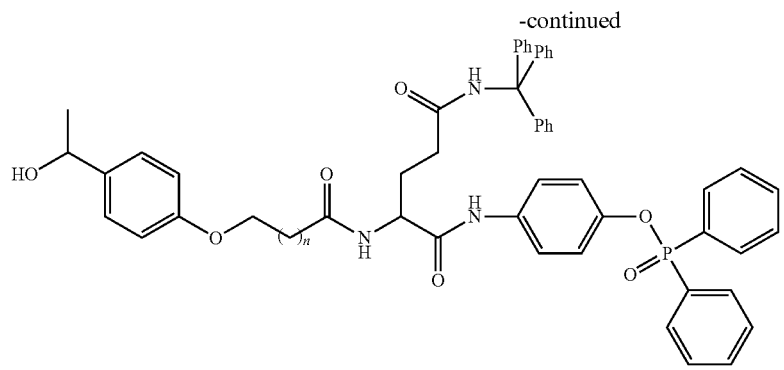
where n = 0
where n = 2
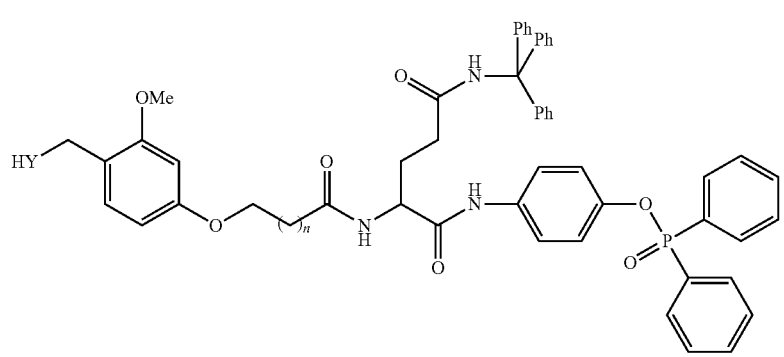
where n = 0
where n = 2
where Y = O, NMe, NEt, N-iPr
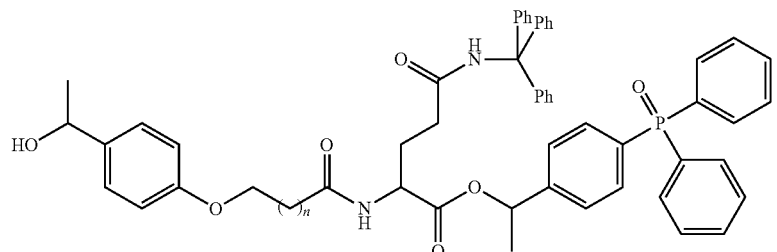
where n = 0
where n = 2
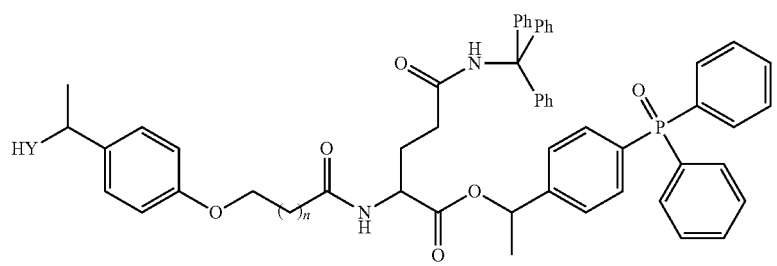 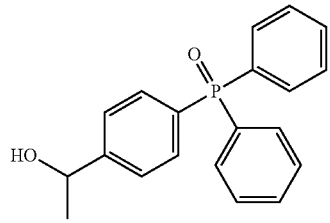
where n = 0
where n = 2
where Y = O, NMe, NEt, N-iPr -continued

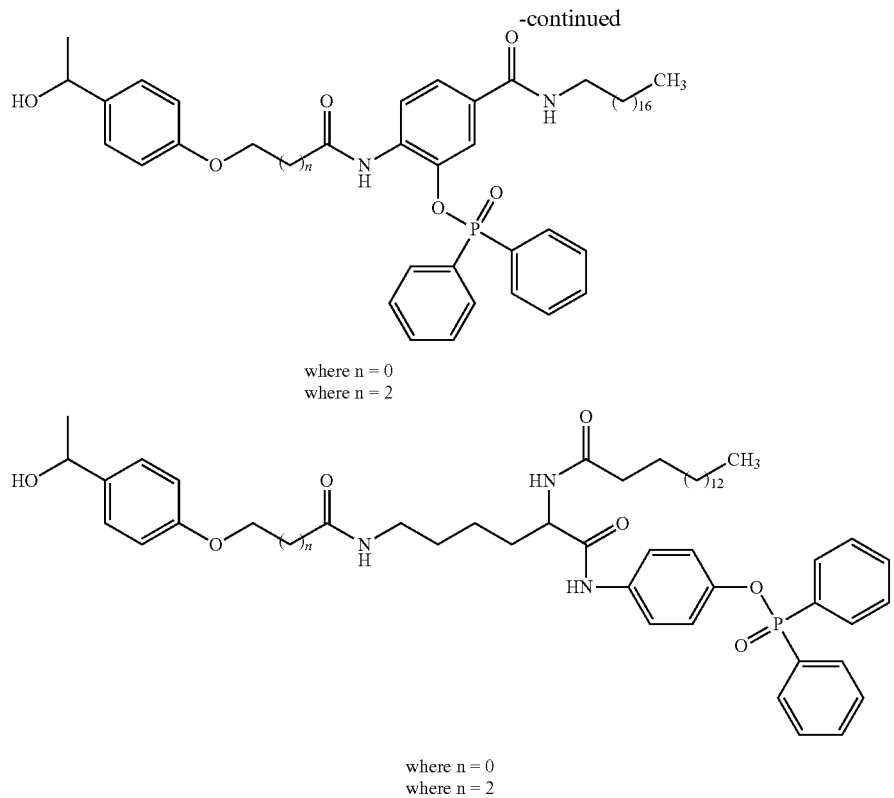

where n = 0
where n = 2 where n = 0
where n = 2

In one embodiment, the GAP, linker, and spacer constituents can be considered as three separate chemical entities capable of lending different useful properties to a given GAP anchor. For example, the GAP constituent can be a GAP molecule that includes a polar bond (e.g. phosphine oxide) and aromatic constituents, which ultimately give the GAP anchor a polar-organic quality with potential for pi-pi stacking, which can assist the GAP anchor (and attached target molecule) in selectively precipitating from non-polar solvents; in another embodiment, this can assist in the GAP anchor in excluding itself from aqueous solvents and non-polar solvents. In one embodiment, in the same GAP anchor, a linker constituent, such as those seen in FIGS. 19 and 22A, can provide the anchor with the ability to be selectively removed from a desired substrate, such as with respect to RAG and HPG anchors discussed herein that can be removed from, e.g., a C- or N-terminus or side-chain of an amino acid or peptide. For example, a linker constituent can be specifically designed to form a non-labile bond at one location, and additionally form a labile bond at another location. This orthogonality can ultimately be translated to the GAP anchor; the GAP constituent and linker constituent together can, in this manner, provide a GAP anchor with polar-organic qualities lending itself to group-assisted purification chemistry, that additionally can be cleaved under conditions the linker constituent itself would otherwise be amenable to. In another embodiment, in the same GAP anchor, a spacer constituent can provide further desired characteristics to the GAP anchor. For example, a spacer can be highly organic or non-polar, increasing the overall solubility of the GAP anchor in non-polar solvents; in another example, the spacer can be highly polar, such that the GAP anchor can also be more polar and therefore less soluble in non-polar, organic solvents.

In accordance with the principles of the present disclosure, a GAP anchor can thereby be specially formulated to assist in the synthesis of a given molecule with particular characteristics. For example, and as discussed further herein, a desired peptide can be synthesized with assistance from a GAP anchor. The GAP constituent of the anchor can have qualities discussed herein that help render the anchor (and attached peptide) soluble in organic solvents; the GAP constituent can also be amenable to pi-pi stacking to assist the peptide in selective precipitation, such as via drop precipitation. The spacer constituent can be coupled to the GAP constituent and be, for example, an amino acid, to further control solubility by providing multiple points of attachment for the different, aforementioned constituents and for additional moieties as may be necessary to achieve the desired characteristics. The linker constituent can then be operable to couple to the spacer, forming a stable product, and additionally have a free moiety capable of participating in a reaction, such as a coupling reaction. Preferably, the bond formed by the free moiety of the linker constituent can be labile to, for example, a TFA-deprotection known in the art like those discussed herein.

Different GAP constituents can offer different advantages, for example: a higher number of polar or charged substituents can increase solubility in polar solvents and reduce solubility in non-polar solvents; more-polar bonds can offer higher solubility in polar-organic solvents; more organic or fatty substituents can offer more solubility in organic solvents while reducing solubility in aqueous solvents; more pi bonds and aromatic substituents lend to better precipitation via pi-pi stacking; and larger GAP constituents can exhibit solubility control over larger target molecules. Similarly, different spacer constituents can offer different advantages, for example: smaller spacers can have less overall effect on the solubility characteristics of the GAP anchor which still providing assistance in attaching the GAP constituent to the linker constituent to form a stable compound; more polar spacers can increase solubility of the anchor in polar solvents; more organic or fatty spacers can increase solubility in organic solvents; longer spacers can decrease the potential for steric hindrance at the possible coupling points of a given GAP constituent and linker constituent; smaller spacers can enable a higher overall product loading of the GAP anchor with a target substrate by reducing the molecular weight of the GAP anchor, when compared to larger spacers. Similarly, different linker constituents can offer different advantages, for example: different cleavage conditions from target substrates (i.e. acid catalyzed, base catalyzed, etc.); C-terminal modifications (such as with the RAG molecule discussed herein) upon cleavage of the GAP anchor from, e.g., a peptide. Also, different linkers can provide different degrees of stability during peptide synthesis; for example, a linker can be more or less resistant to premature hydrolysis or diketopiperazine (DKP) formation. Different linkers can also enhance solubility in different solvents, depending on the moieties in a given linker: more organic linkers can increase solubility of the anchor in organic solvents, more polar linkers can increase solubility in polar or polar-organic solvents, etc. It will be understood by those having skill in the art that a GAP anchor can incorporate advantages from these different constituents to arrive at an anchor specifically tailored for a given chemical synthesis strategy.

In another embodiment, the present disclosure can include a method for synthesizing a peptide, which can include the steps of coupling a first amino acid to an anchor molecule, wherein the anchor molecule comprises a group-assisted purification (GAP) constituent and a linker constituent, and wherein the first amino acid is coupled to the linker constituent of the anchor molecule; forming a peptide bond between a second amino acid and the first amino acid; and removing the anchor molecule from the first amino acid. The method can further include an anchor that comprises a spacer constituent disposed between the GAP constituent and the linker constituent. In one embodiment, the spacer constituent can be an amino acid. In another embodiment, the present disclosure can include a method of synthesizing a peptide using a GAP molecule disclosed herein, such as in FIGS. 21A, 21B, and 22. In one embodiment, the method of peptide synthesis can enable increased solubility control over a target peptide by using an anchor molecule that leverages characteristics of its respective constituents. Anchor molecules like those discussed herein can be attached to a C-terminus, N-terminus, or side chain of any given amino acid for incorporating into a peptide. It will be understood by those having skill in the art that such a method can be utilized to synthesize peptides of a desired length, comprising a desired number of amino acids.

Figure 23A:
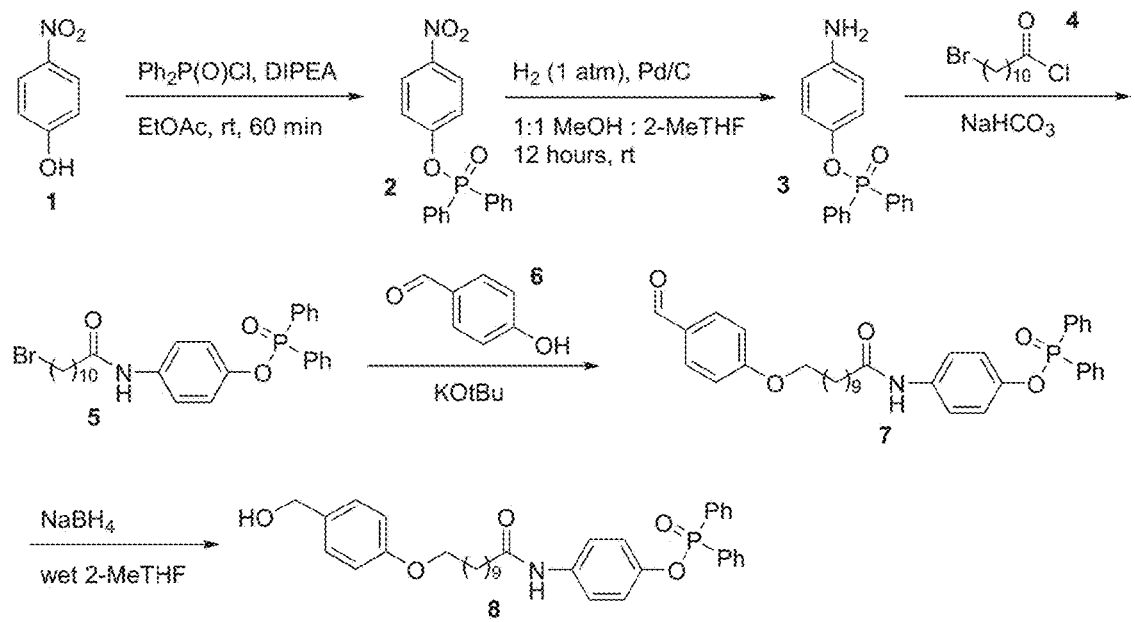
FIGS. 23A-23B depict exemplary methods of synthesizing chemical compounds in accordance with embodiments of the present disclosure.

In another embodiment, the present disclosure can include a method of synthesizing a GAP anchor, such as, for example, the method of FIG. 23A:

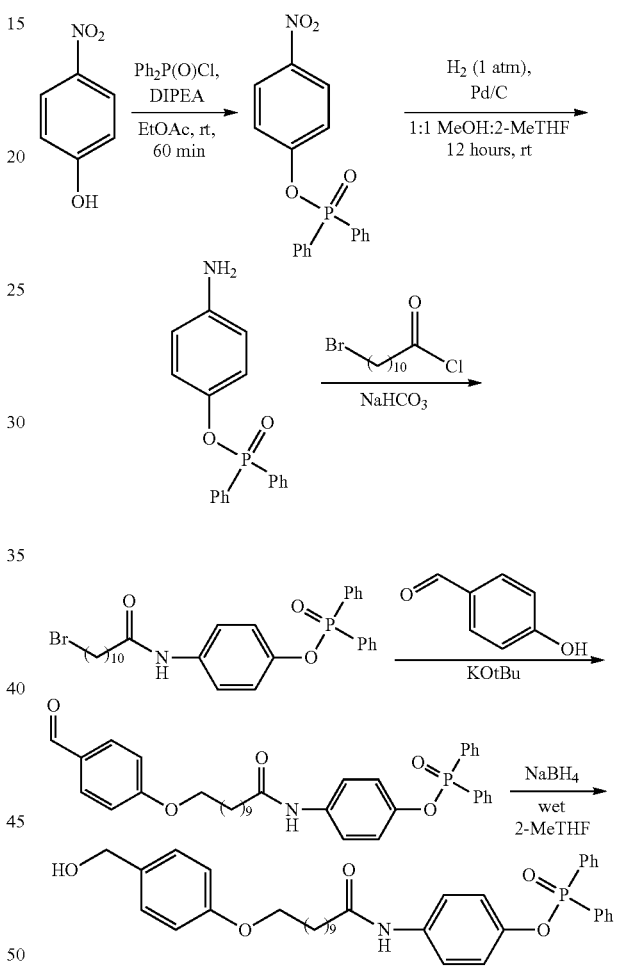

Figure 23B:
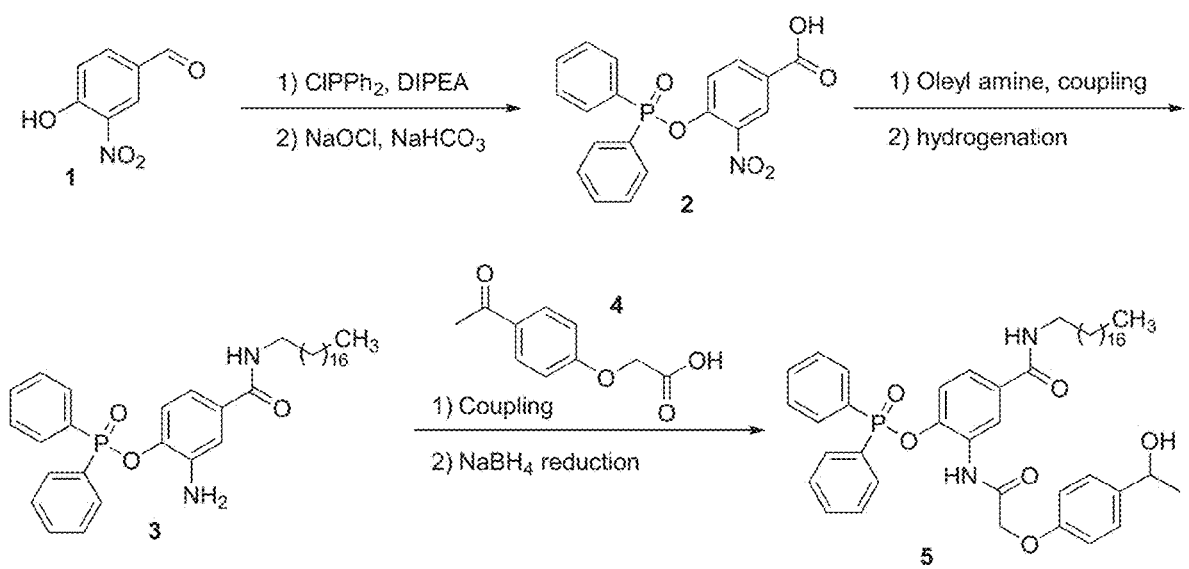

In another embodiment, a method of synthesizing an H-Anchor molecule (anchor molecule) can include, for example, and as seen in FIG. 23B:

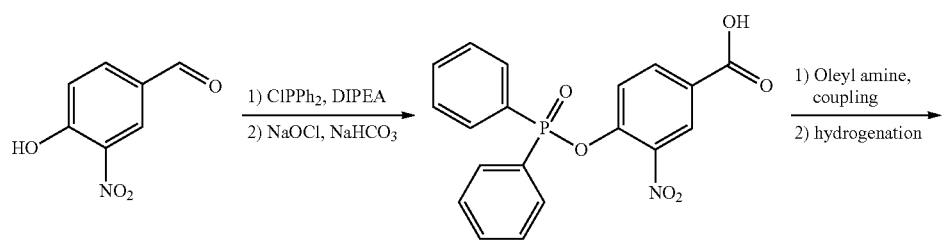

-continued

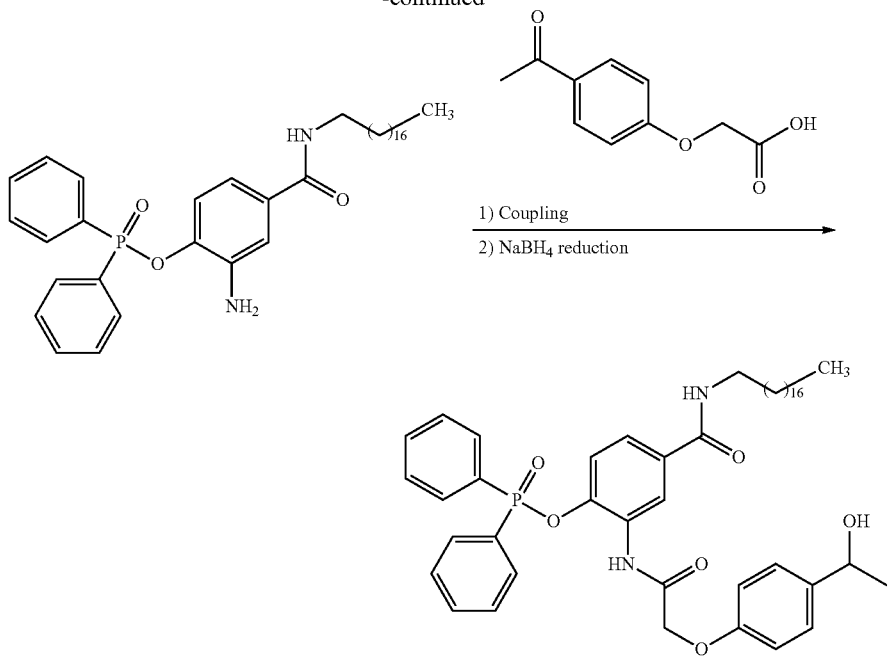

In one embodiment, each constituent (i.e. GAP, spacer, and linker constituents) can be considered a reactant in a given synthesis strategy. For example, in FIG. 23A, the compound 3 can be considered a GAP constituent, or a group-assisted purification molecule. Compound 4 can be considered a spacer constituent, that when coupled with the GAP constituent, can then facilitate coupling to a linker constituent, such as compound 6. The ultimate resulting GAP anchor, compound 7, can then be reduced at the free linker moiety to provide, e.g., a benzyl alcohol capable of participating in, for example, a nucleophilic substitution reaction, such as a coupling reaction known in the art with respect to peptide chemistry. In another example, such as in FIG. 23B, a GAP constituent can take the form of either ClPPh$_2$ or compound 2. A spacer constituent can be oleyl amine, that when coupled to the GAP constituent, can form a Gap-spacer molecule, such as compound 3. This can then be coupled with a linker constituent, such as compound 4, to ultimately yield a GAP anchor such as compound 5.

Additional embodiments of the claimed invention include:

1. A protecting group for solution-phase peptide synthesis, the protecting group having a chemical formula selected from the group consisting of Chemical Formula 1, Chemical Formula 2, Chemical Formula 3, Chemical Formula 4, Chemical Formula 5, Chemical Formula 6, Chemical Formula 7, and Chemical Formula 8;

wherein Chemical Formula 1 is:

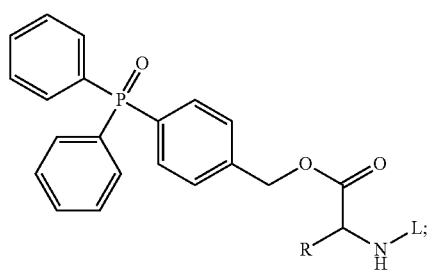

wherein Chemical Formula 2 is:

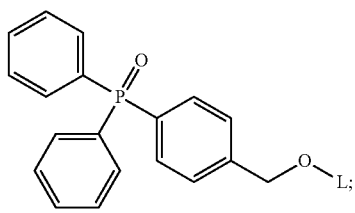

wherein Chemical Formula 3 is:

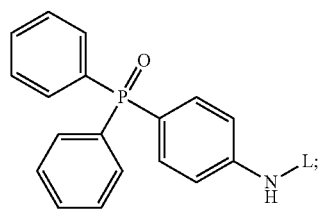

wherein Chemical Formula 4 is:

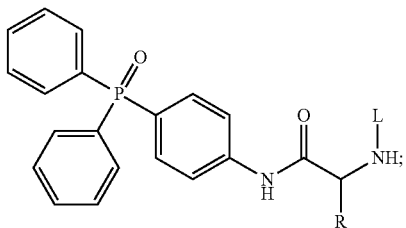

wherein Chemical Formula 5 is:

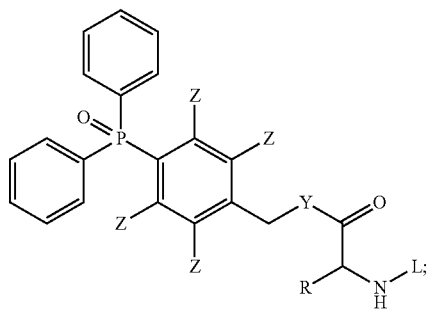

wherein Chemical Formula 6 is:

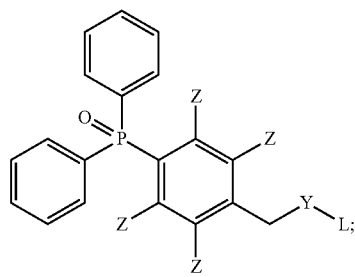

wherein Chemical Formula 7 is:

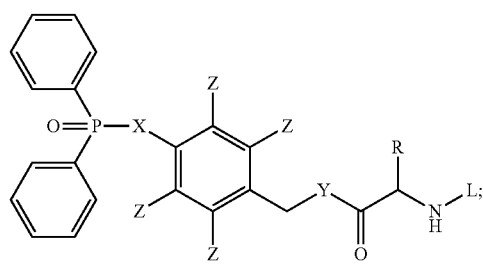

wherein Chemical Formula 8 is:

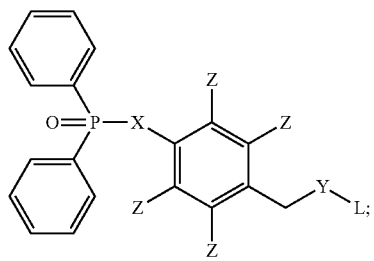

wherein:
Z is selected from the group consisting of: —H, a methyl group (-Me), and a methoxy group (—OMe);
Y is selected from the group consisting of: —O—, —S—, and —NH—;
X is selected from the group consisting of: —O—, —S—, and —NH—;
R is selected from the group consisting of known side chains of protected amino
acids and known side chains of unprotected amino acids; and
L is selected from the group consisting of: 4-(hydroxymethyl)phenoxyacetyl ("HMPA"), 4-(hydroxymethyl)phenoxybutanoyl ("HMPB"), 4-(hydroxymethyl)benzoyl ("HMB"), 4-(mercaptomethyl)benzoyl ("MMB"), 4-(mercaptomethyl)phenoxyacetyl ("MMPA"), 4-(aminomethyl)phenoxyacetyl ("AMPA"), 4-(3,3-dimethyl-3-hydroxypropyl)phenoxyacetyl ("DMPPA"), 2-(4-(amino(2,4-dimethoxyphenyl)methyl)phenoxy)acetyl ("Rink Amide"), 4-((9-amino-9H-xanthen-3-yl)oxy)butanoyl ("Xanthenyl"), 5-(5-amino-10,11-dihydro-5H-dibenzo[a,d][7]annulen-3-yl)pentanoyl ("TCA"), and 3-(4-(chloro(2-chlorophenyl)(phenyl)methyl)phenyl)propanoyl ("2-Chlorotrityl")

2. The protecting group of clause 1, wherein the protecting group is selected from a group consisting of Chemical Formula 1, Chemical Formula 4, Chemical Formula 5, and Chemical Formula 7; and wherein R is the side-chain of an amino acid.

3. The protecting group of clause 1, wherein R is selected from the group consisting of: —H, methyl, —CH2SH, —CH2CH2COOH, —CH2COOH, benzyl, 4-(1H-imidazolyl)methyl, —CH(CH3)(CH2CH3), —CH2CH2CH2CH2NH2, —CH2CH2CH2NH2, isobutyl, —CH2CH2SCH3, —CH2CONH2, —CH2CH2CONH2, a propyl group wherein the 1-position of the propyl group is attached to the same position as the R group and the 3-position of the propyl group is attached to the nitrogen, —CH2CH2CH2N═C(NH2)2, —CH2OH, 1-hydroxyethyl, isopropyl, 4-hydroxybenzyl, and 3-(1H-indolyl)methyl.

4. A method of performing solution-phase peptide synthesis, wherein the method comprises the steps of:
attaching a first protecting group to a first amino acid to provide a first protected amino acid, wherein the first protecting group is the protecting group of claim 1; and
performing a coupling reaction on the first protected amino acid or a peptide formed by linking the first amino acid to another molecule.

5. The method of clause 4, wherein the first protecting group is attached to the C-terminus of the of the first amino acid.

6. The method of clause 4, wherein the first protecting group is attached to the side-chain of the first amino acid.

7. The method of clause 4, wherein the first protecting group is attached to the N-terminus of the first amino acid.

8. The method of clause 4, wherein the method comprises:

coupling a second protected amino acid to the first protected amino acid;

wherein the second protected amino acid comprises a second protecting group and a second amino acid, wherein the second amino acid comprises a side chain, wherein the second protecting group is attached to the side chain of the second amino acid; wherein the second protecting group has a chemical formula selected from the group consisting of Chemical Formula 1, Chemical Formula 2, Chemical Formula 3, Chemical Formula 4, Chemical Formula 5, Chemical Formula 6, Chemical Formula 7, and Chemical Formula 8.

9. The method of clause 8, wherein the step of attaching the first protecting group comprises attaching the first protecting group to the C-terminus of the first amino acid, the N-terminus of the first amino acid, or the side chain of the first amino acid.

10. A method of forming a protecting group for solution-phase peptide synthesis, the method comprising:

coupling benzyl diphenylphosphine oxide (HOBnDpp), aniline diphenylphosphine oxide (NH2PhDpp), or a derivative thereof (i) directly to a linker molecule, (ii) to a linker molecule via an amino acid, or (iii) to a linker molecule via an amino acid derivative.

11. The method of clause 10, wherein the coupling step comprises coupling

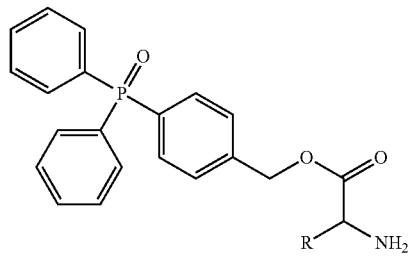

to L-OH to form the protecting group, wherein the protecting group is defined by Chemical Formula 1:

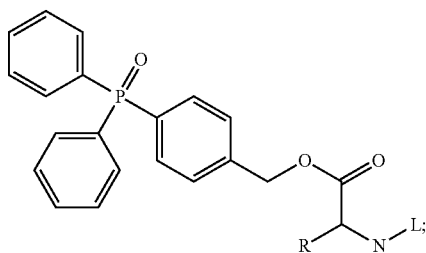

wherein:

R is selected from the group consisting of known side chains of protected amino acids and known side chains of unprotected amino acids; and L is selected from the group consisting of: HMPA, HMPB, HMB, MMB, MMPA, AMPA, DMPPA, Rink Amide, Xanthenyl, TCA, and 2-Chlorotrityl.

12. The method of clause 10, wherein the coupling step comprises coupling

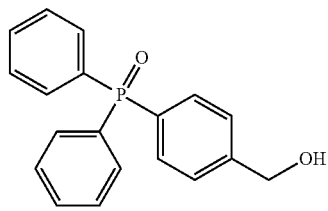 [SMILES: O=P(c1ccccc1)(c1ccccc1)c1ccc(CO)cc1]

to L-OH to form the protecting group, wherein the protecting group is defined by Chemical Formula 2:

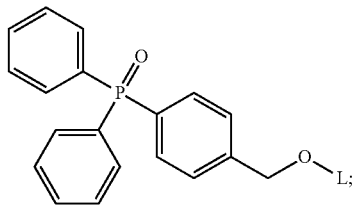

wherein:

L is selected from the group consisting of: HMPA, HMPB, HMB, MMB, MMPA, AMPA, DMPPA, Rink Amide, Xanthenyl, TCA, and 2-Chlorotrityl.

13. The method of clause 10, wherein the coupling step comprises coupling

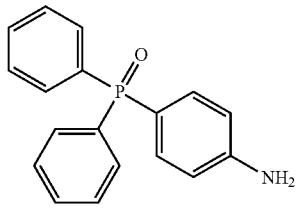 [SMILES: Nc1ccc(P(=O)(c2ccccc2)c2ccccc2)cc1]

to L-OH to form the protecting group, wherein the protecting group is defined by Chemical Formula 3:

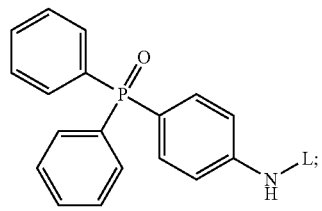

wherein:

L is selected from the group consisting of: HMPA, HMPB, HMB, MMB, MMPA, AMPA, DMPPA, Rink Amide, Xanthenyl, TCA, and 2-Chlorotrityl.

14. The method of clause 10, wherein the coupling step comprises coupling

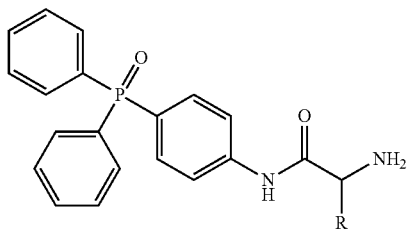

to L-OH to form the protecting group, wherein the protecting group is defined by Chemical Formula 4:

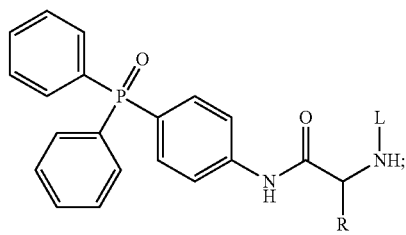

wherein:
R is selected from the group consisting of known side chains of protected amino acids and known side chains of unprotected amino acids; and
L is selected from the group consisting of: HMPA, HMPB, HMB, MMB, MMPA, AMPA, DMPPA, Rink Amide, Xanthenyl, TCA, and 2-Chlorotrityl.

15. The method of clause 10, wherein the coupling step comprises coupling

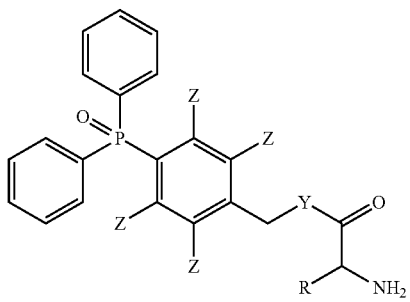

to L-OH to form the protecting group, wherein the protecting group is defined by Chemical Formula 5:

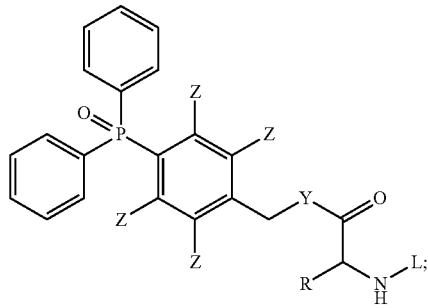

wherein:
Z is selected from the group consisting of: —H, -Me, and —OMe;
Y is selected from the group consisting of: —O—, —S—, and —NH—;
R is selected from the group consisting of known side chains of protected amino acids and known side chains of unprotected amino acids; and
L is selected from the group consisting of: HMPA, HMPB, HMB, MMB, MMPA, AMPA, DMPPA, Rink Amide, Xanthenyl, TCA, and 2-Chlorotrityl.

16. The method of clause 10, wherein the coupling step comprises coupling

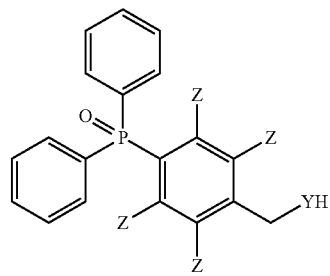

to L-OH to form the protecting group, wherein the protecting group is defined by Chemical Formula 6:

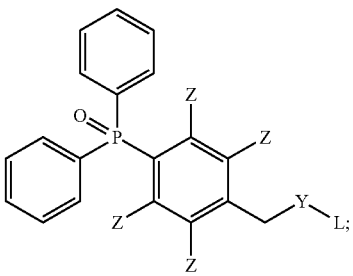

wherein:
Z is selected from the group consisting of: —H, -Me, and —OMe;
Y is selected from the group consisting of: —O—, —S—, and —NH—; and
L is selected from the group consisting of: HMPA, HMPB, HMB, MMB, MMPA, AMPA, DMPPA, Rink Amide, Xanthenyl, TCA, and 2-Chlorotrityl.

17. The method of clause 10, wherein the coupling step comprises coupling

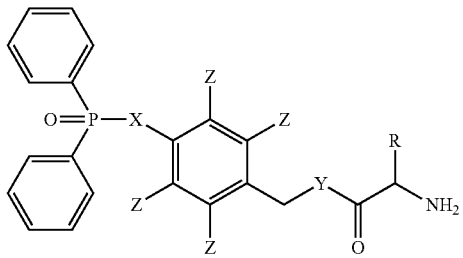

to L-OH to form the protecting group, wherein the protecting group is defined by Chemical Formula 7:

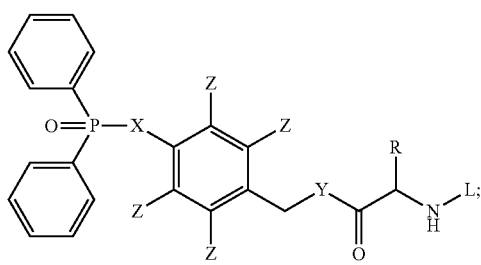

wherein:

Z is selected from the group consisting of: —H, -Me, and —OMe;

Y is selected from the group consisting of: —O—, —S—, and —NH—;

X is selected from the group consisting of: —O—, —S—, and —NH—;

R is selected from the group consisting of known side chains of protected amino acids and known side chains of unprotected amino acids; and L is selected from the group consisting of: HMPA, HMPB, HMB, MMB, MMPA, AMPA, DMPPA, Rink Amide, Xanthenyl, TCA, and 2-Chlorotrityl.

18. The method of clause 10, wherein the coupling step comprises coupling

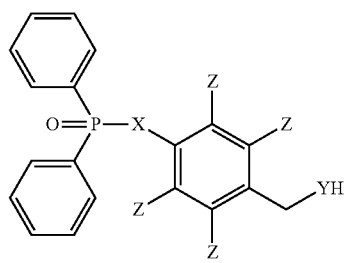

to L-OH to form the protecting group, wherein the protecting group is defined by Chemical Formula 8:

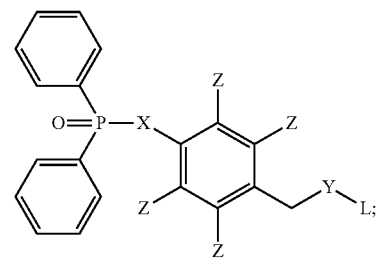

wherein:

Z is selected from the group consisting of: —H, -Me, and —OMe;

Y is selected from the group consisting of: —O—, —S—, and —NH—;

X is selected from the group consisting of: —O—, —S—, and —NH—; and

L is selected from the group consisting of: HMPA, HMPB, HMB, MMB, MMPA, AMPA, DMPPA, Rink Amide, Xanthenyl, TCA, and 2-Chlorotrityl.

What is claimed is:

1. A chemical composition comprising a Group Assisted Purification (GAP) constituent, a spacer constituent, and a linker constituent, wherein the spacer constituent is disposed between the GAP constituent and the linker constituent, wherein the GAP constituent is selected from the group consisting of:

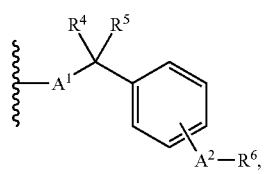

Formula A)

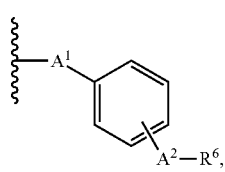

(Formula B)

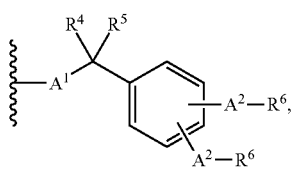

(Formula C)

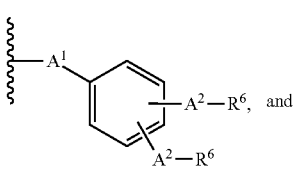

(Formula D)

-continued (Formula E)

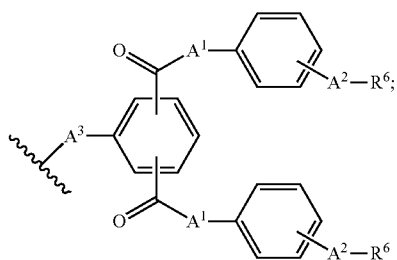

wherein:
- $A^1$ is selected from the group consisting of: S, O, NH, NMe, NEt, NBn, NPh, —C(O)—, and —(CH$_2$)— (wherein "j" is as defined below);
- $A^2$ is selected from the group consisting of: 0 and —(CH$_2$)$_k$— (wherein "k" is 0);
- $A^3$ is selected from the group consisting of: NH, NMe, NEt, NBn, and NPh;
- $R^4$ is selected from the group consisting of: —(CH$_2$)$_m$—H (wherein "m" is as defined below), —CCl$_3$, —CF$_3$, phenyl, isopropyl, tert-butyl, chlorophenyl, dichlorophenyl, methoxyphenyl, and dimethoxyphenyl;
- $R^5$ is selected from the group consisting of: —(CH$_2$)$_p$-Me (wherein "p" is as defined below), —CCl$_3$, —CF$_3$, phenyl, isopropyl, tert-butyl, chlorophenyl, dichlorophenyl, methoxyphenyl, and dimethoxyphenyl;
- $R^6$ is selected from the group consisting of Dpp and Dpop, wherein:

Dpp is an abbreviation for the following:

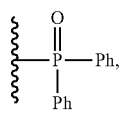

and

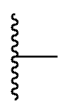

Dpop is an abbreviation for the following:

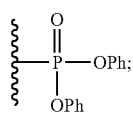

and
j, m and p are separate values selected from the group consisting of any integer from 0 to 30; and wherein the linker constituent is selected from the group consisting of:

(Formula III)

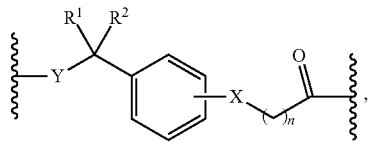

(Formula VI)

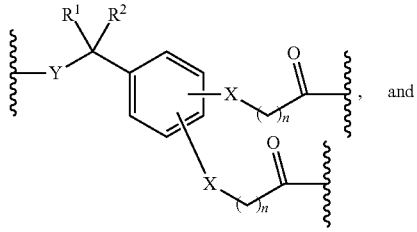

(Formula VII)

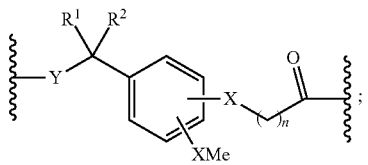

wherein:
- X is 0;
- Y is selected from the group consisting of: S, NH, NMe, NEt, NBn, NPh, and 0;
- $R^1$ is selected from the group consisting of: —(CH$_2$)$_b$—H (wherein "b" is as defined below), —CCl$_3$, —CF$_3$, phenyl, isopropyl, tert-butyl, chlorophenyl, dichlorophenyl, methoxyphenyl, and dimethoxyphenyl;
- $R^2$ is selected from the group consisting of: —(CH$_2$)$_c$—H (wherein "c" is as defined below), —CCl$_3$, —CF$_3$, phenyl, isopropyl, tert-butyl, chlorophenyl, dichlorophenyl, methoxyphenyl, and dimethoxyphenyl;
- a, b, and c, are separate values selected from the group consisting of any integer from 0 to 30;
- and n is any integer from 1 to 30; and wherein the spacer constituent is selected from the group consisting of:

(Formula X)

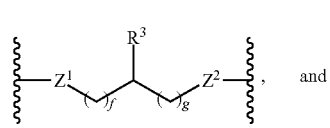

and (Formula Y)

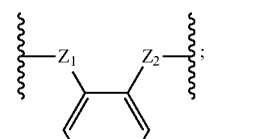

wherein:
- $Z^1$ is selected from the group consisting of: NH, NMe, NEt, NBn, and, NPh;
- $Z^2$ is selected from the group consisting of: S, O, NH, NMe, NEt, NBn, NPh, —C(O)—, and —(CH$_2$)$_e$— (wherein "e" is as defined below);

e, f, g, h, i, and z are separate values selected from the group consisting of any integer from 0 to 30; and $R^3$ is selected from the group consisting of: H, methyl, ethyl, propyl, isopropyl, benzyl, isobutyl, sec-butyl, tert-butyl, 2-(methylmercapto)ethyl, and the structures listed below:

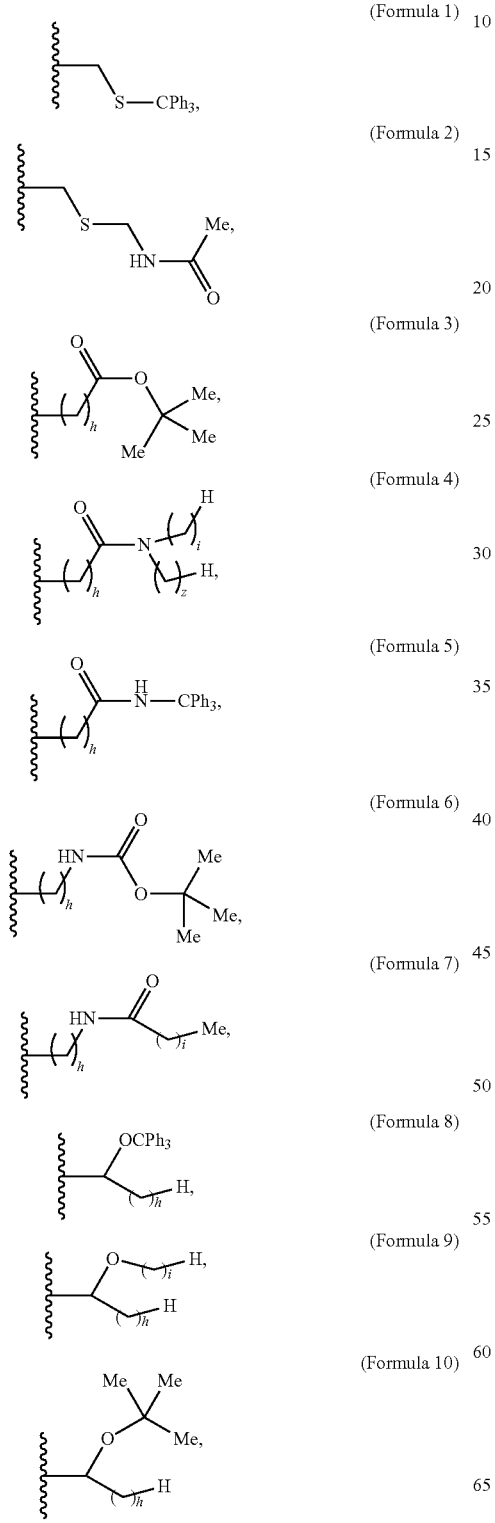

(Formula 1)
(Formula 2)
(Formula 3)
(Formula 4)
(Formula 5)
(Formula 6)
(Formula 7)
(Formula 8)
(Formula 9)
(Formula 10)

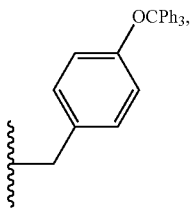

(Formula 11)

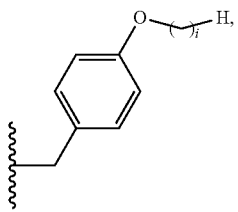

(Formula 12)

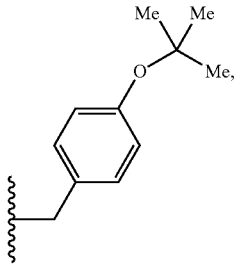

(Formula 13)

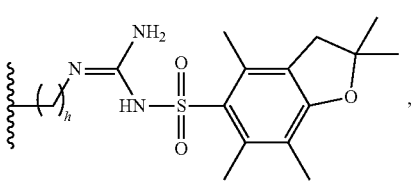

(Formula 14)

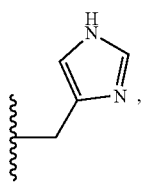

(Formula 15)

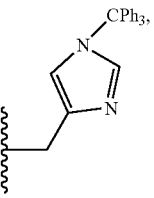

(Formula 16)

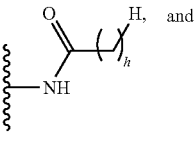

(Formula 17)

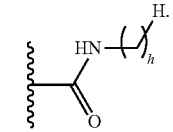

(Formula 18)

2. The composition of claim 1, wherein the linker constituent is selected from the group consisting of: 4-(hydroxymethyl)phenoxyacetyl ("HMPA"), 4-(hydroxymethyl)phenoxybutanoyl ("HMPB"), 4-(hydroxymethyl)benzoyl ("HMB"), 4-(mercaptomethyl)phenoxyacetyl ("MMPA"), 4-(aminomethyl)phenoxyacetyl ("AMPA"), and 4-(3,3-dimethyl-3-hydroxypropyl)phenoxyacetyl ("DMPPA").

3. The composition of claim 1, wherein the GAP constituent is:

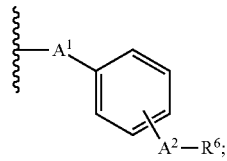

and
the spacer constituent is:

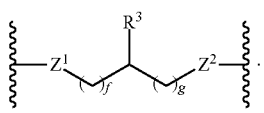

4. The composition of claim 1, wherein the GAP constituent is:

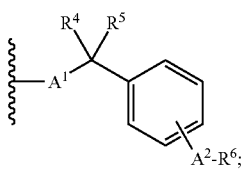

the linker constituent is:

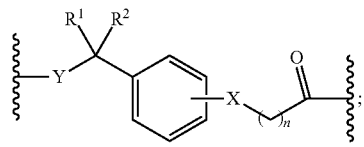

and
the spacer constituent is:

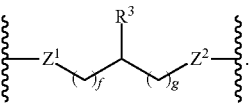

5. The composition of claim 4, wherein the GAP constituent, the spacer constituent, and the linker constituent together comprise:

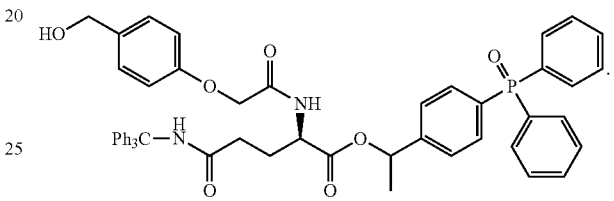

6. The composition of claim 1, comprising at least one compound selected from the group consisting of:

(Compound 1)

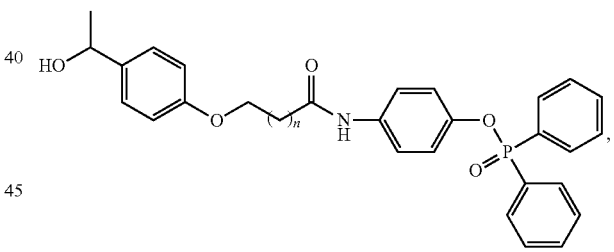

wherein n=2 or 9;

(Compound 2)

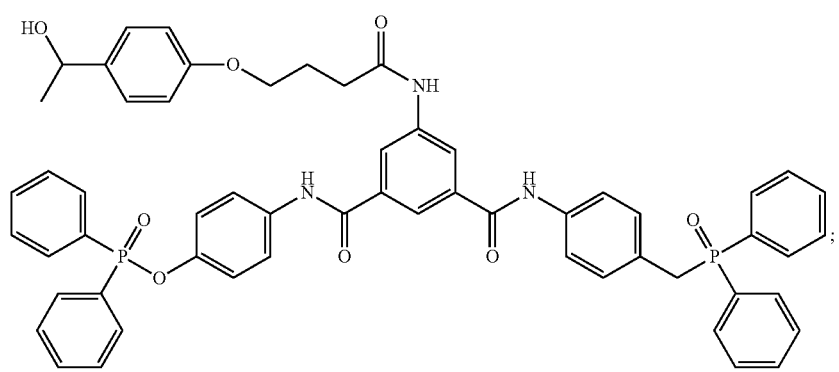

-continued
(Compound 3)
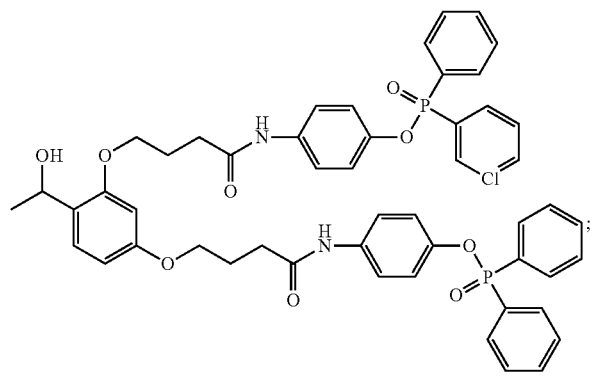
(Compound 4)
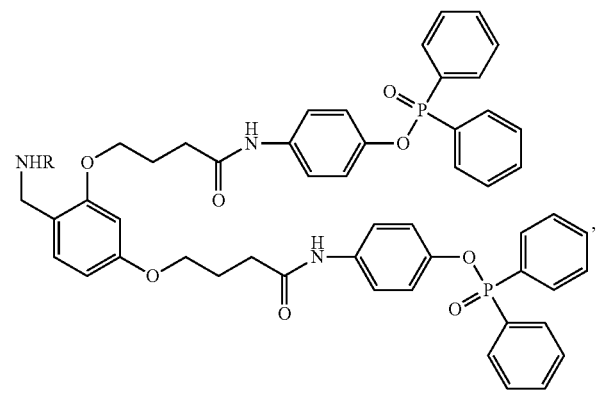
wherein R=H, Me, Et, or iPr;
(Compound 5)
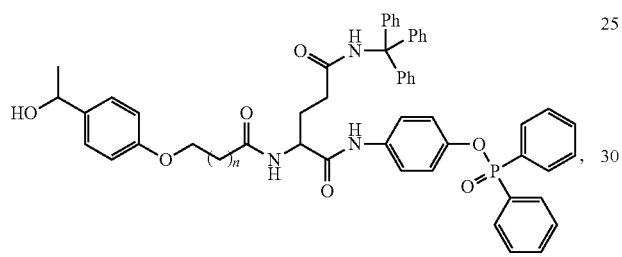
wherein n=0 or 2;
(Compound 6)
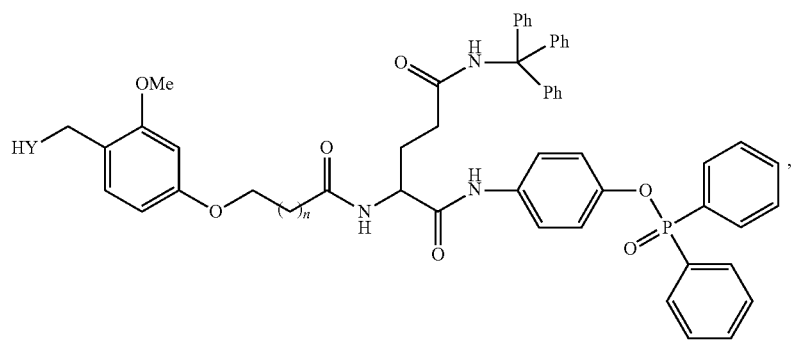
wherein n=0 or 2, and wherein Y=O, NMe, NEt, or N-iPr;
(Compound 7)
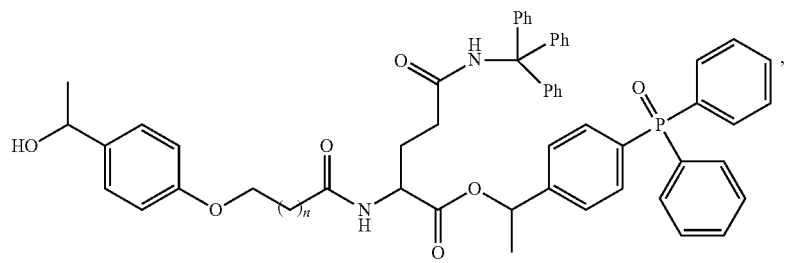
wherein n=0 or 2;

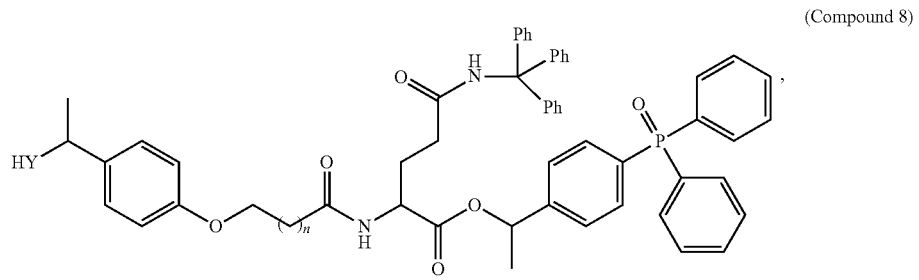
(Compound 8)
wherein n=0 or 2, and wherein Y=O, NMe, NEt, or N-iPr;
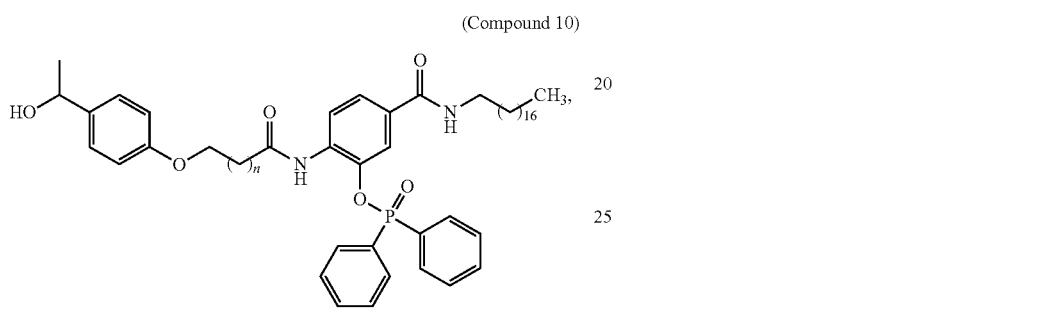
(Compound 10)
wherein n=0 or 2; and
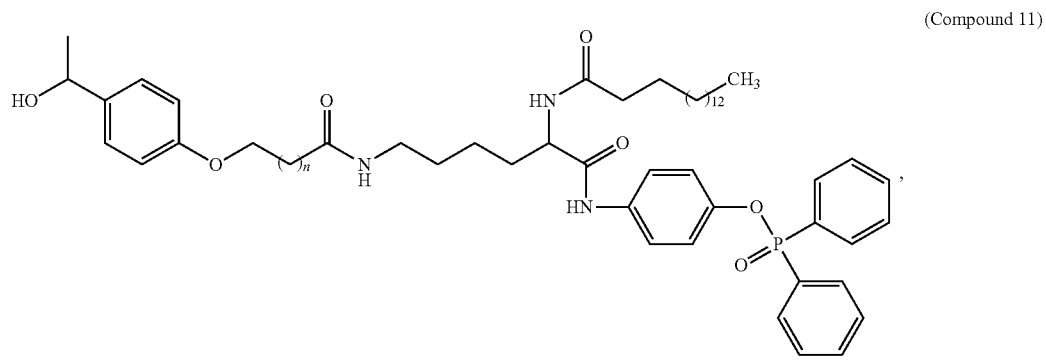
(Compound 11)
wherein n=0 or 2.
* * * * *

UNITED STATES PATENT AND TRADEMARK OFFICE
CERTIFICATE OF CORRECTION

| | | |
|---|---|---|
| PATENT NO. | : 12,024,537 B2 | Page 1 of 2 |
| APPLICATION NO. | : 17/104166 | |
| DATED | : July 2, 2024 | |
| INVENTOR(S) | : Cole Seifert | |

It is certified that error appears in the above-identified patent and that said Letters Patent is hereby corrected as shown below:

On the Title Page

Item (56) under OTHER PUBLICATIONS: "luorene-derived" should be -- fluorene-derived --.

In the Claims

Column 53, Claim 1, Line 16: "—(CH$_2$)—" should be -- —(CH$_2$)$_j$— --.

Column 53, Claim 1, Line 18: "0" should be -- O --.

Column 53, Claim 1, Lines 34-39 (approx.): "Dpp is an abbreviation for the following:" should be -- Dpp is an abbreviation for the following: --.

Column 53, Claim 1, Lines 50-57 (approx.): "Dpop is an abbreviation for the following:" should be -- Dpop is an abbreviation for the following: --.

Column 54, Claim 1, Line 30 (approx.): "0;" should be -- O; --.

Column 54, Claim 1, Line 32 (approx.): "0;" should be -- O; --.

Signed and Sealed this
First Day of October, 2024

Katherine Kelly Vidal
*Director of the United States Patent and Trademark Office*

CERTIFICATE OF CORRECTION (continued)
U.S. Pat. No. 12,024,537 B2

Column 57-58, Claim 6, Line 53-65 (approx.):

" 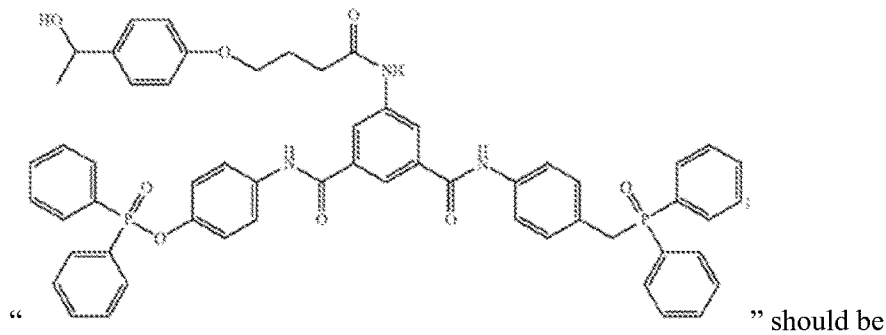 " should be

-- 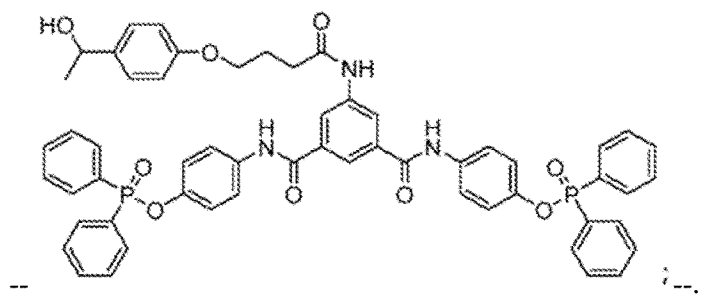 ;--.

Column 59, Claim 6, Line 20 (approx.): "R=H," should be -- R = H, --.

Column 59, Claim 6, Line 50 (approx.): "Y=O," should be -- Y = O, --.

Column 61, Claim 6, Line 15: "Y=O," should be -- Y = O, --.